United States Patent [19]

Ishikawa et al.

[11] Patent Number: 4,988,681
[45] Date of Patent: Jan. 29, 1991

[54] PHOSPHINIC ACID DERIVATIVES

[75] Inventors: Kiyofumi Ishikawa, Chofu; Takehiro Fukami, Ichikawa; Hiroshi Naganuma, Hachioji; Kyoko Nakamichi, Tokyo, all of Japan

[73] Assignee: Banyu Pharmaceutical Co., Ltd., Tokyo, Japan

[21] Appl. No.: 370,190

[22] Filed: Jun. 22, 1989

[30] Foreign Application Priority Data

Jun. 23, 1988 [JP] Japan .................. 63-155830

[51] Int. Cl.$^5$ .................. A61K 31/66; A61K 31/675; C07F 9/30; C07C 69/00
[52] U.S. Cl. ...................... 514/93; 514/94; 514/120; 546/24; 548/119; 558/182; 560/125; 560/205; 562/11; 562/24
[58] Field of Search .................. 562/11, 24; 560/125, 560/205; 558/182; 548/119; 546/24; 514/93, 94, 120

[56] References Cited

U.S. PATENT DOCUMENTS

| 4,374,131 | 2/1983 | Petrillo | 546/24 |
| 4,444,765 | 4/1984 | Karanewsky et al. | 548/119 |
| 4,452,791 | 6/1984 | Ryono et al. | 548/119 |
| 4,715,994 | 12/1987 | Parsons et al. | 562/15 |
| 4,885,283 | 12/1989 | Broadhurst et al. | 514/93 |

FOREIGN PATENT DOCUMENTS

| 266978 | 5/1988 | European Pat. Off. | 562/16 |
| 13095 | 1/1989 | Japan | 562/16 |

OTHER PUBLICATIONS

Pitchett et al., "Chem. Abstracts", vol. 107 (11) 97134k (1987).

Primary Examiner—J. E. Evans
Attorney, Agent, or Firm—Sherman and Shalloway

[57] ABSTRACT

A phosphinic acid derivative represented by the general formula [I], or a pharmaceutically acceptable salt thereof,

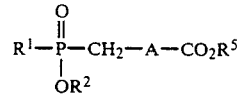

[I]

wherein $R^1$ represents an alkyl, cycloalkyl or aralkyl group which may be substituted; $R^2$ and $R^5$ may be identical or different, and each represents a hydrogen atom, or an ester residue capable of forming a non-toxic ester hydrolyzable in vivo; and A represents a group of the formula

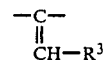

wherein $R^3$ represents an alkyl group, a group of the formula

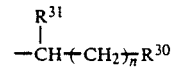

wherein $R^{30}$ represents a halogen atom, a carboxyl group, a hydroxyl group, a cycloalkyl group which may be substituted, an aryl group which may be substituted, an arylthio group, a heteroarylthio group which may be substituted, an alkylthio group which may be substituted, an amino group which may be substituted, or a lower alkoxycarbonyl group; $R^{31}$ represents a hydrogen atom or a lower alkyl group; and n represents an integer of 0 to 6, a cycloalkyl group which may be substituted or an aryl group which may be substituted; and the double bond at A has a Z-configuration, or a group of the formula

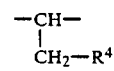

wherein $R^4$ represents a cycloalkyl group which may be substituted. Said phosphinic acid derivative is useful for reducing renal toxicity induced by a carbapenem or penem antibiotic and for inhibiting dipeptidase.

13 Claims, No Drawings

PHOSPHINIC ACID DERIVATIVES

This invention relates to phosphinic acid derivatives, and more specifically, to novel phosphinic acid derivatives having dipeptidase inhibitory activity which are used in combination with carbapenem or penem antibiotics, to synthetic intermediates thereof, and to use thereof.

Carbapenem or penem antibiotics have a broad antibacterial spectrum and strong bactericidal activity which are not seen in conventional antibiotics, and moreover are stable to beta-lactamases produced by bacteria. Accordingly, the carbapenem and penem antibiotics are characterized by showing no cross-resistance with conventional beta-lactam antibiotics. The mechanism of action of these new antibiotics is the specific inhibition of the biosynthesis of cellular wall peptide glycan in bacteria. Since this is the same as in conventional beta-lactam antibiotics such as penicillins and cephalosporins, these new antibiotics are also highly safe.

These antibiotics are generally stable in the presence of beta-lactamases produced by bacteria, but have the common defect that they are susceptible to inactivation by mammalian dipeptidase, i.e. dehydropeptidase-I ("DHP-I" for short).

The first solution to this problem was achieved by the use of imipenem, a carbapenem antibiotic, in combination with cilastatin which is a selective DHP-I inhibitor. This combined use was shown to greatly improve urinary recovery of imipenem and prevent its potential renal toxicity J. Antimicrob. Chemother., vol. 12, Suppl. D, pages 1-35 (1983) and Chemotherapy, vol. (S-4), pages 217-226 (1985)). Furthermore, some proposals have been made on DHP-I inhibitors and agents for reducing the renal toxicity of carbapenem and penem antibiotics (see, for example, U.S. Pat. No. 4,715,994, and European Laid-Open Patent Publications Nos. 248565, 161546, 72014, 49389, 28778 and 10573).

DHP-I inhibitory compounds described in the above-cited literature including cilastatin do not always have satisfactory duration of action, and do not show sufficient activity in oral administration.

The present inventors made extensive investigations in order to solve the problem of the compounds including cilastatin which are described in the known literature. These investigations have led to the discovery that compounds represented by the following general formula [I] have a long duration in vivo, and show DHP-I inhibitory activity even in oral administration.

Thus, according to this invention, there is provided a phosphinic acid derivative represented by the general formula

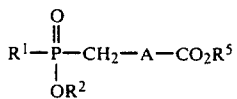   [I]

wherein $R^1$ represents an alkyl, cycloalkyl or aralkyl group which may be substituted; $R^2$ and $R^5$ may be identical or different, and each represents a hydrogen atom, or an ester residue capable of forming a non-toxic ester hydrolyzable in vivo; and A represents a group of the formula

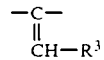

wherein $R^3$ represents an alkyl group, a group of the formula

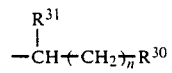

wherein $R^{30}$ represents a halogen atom, a carboxyl group, a hydroxyl group, a cycloalkyl group which may be substituted, an aryl group which may be substituted, an arylthio group, a heteroarylthio group which may be substituted, an alkylthio group which may be substituted, an amino group which may be substituted, or a lower alkoxycarbonyl group; $R^{31}$ represents a hydrogen atom or a lower alkyl group; and n represents an integer of 0 to 6, a cycloalkyl group which may be substituted or an aryl group which may be substituted; and the double bond at A has a Z-configuration, or a group of the formula

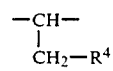

wherein $R^4$ represents a cycloalkyl group which may be substituted, or a pharmaceutically acceptable salt thereof.

According to this invention, there are also provided compounds of the following general formulae which are useful as intermediates for the production of the compound of formula [I],

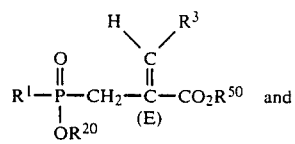   [XXIX]

and

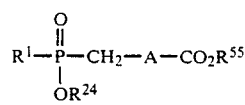   [XXX]

wherein $R^1$, $R^3$ and A are as defined above; $R^{20}$ and $R^{50}$ may be identical or different and each represents a hydrogen atom or a lower alkyl group; and $R^{24}$ and $R^{55}$ may be identical or different and each represents a hydrogen atom or a lower alkyl group; provided that $R^{24}$ and $R^{55}$ are not hydrogen atoms at the same time, or salts thereof.

The present invention also provides uses of a phosphinic acid derivative of general formula [I] or a pharmaceutically acceptable salt thereof.

The various terms within the scope of the invention and described herein are defined below with their specific examples.

The term "lower" to qualify a group or a compound means that the group or compound so qualified has not more than 6 carbon atoms.

The "alkyl group which may be substituted" includes, for example, linear or branched alkyl groups having 1 to 10 carbon atoms, preferably 3 to 10 carbon atoms, such as methyl, ethyl, propyl, isopropyl, butyl, isobutyl, sec-butyl, tert-butyl, pentyl, isopentyl, neopentyl, hexyl, isohexyl, heptyl, octyl, nonyl, and decyl groups, which may be substituted by 1 to 2 substituents selected from halogen atoms (such as chlorine, fluorine or bromine), lower cycloalkyl groups (such as cyclopropyl, cyclobutyl, cyclopentyl or cyclohexyl), (lower-)alkoxy(lower)alkyloxy groups (such as methoxymethyloxy, ethoxymethyloxy, 2-methoxyethyloxy, 1-methoxyethyloxy, 1-ethoxyethyloxy or 2-ethoxyethyloxy) and a hydroxyl group. Specific examples of such alkyl groups or substituted alkyl groups are methyl, ethyl, propyl, isopropyl, butyl, isobutyl, sec-butyl, tert-butyl, hexyl, isohexyl, heptyl, octyl, nonyl, decyl, cyclopropylmethyl, 3-cyclopropylpropyl, 4-cyclopropylbutyl, cyclobutylmethyl, cyclopentylmethyl, cyclohexylmethyl, 3-chloropropyl, 3-bromopropyl, 3-fluoropropyl, 4-chlorobutyl, 4-bromobutyl, 4-fluorobutyl, 5-chloropentyl, 5-bromopentyl, 5-fluoropentyl, 6-chlorohexyl, 3-hydroxypropyl, 4-hydroxybutyl, 5-hydroxypentyl, 3-methoxymethyloxypropyl, 4-methoxymethyloxybutyl, 5-methoxymethyloxypentyl and 6-methoxymethyloxyhexyl groups.

The "cycloalkyl group which may be substituted" includes, for example, cycloalkyl groups having 3 to 6 carbon atoms such as cyclopropyl, cyclobutyl, cyclopentyl and cyclohexyl groups which may be substituted by 1 to 4, preferably 1 to 2, substituents selected from the class consisting of lower alkyl groups (such as methyl, ethyl, propyl, isopropyl, butyl, isobutyl, sec-butyl or tert-butyl), halogen atoms (such as chlorine, bromine or fluorine), a carboxyl group and a hydroxyl group. Specific examples of such cycloalkyl groups and substituted cycloalkyl groups are cyclopropyl, cyclobutyl, cyclopentyl, cyclohexyl, 2-methylcyclopropyl, 2,2-dimethylcyclopropyl, 2,3-dimethylcyclopropyl, 2-methylcyclopentyl, 3-methylcyclopentyl, 2,2-dimethylcyclopentyl, 2,5-dimethylcyclopentyl, 2,2,5,5-tetramethylcyclopentyl, 3-tert-butylcyclopentyl, 2-hydroxycyclopentyl, 3-hydroxycyclopentyl, 2-chlorocyclopentyl, 3-chlorocyclopentyl, 2-fluorocyclopentyl, 3-fluorocyclopentyl, 2-methylcyclohexyl, 2,2-dimethylcyclohexyl, 2,2,6,6-tetramethylcyclohexyl, 3,3-dimethylcyclohexyl, 4,4-dimethylcyclohexyl, 4-tert-butylcyclohexyl, 2-chlorocyclohexyl, 3-chlorocyclohexyl, 4-chlorocyclohexyl, 2-bromocyclohexyl, 3-bromocyclohexyl, 4-bromocyclohexyl, 2-fluorocyclohexyl, 3-fluorocyclohexyl, 4-fluorocyclohexyl, 2-hydroxycyclohexyl, 3-hydroxycyclohexyl, 4-hydroxycyclohexyl, 2-carboxycyclopropyl, 2-carboxycyclobutyl, 3-carboxycyclobutyl, 2-carboxycyclopentyl, 3-carboxycyclopentyl, 2-carboxycyclohexyl, 3-carboxycyclohexyl and 4-carboxycyclohexyl groups.

The "lower alkyl group" may be linear or branched, and includes alkyl groups having 1 to 6 carbon atoms such as methyl, ethyl, propyl, isopropyl, butyl, isobutyl, sec-butyl, tert-butyl, pentyl, isopentyl, neopentyl, tert-pentyl, hexyl and isohexyl groups.

The "aralkyl group which may be substituted" includes, for example, aralkyl groups having 7 to 11 carbon atoms such as benzyl, phenethyl, 3-phenylpropyl and 4-phenylbutyl groups which may be substituted by 1 to 2 (preferably 1) substituents selected from the class consisting of lower alkyl groups (such as methyl, ethyl, propyl, isopropyl, butyl, isobutyl, sec-butyl or tert-butyl), halogen atoms (such as chlorine, bromine or fluorine) and a hydroxyl group. Specific examples of such aralkyl groups and substituted aralkyl groups are 2-methylbenzyl, 2,6-dimethylbenzyl, 4-methylbenzyl, 3,4-dimethylbenzyl, 2,4-dimethylbenzyl, 4-ethylbenzyl, 4-propylbenzyl, 4-butylbenzyl, 4-tert-butylbenzyl, 4-butylphenethyl, 4-tert-butylphenethyl, 3-(4-butylphenyl)propyl, 3-(4-tert-butylphenyl)propyl, 4-(4-butylphenyl)butyl, 4-(4-tert-butylphenyl)butyl, 4-hydroxybenzyl, 3-hydroxybenzyl, 4-hydroxyphenethyl, 3-(4-hydroxyphenyl)propyl, 4-(4-hydroxyphenyl)butyl, 4-chlorobenzyl, 4-fluorobenzyl, 4-bromobenzyl, 4-chlorophenethyl, 4-fluorophenethyl, 3-(4-chlorophenyl)propyl and 4-(4-chlorophenyl)butyl groups.

The "ester residue capable of forming a non-toxic ester hydrolyzable in vivo" includes, for example, ordinary non-toxic ester residues such as 1-(methoxycarbonyloxy)ethyl, 1-(ethoxycarbonyloxy)ethyl, methoxycarbonyloxymethyl, ethoxycarbonyloxymethyl, acetoxymethyl, 1-acetoxyethyl, pivaloyloxymethyl, 1-pivaloyloxyethyl, phthalidyl, (5-methyl-2-oxo-1,3-dioxol-4-yl)methyl, 1-(5-methyl-2-oxo-1,3-dioxol-4-yl)ethyl and (5-phenyl-2-oxo-1,3-dioxol-4-yl)methyl.

The "halogen atom" includes fluorine, chlorine and bromine atoms.

The "arylthio group" includes arylthio groups having 6 to 10 carbon atoms such as phenylthio, 1-naphthylthio and 2-naphthylthio groups.

The "heteroarylthio group which may be substituted" includes heteroarylthio groups having 1 to 4 hetero atoms in the ring selected from nitrogen, oxygen and sulfur atoms such as 2-pyridylthio, 3-pyridylthio, 4-pyridylthio, 2-imidazolylthio, 1,3,4-thiadiazol-2ylthio, 1,2,3-triazol-4-ylthio, tetrazol-5-ylthio, thiazol-2-ylthio, thiazol-4-ylthio, thiazol-5-ylthio, oxazol-2-ylthio, oxazol-4-ylthio and oxazol-5-ylthio groups which may be substituted by 1 to 2 substituents selected from lower alkyl groups, a hydroxyl group and an amino group. Specific examples of such heteroarylthio groups and substituted heteroarylthio groups are 2-pyridylthio, 3-pyridylthio, 4-pyridiylthio, 3-hydroxy-2-pyridylthio, 2-imidazolylthio, 1-methyl-2-imidazolylthio, 1,3,4-thiadiazol-2-ylthio, 5-methyl-1,3,4-thiadiazol-2-ylthio, 1,2,3-triazol-4-ylthio, tetrazol-5-ylthio, 1-methyltetrazol-5-ylthio, thiazol-2-ylthio, 2-aminothiazol-4-ylthio, 2-aminothiazol-5-ylthio, 2-aminoxazol-4-ylthio and 2-aminoxazol-5-ylthio groups.

The "alkylthio group which may be substituted" includes lower alkylthio groups such as methylthio, ethylthio, propylthio, isopropylthio and butylthio groups, which may be substituted by 1 to 3 substituents selected from the class consisting of an amino group, a hydroxyl group, a carboxyl group, and lower alkoxycarbonyl groups such as methoxycarbonyl, ethoxycarbonyl and tert-butoxycarbonyl groups.

The "amino group which may be substituted" includes, for example, an amino group which may be substituted by 1 to 2 substituents selected from the class consisting of lower alkyl groups (such as methyl, ethyl, propyl, isopropyl or butyl), carboxy-lower alkyl groups (such as carboxymethyl), aralkyloxycarbonyl-lower alkyl groups (such as benzyloxycarbonylmethyl) and lower alkoxycarbonyl-lower alkyl groups (such as ethoxycarbonylmethyl).

The "lower alkoxycarbonyl group" includes, for example, methoxycarbonyl, ethoxycarbonyl, propoxycarbonyl, isopropoxycarbonyl, butoxycarbonyl, isobutoxycarbonyl and tert-butoxycarbonyl groups.

The "aryl group which may be substituted" includes, for example, mononuclear or polynuclear aryl groups having 6 to 10 carbon atoms such as phenyl and naphthyl groups, which may be substituted by 1 to 3 substituents, preferably 1 to 2, substituents, selected from the class consisting of lower alkyl groups (such as methyl, ethyl, propyl, isopropyl, butyl, isobutyl or tert-butyl), halogen atoms (such as chlorine, fluorine or bromine), a hydroxyl group, a mercapto group, a carboxyl group, lower alkoxy groups (such as methoxy, ethoxy, propoxy or butoxy), and lower alkylthio groups (such as methylthio, ethylthio, propylthio or butylthio). Specific examples of such aryl groups or substituted aryl groups are phenyl, 1-naphthyl, 2-naphthyl, 4-methylphenyl, 3-methylphenyl, 2-methylphenyl, 2-methyl-1naphthyl, 4-methyl-1-naphthyl, 6-methyl-2-naphthyl, 4-ethylphenyl, 6-ethyl-2-naphthyl, 4-propylphenyl, 6-propyl-2-naphthyl, 6-isopropyl-2-naphthyl, 4-isopropylphenyl, 4-butylphenyl, 6-butyl-2-naphthyl, 4-hydroxyphenyl, 3-hydroxyphenyl, 2-hydroxyphenyl, 4-mercaptophenyl, 4-hydroxy-1-naphthyl, 6-hydroxy-2-naphthyl, 4-mercapto-1-naphthyl, 6-mercapto-2-naphthyl, 4-methoxyphenyl, 4-methoxy-1-naphthyl, 6-methoxy-2-naphthyl, 4-chlorophenyl, 3-chlorophenyl, 2-chlorophenyl, 4-fluorophenyl, 4-bromophenyl, 6-chloro-2-naphthyl, 6-fluoro-2-naphthyl, 4-bromo-1-naphthyl, 6-bromo-2-naphthyl, 3,4-dimethylphenyl, 3,5-dimethylphenyl, 3,4-dichlorophenyl, 3,4-difluorophenyl, 3,4-dibromophenyl and 3,5-dibromophenyl groups.

Thus, a preferred group of compounds of formula [I] provided by this invention are those of formula [I] in which $R^1$ represents a linear or branched alkyl group having 1 to 10 carbon atoms which may be substituted by a hydroxyl group, a lower alkoxy-lower alkyloxy group or a halogen atom; a cycloalkyl-lower alkyl group having 4 to 10 carbon atoms; a cycloalkyl group having 3 to 6 carbon atoms in the ring which may be substituted by 1 to 4 identical or different lower alkyl groups; or an aralkyl group having 7 to 11 carbon atoms;

$R^2$ represents a hydrogen atom;

$R^5$ represents a hydrogen atom, a 1-(lower alkylcarbonyloxy)lower alkyl group, a phthalidyl group, a lower alkoxycarbonylmethyl group or a 1-(5-lower alkyl or phenyl-2-oxo-1,3-dioxol-4-yl)lower alkyl group; and A represents a group of the formula

wherein $R^{3a}$ represents a phenyl group; an aralkyl group having 7 to 11 carbon atoms; a cycloalkyl-lower alkyl group having 4 to 10 carbon atoms; or a linear or branched alkyl group having 1 to 10 carbon atoms or a cycloalkyl group having 3 to 6 carbon atoms in the ring, which may be substituted by a halogen atom, a carboxyl group, a di-lower alkyl-substituted amino group, an N-methyl-N-carboxymethylamino group, a phenylthio group, a triazolylthio group, a carboxy-lower alkylthio group, a lower alkoxycarbonyl-lower alkylthio group, a pyridylthio group optionally substituted by a hydroxyl group, an imidazolylthio group optionally substituted by a lower alkyl group, a hydroxy-lower alkylthio group, an amino-lower alkylthio group or a 2-amino-2-carboxyethylthio group; and the double bond at A has a Z-configuration, or a group of the formula

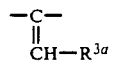

wherein $R^{4a}$ represents a cycloalkyl group having 3 to 6 carbon atoms.

A more preferred group of compounds of formula [I] are those of formula [I] in which $R^1$ represents a linear or branched alkyl group having 3 to 10 carbon atoms; a cycloalkyl group having 3 to 6 carbon atoms in the ring which may be substituted by 1 to 4 identical or different lower alkyl groups; or a cycloalkyl-lower alkyl group having 4 to 10 carbon atoms;

$R^2$ represents a hydrogen atom;

$R^5$ represents a hydrogen atom, a 1-(lower alkylcarbonyloxy)lower alkyl group, a phthalidyl group, a lower alkoxycarbonylmethyl group or a 1-(5-lower alkyl or phenyl-2-oxo-1,3-dioxol-4-yl)lower alkyl group; and A represents a group of the formula

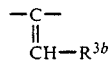

wherein $R^{3b}$ represents a phenyl group; an aralkyl group having 7 to 11 carbon atoms; a cycloalkylmethyl group having 4 to 7 carbon atoms; or a linear or branched alkyl group having 1 to 10 carbon atoms or a cycloalkyl group having 3 to 6 carbon atoms in the ring, which may be substituted by a halogen atom, a carboxyl group, a phenylthio group, a 1,2,3-triazol-4-ylthio group, a carboxy-lower alkylthio group, a lower alkoxycarbonyl-lower alkylthio group, a 3-hydroxy-2-pyridylthio group, a 1-methyl-2-imidazolylthio group, a hydroxy-lower alkylthio group or a 2-amino-2-carboxyethylthio group; and the double bond at A has a Z-configuration, or a group of the formula

wherein $R^{4a}$ represents a cycloalkyl group having 3 to 6 carbon atoms.

An especially preferred group of compounds of formula [I] are those of formula [I] in which $R^1$ represents a linear or branched alkyl group having 3 to 10 carbon atoms; a cycloalkyl group having 3 to 6 carbon atoms in the ring which may be substituted by 1 to 2 lower alkyl groups; or a cycloalkylmethyl group having 4 to 7 carbon atoms;

$R^2$ represents a hydrogen atom;

$R^5$ represents a hydrogen atom, a lower alkylcarbonyloxymethyl group, a phthalidyl group or a (5-methyl-2-oxo-1,3-dioxol-4-yl)methyl group; and A represents a group of the formula

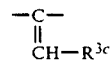

$R^{3c}$ represents a linear or branched alkyl group having 3 to 10 carbon atoms, or a cycloalkyl group having 3 to 6 carbon atoms; and the double bond at A has a Z-configuration.

Specific examples of compounds of formula [I] provided by the present invention include
(Z)-2-(butylhydroxyphosphinoyl)methyl-3-cyclohexylpropenoic acid,
(Z)-3-cyclohexyl-2-(hydroxyisobutylphosphinoyl)methylpropenoic acid,
(Z)-3-cyclohexyl-2-(hydroxyisopropylphosphinoyl)methylpropenoic acid,
(Z)-3-cyclohexyl-2-(decylhydroxyphosphinoyl)methylpropenoic acid,
(Z)-3-cyclohexyl-2-(2,2-dimethylcyclopropylhydroxyphosphinoyl)methylpropenoic acid,
(Z)-2-(hydroxyisobutylphosphinoyl)methyl-2-octenoic acid,
(Z)-2-(hydroxyisobutylphosphinoyl)methyl-2dodecenoic acid,
(Z)-2-(hydroxyisobutylphosphinoyl)methyl-4-methyl-2-pentenoic acid,
(Z)-2-(hydroxyisobutylphosphinoyl)methyl-5-methyl-2-hexenoic acid,
(Z)-3-cyclopropyl-2-(hydroxyisobutylphosphinoyl)methylpropenoic acid,
(Z)-3-cyclopentyl-2-(hydroxyisobutylphosphinoyl)methylpropenoic acid,
(Z)-2-(hydroxyisobutylphosphinoyl)methyl-5-phenyl-2-pentenoic acid,
(Z)-6-chloro-2-(hydroxyisobutylphosphinoyl)methyl-2-hexenoic acid,
(Z)-8-chloro-2-(hydroxyisobutylphosphinoyl)methyl-2-octenoic acid,
(Z)-2-(hydroxyisobutylphosphinoyl)methyl-2-heptenedioic acid,
(Z)-3-cyclopropyl-2-(2,2-dimethylcyclopropylhydroxyphosphinoyl)methylpropenoic acid,
(Z)-2-(cyclohexylmethylhydroxyphosphinoyl)methyl-3-cyclopropylpropenoic acid,
(Z)-3-cyclohexyl-2-(cyclopentylmethylhydroxyphosphinoyl)methylpropenoic acid,
(Z)-2-(hydroxyisobutylphosphinoyl)methyl-6-phenylthio-2-hexenoic acid,
(Z)-2-(hydroxyisobutylphosphinoyl)methyl-6-(1,2,3-triazol-4-yl)thio-2-hexenoic acid,
(Z)-8-carboxymethylthio-2-(hydroxyisobutylphosphinoyl)methyl-2-octenoic acid,
(Z)-2-(hydroxyisobutylphosphinoyl)methyl-8-methoxycarbonylmethylthio-2-octenoic acid,
(Z)-6-(3-hydroxy-2-pyridyl)thio-2-(hydroxyisobutylphosphinoyl)methyl-2-hexenoic acid,
(Z)-6-(L)-2-amino-2-carboxyethyl]thio-2-(hydroxyisobutylphosphinoyl)methyl-2-hexenoic acid,
(Z)-2-(hydroxyisobutylphosphinoyl)methyl-6-(1-methylimidazol-2-yl)thio-2-hexenoic acid,
(Z)-8-(3-hydroxy-2-pyridyl)thio-2-(hydroxyisobutylphosphinoyl)methyl-2-octenoic acid,
2-(butylhydroxyphosphinoyl)methyl-3-cyclohexylpropionic acid,
(5-methyl-2-oxo-1,3-dioxol-4-yl)methyl (Z)-3-cyclohexyl-2-(hydroxyisobutylphosphinoyl)methylpropenoate,
phthalidyl (Z)-3-cyclohexyl-2-(hydroxyisobutylphosphinoyl)methylpropenoate,
pivaloyloxymethyl (Z)-3-cyclohexyl-2-(hydroxyisobutylphosphinoyl)methylpropenoate,
1-acetoxyethyl (Z)-3-cyclohexyl-2-(hydroxyisobutylphosphinoyl)methylpropenoate,
(Z)-2-(hydroxyisobutylphosphinoyl)methyl-3-phenylpropenoic acid,
(Z)-3-cyclohexyl-2-(ethylhydroxyphosphinoyl)methylpropenoic acid,
(Z)-3-cyclohexyl-2-[hydroxy-(4-methoxymethoxybutyl)phosphinoyl]methylpropenoic acid.
(Z)-3-cyclohexyl-2-hydroxy-(4-hydroxybutyl)phosphinoyl]methylpropenoic acid,
(Z)-2-(4-chlorobutylhydroxyphosphinoyl)methyl-3-cyclohexylpropenoic acid,
(Z)-3-cyclohexyl-2-(hexylhydroxyphosphinoyl)methylpropenoic acid,
(Z)-2-(hydroxyisobutylphosphinoyl)methyl-4,4-dimethyl-2-pentenoic acid,
(Z)-2-(benzylhydroxyphosphinoyl)methyl-3-cyclohexylpropenoic acid,
(Z)-3-cyclohexyl-2-(cyclohexylmethylhydroxyphosphinoyl)methylpropenoic acid,
(Z)-6-dimethylamino-2-(hydroxyisobutylphosphinoyl)-methyl-2-hexenoic acid,
(Z)-6-carboxymethylmethylamino-2-(hydroxyisobutylphosphinoyl)methyl-2-hexenoic acid,
(Z)-8-dibutylamino-2-(hydroxyisobutylphosphinoyl)-methyl-2-octenoic acid,
(Z)-6-(2-aminoethyl)thio-2-(hydroxyisobutylphosphinoyl)methyl-2-hexenoic acid,
(Z)-6-(2-hydroxyethyl)thio-2-(hydroxyisobutylphosphinoyl)methyl-2-hexenoic acid,
3-cyclohexyl-2-(hexylhydroxyphosphinoyl)methylpropionic acid,
3-cyclohexyl-2-(ethylhydroxyphosphinoyl)methylpropionic acid,
3-cyclohexyl-2-(hydroxyisopropylphosphinoyl)methylpropionic acid,
3-cyclohexyl-2-(hydroxyisobutylphosphinoyl)methylpropionic acid,
3-cyclohexyl-2-(decylhydroxyphosphinoyl)methylpropionic acid,
3-cyclohexyl-2-(2,2-dimethylcyclopropylhydroxyphosphinoyl)methylpropionic acid,
(Z)-3-cyclohexyl-2-(hydroxyisopentylphosphinoyl)methylpropenoic acid,
(Z)-3-cyclopentyl-2-(cyclopentylhydroxyphosphinoyl)-methylpropenoic acid,
(Z)-2-(2-cyclohexylethylhydroxyphosphinoyl)methyl-3-cyclopropylpropenoic acid,
(Z)-3-cyclopropyl-2-(hydroxyphenethylphosphinoyl)-methylpropenoic acid,
(Z)-2-(hydroxyisobutylphosphinoyl)methyl-8-phenyl-2-octenoic acid,
(Z)-4-cyclopropyl-2-(hydroxyisobutylphosphinoyl)-methyl-2-butenoic acid,
(Z)-4-cyclopentyl-2-(hydroxyisobutylphosphinoyl)-methyl-2-butenoic acid,
(Z)-2-(hydroxyisobutylphosphinoyl)methyl-2-decenedioic acid,
(Z)-2-(hydroxyisobutylphosphinoyl)methyl-4-methyl-2-heptenedioic acid
(Z)-3-(4-carboxycyclohexyl)-2-(hydroxyisobutylphosphinoyl)methylpropenoic acid,
(Z)-5-cyclopropyl-2-(hydroxyisobutylphosphinoyl)-methyl-2-pentenoic acid, and
(Z)-3-cyclohexyl-2-[(2,2-dimethylcyclopentyl)hydroxyphosphinoyl]methylpropenoic acid.

The compounds of formula [I] can exist in the form of pharmaceutically acceptable salts. Examples of such salts include salts with mineral acids such as hydrochloric acid, sulfuric acid and phosphoric acid; and salts with alkali metals or alkaline-earth metals such as sodium, potassium and calcium. Specific examples include disodium salt of (Z)-3-cyclohexyl-2-(hydroxyisobutyl-phosphinoyl)methylpropenoic acid, calcium salt of (Z)-3-cyclohexyl-2-(hydroxyisobutylphosphinoyl)methyl-propenoic acid, disodium salt of (Z)-3-cyclohexyl-2-(2,2-dimethylcyclopropylhydroxyphosphinoyl)methyl-propenoic acid, and (Z)-8-dibutylamino-2-(hydroxyisobutylphosphinoyl)methyl-2-octenoic acid hydrochloride.

The stereochemical relation around the double bond of A which represents a group of the formula

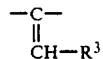

in formula [I] is expressed by prefix Z or E in accordance with IUPAC Rules for The Nomenclature of Organic Chemistry, Section E: Stereochemistry (recommendations 1974) [Pure and Applied Chemistry, vol. 45, pages 11-30 (1976)]. Specifically, $R^3$ which is sequence-rule-preferred between $R^3$ and a hydrogen atom bonded to one carbon atom of the double bond is compared with the group

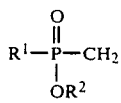

which is sequence-rule-preferred between this group and $CO_2R^5$ bonded to the other carbon atom of the double bond. When the two are on the same side of the reference plane, the prefix Z is used, and when they are on opposite sides of the plane, the prefix E is used.

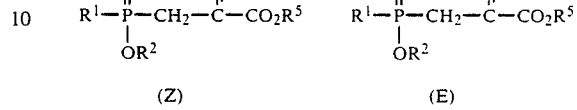

The Z-isomer is preferred in the present invention.

The process for producing the compounds of this invention will now be described. The compounds of the present invention can be produced by any of the following production routes 1 to 9.

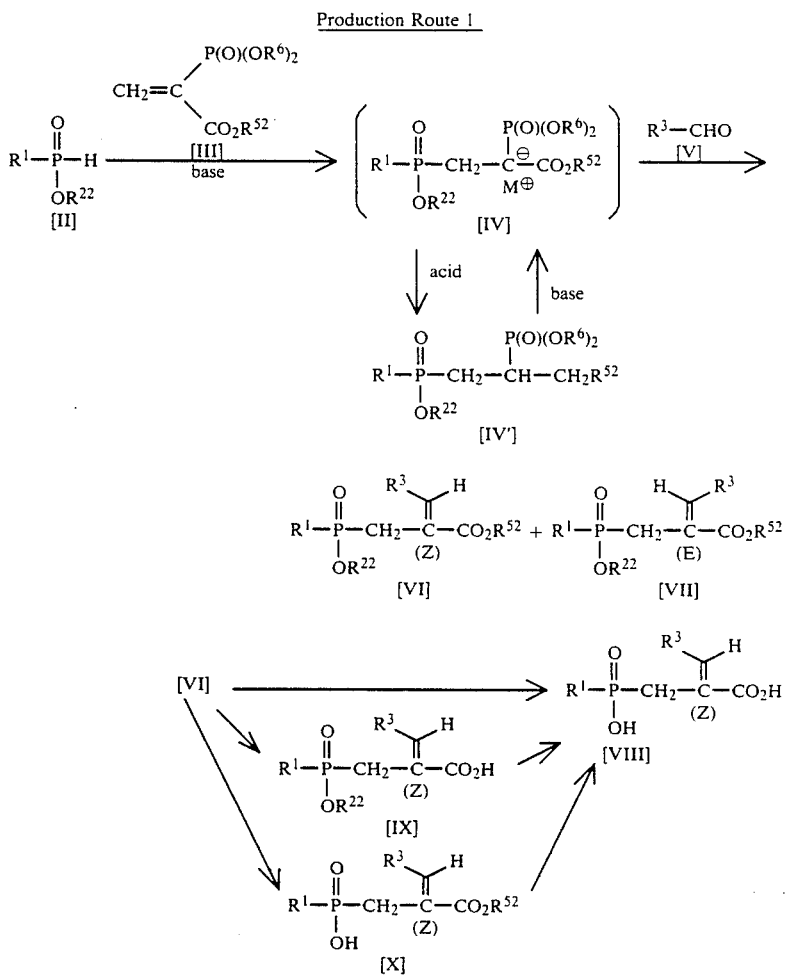

In the above formulae, $R^1$ and $R^3$ are as defined hereinabove; $R^{22}$, $R^{52}$ and $R^6$ may be identical or different and each represents a lower alkyl group; and $M\oplus$ represents a cation, such as a lithium, sodium, potassium or triethyl ammonium ion.

Production Route 2

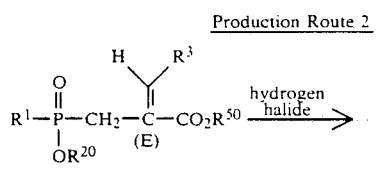

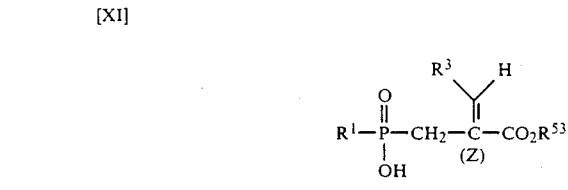

In the formulae, $R^1$, $R^3$, $R^{20}$ and $R^{50}$ are as defined above; $R^{53}$ represents a hydrogen atom or a lower alkyl group.

Production Route 3

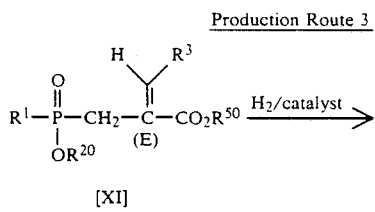

In the formulae, $R^1$, $R^{20}$, $R^3$ and $R^{50}$ are as defined above.

Production Route 4

$$R^1-\underset{\underset{OR^{22}}{|}}{\overset{\overset{O}{\|}}{P}}-CH_2-CH_2-CO_2R^{52} \xrightarrow[base]{R^3-CHO\ [V]}$$

[XIV]

[X] (Z) + [XV] (E)

In the formulae, $R^1$, $R^{22}$, $R^3$ and $R^{52}$ are as defined above.

Production Route 5

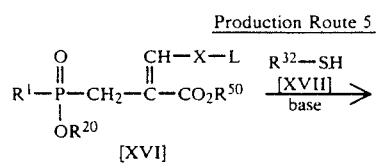

-continued
Production Route 5

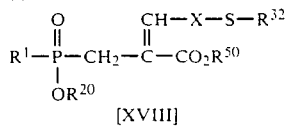

In the formulae, $R^1$, $R^{20}$ and $R^{50}$ are as defined above; $R^{32}$ represents an aryl part in an "arylthio group", an optionally substituted heteroaryl part in a "heteroarylthio group which may be substituted" or an optionally substituted alkyl part in an "alkylthio group which may be substituted"; and X represents a group represented by the formula

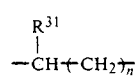

wherein $R^{31}$ and n are as defined above, or a cycloalkylene group; and L represents a leaving group such as a chlorine atom, a bromine atom, a methanesulfonyloxy group or a toluenesulfonyloxy group. The stereochemical relation around the double bond in the compound of formula [XVI] and the compound of formula [XVIII] is Z, E or Z plus E.

Production Route 6

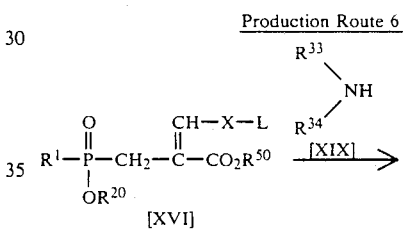

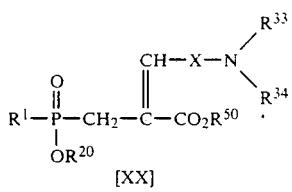

In the formulae, $R^1$, $R^{20}$, $R^{50}$, X and L are as defined above; $R^{33}$ and $R^{34}$ may be identical or different and each represents a hydrogen atom or a substituent in an optionally substituted amino group. The stereochemical relation around the double bond in the compound of formula [XVI] and the compound of formula [XX] is Z, E or Z plus E.

Production Route 7

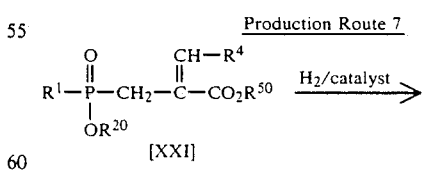

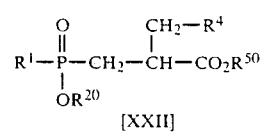

In the formulae, $R^1$, $R^{20}$, $R^4$ and $R^{50}$ are as defined above. The stereochemical relation around the double bond in the compound of formula [XII] is Z, E or Z plus E.

Production Route 8

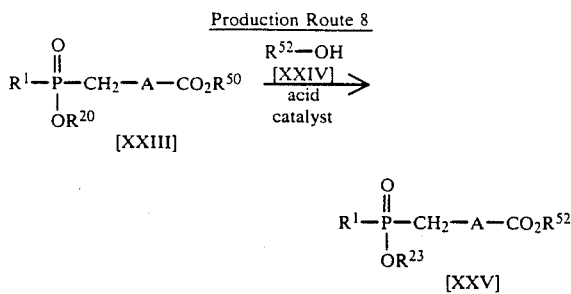

In the formulae, $R^1$, $R^{20}$, $R^{50}$ and A are as defined above; $R^{23}$ represents a hydrogen atom or a lower alkyl group; and $R^{52}$ represents a lower alkyl group.

Production Route 9

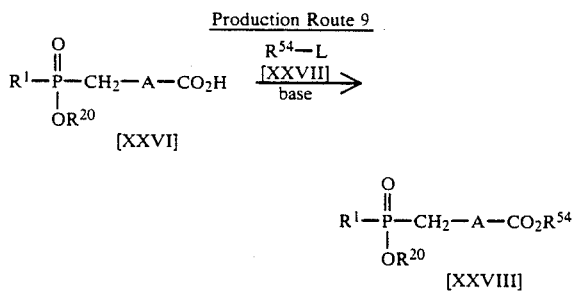

In the formulae, $R^1$, $R^{20}$, A and L are as defined above, and $R^{54}$ represents an ester residue capable of forming a non-toxic ester hydrolyzable in vivo.

PRODUCTION ROUTE 1

The step of producing compound [IV] from compound [II] and compound [III] can be carried out by allowing compound [II] to react with compound [III] in a solvent which does not adversely affect the reaction, at −78° C. to the boiling point of the solvent, preferably 0° C. to room temperature, for 10 minutes to 24 hours, preferably 30 minutes to 2 hours in the presence of a base. Examples of the solvent include alcohols such as methanol, ethanol, isopropanol and tert-butyl alcohol; ethers such as diethyl ether, tetrahydrofuran, dioxane or 1,2-dimethoxyethane; aromatic hydrocarbons such as benzene, toluene and xylene; aprotic dipolar solvents such as acetonitrile, dimethylformamide and dimethyl sulfoxide; and mixtures of these. The base used in this reaction may be, for example, triethylamine, 1,8-diazabicyclo5,4,0]-7-undecene, sodium methoxide, sodium ethoxide, potassium tert-butoxide, sodium hydride, butyl lithium or lithium diisopropylamide.

The amount of compound [III] used is 0.5 to 10 moles, preferably 0.8 to 1.2 moles, per mole of compound [II].

Compound [IV] produced can be used for the next step reaction with compound [V] without isolation and purification. As required, it is possible to isolate and purify it as proton-added compound [IV'] and use it for the reaction with compound [V] in the presence of the above base.

The step of producing compounds [VI] and [VII], Z and E isomers of the olefin, may be carried out by adding 0.5 to 10 moles, preferably 0.8 to 3 moles, per mole of compound [II], of compound [V] to the reaction mixture after the reaction of compound [II] with compound [III] (when compound [IV] is used without prior isolation and purification) and allowing the mixture to stand for 1 hour to 7 days, preferably 3 hours to 24 hours, at −78° C. to the boiling point of the solvent, preferably −50° C. to room temperature. In the case of isolating and purifying compound [IV], an acid is added to the reaction mixture and compound [IV'] is isolated and purified by extraction, crystallization, column chromatography (by, for example, using silica gel), thin-layer chromatography, or combinations of these procedures. The reaction in this case can be carried out by dissolving compound [IV'] in a solvent which does not adversely affect the reaction, adding a base, further adding 0.5 to 10 moles, preferably 0.8 to 3 moles, per mole of compound [IV'], of compound [V], and maintaining the mixture at −78° C. to the boiling point of the solvent, preferably −50° C. to room temperature, for 1 hour to 7 days, preferably 3 hours to 24 hours. Examples of the solvent are alcohols such as methanol, ethanol, isopropanol and tert-butyl alcohol; ethers such as diethyl ether, tetrahydrofuran, dioxane and 1,2-dimethoxyethane; aromatic hydrocarbons such as benzene, toluene or xylene; aprotic dipolar solvents such as acetonitrile, dimethylformamide and dimethyl sulfoxide. Examples of the base include triethylamine, 1,8-diazabicyclo[5,4,0]-7-undecene, sodium methoxide, sodium ethoxide, potassium tert-butoxide, sodium hydride, butyllithium, or lithium diisopropylamide. Compound VI] and compound [VII] , which are Z and E isomers of the olefin, can be separated by such procedures as silica gel column chromatography or thin-layer chromatography.

The step of producing compound [VIII] from compound [VI] by simultaneously carrying out hydrolysis of its carboxylic ester and phosphinic ester can be carried out by treating compound [VI]with at least 2 equivalents, per equivalent of compound [VI[, of an alkali such as lithium hydroxide, sodium hydroxide, potassium hydroxide, calcium hydroxide or tetramethylammonium hydroxide in a solvent which does not adversely affect the reaction (such as water, methanol, ethanol, isopropanol, tetrahydrofuran, dioxane, acetonitrile, dimethylformamide, dimethyl sulfoxide or a mixture of these at room temperature to the boiling point of the solvent for 1 to 48 hours; or by treating compound [VI] with water and an acid such as hydrochloric acid, hydrobromic acid, sulfuric acid, trifluoroacetic acid or methanesulfonic acid in the above-mentioned solvent at room temperature to the boiling point of the solvent for 1 to 48 hours.

The step of producing compound [IX] from compound [VI] via hydrolysis of its carboxylic ester can be carried out by treating compound [VI] with 0.5 to 2 equivalents, preferably 0.9 to 1.1 equivalents, per equivalent of compound [VI], of an alkali such as lithium hydroxide, sodium hydroxide, potassium hydroxide or calcium hydroxide in a solvent which does not adversely affect the reaction, such as water, methanol, ethanol, isopropanol, tetrahydrofuran, dioxane, acetonitrile, dimethylformamide, dimethyl sulfoxide or a mixture of these, at 0° C. to the boiling point of the solvent, preferably 0° C. to room temperature, for 30 minutes to 24 hours.

The step of producing compound [VIII] from compound [IX] via hydrolysis of its phosphinic ester can be carried out in a similar manner as the step of producing compound [VIII] from compound [VI].

The step of producing compound [X] from compound [VI] via de-esterification of its phosphinic ester can be carried out by treating compound [VI] with at least 1 equivalent, per equivalent of compound [VI], of a hydrogen halide such as hydrogen chloride or hydrogen bromide in a solvent which does not adversely affect the reaction, such as methanol, ethanol, isopropanol, ethyl acetate, butyl acetate, diethyl ether, tetrahydrofuran, dioxane, methylene chloride, chloroform, acetonitrile, dimethylformamide, dimethyl sulfoxide or a mixture of these at room temperature to the boiling point of the solvent for 1 to 48 hours. Alternatively, this de-esterification can be effected by treating 1 mole of compound [VI] with 1 to 10 moles of a halosilane such as bromotrimethylsilane in a solvent which does not adversely affect the reaction, such as methylene chloride, chloroform, acetonitrile, dimethylformamide or a mixture of these, at 0° C. to room temperature for 1 to 24 hours, followed by the treatment of the reaction mixture with water at 0° C. to room temperature for 10 minutes to 1 hour.

The step of producing compound [VIII] from compound [X] via hydrolysis of its carboxylic ester can be carried out in a similar manner as the step of producing compound [VIII] from compound [VI].

The compound [VIII] so produced can be purified by using purification means usually practiced in this field, such as solvent extraction, crystallization, column chromatography (silica gel, alumina, ion-exchange resin, etc.), thin-layer chromatography, or a combination of these.

A salt of compound [VIII] can be formed by the action of an alkali such as lithium hydroxide, sodium hydroxide, potassium hydroxide or calcium hydroxide on compound [VIII] in a solvent which does not adversely affect the reaction, such as water, methanol, ethanol, isopropanol, tetrahydrofuran, dioxane, acetonitrile, dimethylformamide, dimethyl sulfoxide or a mixture of these. When the de-esterification reaction of compound [VI], compound [IX] or compound [X] is carried out in the presence of an alkali, the salt of compound [VIII] can be directly crystallized from a suitable reaction solvent selected, and thus isolated and purified.

Compound [VIII] can also be produced by treating a mixture of compound [VI] and compound [VII], without separation, according to either method of EZ isomerization shown in Production Route 2 or 3 and subjecting the product to the hydrolysis reaction, or first subjecting them to the hydrolysis reaction and then treating the product according to either olefin isomerization method.

Compound [II], the starting substance in Production Route 1, can be produced by known methods, for example the methods described in M. I. Kabchnik et al., Doklady Akad. Nauk S.S.S.R., vol. 125, page 1260 (1959); Chemical Abstracts, vol. 53, 21752f (1959), M. Sander, Chem. Ber., vol. 93, page 1220 (1960).

PRODUCTION ROUTE 2

The step of producing compound [XII] from compound [XI] via olefin isomerization can be carried out by treating compound [XI] with a hydrogen halide such as hydrogen chloride or hydrogen bromide in a solvent which does not adversely affect the reaction, for example water, methanol, ethanol, isopropanol, acetic acid, ethyl acetate, butyl acetate, diethyl ether, tetrahydrofuran, dioxane, methylene chloride, chloroform, acetonitrile, dimethyl sulfoxide, or a mixture of these, at room temperature to 200° C. for 30 minutes to 72 hours. If a hydrous solvent is used at this time, the carboxylic ester can be hydrolyzed at the same time. If an alcohol or ester solvent is used at this time, esterification or ester-interchange reaction of the carboxylic acid or carboxylic ester can be carried out at the same time. When $R^{53}$ in compound [XII] is a lower alkyl group, compound [VIII] can be produced by carrying out the hydrolysis reaction described in Production Route 1.

PRODUCTION ROUTE 3

The step of producing compound [XIII] from compound [XI] via olefin isomerization can be carried out, for example, by treating compound [XI] with hydrogen and a hydrogenation catalyst such as palladium-carbon, platinum oxide or Raney nickel in a solvent which does not adversely affect the reaction, for example methanol, ethanol, acetic acid, ethyl acetate or a mixture of these, at 0° to 50° C. under a hydrogen pressure of 1 to 4 atmospheres for 30 minutes to 8 hours. Where one or both of $R^{20}$ and $R^{50}$ in compound [XIII] are lower alkyl groups, compound [VIII] can be produced by de-esterifying the carboxylic ester and/or the phosphinic ester as described above.

PRODUCTION ROUTE 4

The step of producing compounds [X] and [XV], which are the Z and E isomers of olefin, from compound [XIV] and compound [V] can be carried out by performing the reaction in the presence of a strong base such as sodium ethoxide, potassium tert-butoxide or sodium hydride in a solvent which does not adversely affect the reaction at −20° C. to the boiling point of the solvent for 30 minutes to 7 days. Examples of the solvent are alcohols such as ethanol and tert-butyl alcohol; ethers such as diethyl ether and tetrahydrofuran; and mixtures of these. The amount of compound [V] used is 0.5 to 10 moles, preferably 0.8 to 1.2 moles, per mole of compound [XIV].

Compounds [X] and [XV] so produced can be isolated and purified by extraction, crystallization, column chromatography (e.g., silica gel), thin-layer chromatography, or a combination of these.

If compound [X] is treated under the hydrolysis conditions described in Production Route 1, compound [VIII] is obtained. When compound [XV] is treated under either EZ isomerization conditions described in Production Route 2 or 3, followed by the hydrolysis, compound [VIII] is obtained. Compound [VIII] can also be obtained by treating a mixture of compounds [X] and [XV] without isolation under either EZ isomerization conditions described in Production Route 2 or 3, followed by the hydrolysis or by first performing the hydrolysis and then treating the product under either olefin isomerization conditions.

Compound [XIV], the starting substance in Production Route 4, can be produced by known methods, for example, the methods described in A. N. Pudovik et al., Izv. Akad. Nauk S.S.S.R., Otd. Khim. Nauk 902 (1952); Chemical Abstracts, Vol. 47, 10469c (1953), and J. K. Thottathil, Tetrahedron Letters, vol. 25, page 4737 (1984).

PRODUCTION ROUTE 5

The step of producing compound [XVIII] from compound [XVI] and compound [XVII] can be carried out, for example, by performing the reaction in the presence of a base in a solvent which does not adversely affect the reaction at −20° C. to the boiling point of the solvent for 1 to 48 hours. Examples of the base are triethylamine, 1,8-diazabicyclo[5,4,0]-7-undecene, tetramethylammonium hydroxide, sodium hydroxide, potassium hydroxide, sodium carbonate, potassium carbonate, sodium methoxide, sodium ethoxide, potassium tert-butoxide, sodium hydride or butyl lithium. The solvent may be, for example, water, methanol, ethanol, isopropanol, tert-butyl alcohol, tetrahydrofuran, dioxane, acetonitrile, dimethylformamide, dimethyl sulfoxide, or a mixture of these.

The amount of compound [XVII] used is 0.5 to 10 moles, preferably 0.8 to 1.5 moles per mole of compound [XVI]. When in compound [XVIII], the configuration of the olefin is E or Z plus E, compound [XVIII] in which the configuration of the olefin is Z can be produced according to either method shown in Production Route 2 or 3. Where one or both of $R^{20}$ and $R^{50}$ are lower alkyl groups, the above compound can be subjected to de-esterification conditions shown in Production Route 1.

PRODUCTION ROUTE 6

The step of producing compound [XX] from compound [XVI] and compound [XIX] can be carried out, for example, by performing the reaction in a solvent which does not adversely affect the reaction, for example water, methanol, ethanol, isopropanol, tert-butyl alcohol, tetrahydrofuran, dioxane, acetonitrile, dimethylformamide, dimethyl sulfoxide or a mixture of these, or in the absence of a solvent, at 0° to 200° C. for 1 hour to 7 days in the presence, as required, of a catalyst such as sodium iodide or potassium iodide. The amount of compound [XIX] used is 0.5 to 100 moles, preferably 1 to 20 moles, per mole of compound [XVI]. When in compound [XX], the configuration of the olefin is E or Z plus E, compound [XX] in which the olefin has a Z-configuration can be produced according to either method shown in Production Route 2 or 3. Where one or both of $R^{20}$ and $R^{50}$ are lower alkyl groups, the above compound can be subjected to de-esterification conditions shown in Production Route 1.

PRODUCTION ROUTE 7

The step of producing compound [XXII] by catalytic reduction of the double bond of compound [XXI] can be carried out by, for example, performing the reaction in the presence of a hydrogenation catalyst such as palladium-carbon, platinum oxide or Raney nickel in a solvent which does not adversely affect the reaction, such as methanol, ethanol, acetic acid, ethyl acetate or a mixture of these, at 0° to 50° C. under a hydrogen pressure of 1 to 4 atmospheres for 1 to 72 hours. When in compound [XXII], one or both $R^{20}$ and $R^{50}$ are lower alkyl groups, the compound can be subjected to de-esterification conditions shown in Production Route 1.

PRODUCTION ROUTE 8

The step of producing compound [XXV] from compound [XXIII] and an alcohol of the formula [XXIV] can be carried out, for example, by performing the reaction in the presence of an acid such as hydrochloric acid, hydrobromic acid, sulfuric acid, methanesulfonic acid or p-toluenesulfonic acid in a solvent which does not adversely affect the reaction, such as dichloromethane, dichloroethane, benzene, toluene or a mixture of these, or in the alcohol of formula [XXIV] as a solvent without using the above solvent, at room temperature to the boiling point of the solvent for 1 to 24 hours. Where $R^{23}$ is a lower alkyl group in compound [XXV], this compound can be subjected to de-esterification conditions shown in Production Route 1.

PRODUCTION ROUTE 9

The step of producing compound [XXVIII] from compound [XXVI] and compound [XXVII] can be carried out, for example, by performing the reaction in the presence of a base such as triethylamine, 1,8-diazabicyclo[5,4,0]-7-undecene, sodium hydroxide, potassium hydroxide, sodium carbonate, potassium carbonate or sodium hydride in a solvent which does not adversely affect the reaction, such as water, methanol, ethanol, acetonitrile, dimethylformamide, dimethyl sulfoxide, hexamethylphosphoramide or a mixture of these at 0° C. to the boiling pint of the solvent for 1 to 48 hours. It is also possible to treat compound [XXVI] with the above base to form a salt, isolating the salt, dissolving it in the above solvent, and treating it with a compound of formula [XXVII]. When $R^{20}$ in compound [XXVIII] is a lower alkyl group, this compound can be subjected to de-esterification conditions shown in Production Route 1.

As required, the compound of formula [I] may be converted into its pharmaceutically acceptable salt. For example, a disodium salt of the compound [I] can be obtained by adding 2 equivalents of an aqueous solution of sodium hydroxide to a solution of compound [I] in a lower alcohol such as methanol, ethanol or isopropanol, and collecting the precipitated crystals by filtration. Its calcium salt can be obtained by adding an aqueous solution of calcium chloride to an aqueous solution of the sodium salt and collecting the precipitated crystals by filtration.

The compound of formula [I] provided by this invention shows DHP-I inhibitory activity even in oral administration, and an excellent duration of blood level in vivo.

The following Pharmacological Test Examples demonstrate the pharmacological characteristics of the compound [I] of the present invention.

TEST COMPOUNDS (1) (Z)-2-(butylhydroxyphosphinoyl)methyl-3-cyclohexylpropenoic acid [Example 3 (b)]

(2) (Z)-3-cyclohexyl-2-(hydroxyisobutylphsophinoyl)-methylpropenoic acid [Example 5 (b)]

(3) (Z)-3-cyclohexyl-2-(hydroxyisopropylphosphinoyl)-methylpropenoic acid [Example 11 (c)]

(4) (Z)-3-cyclohexyl-2-(decylhydroxyphosphinoyl)methylpropenoic acid [Example 13 (c)]

(5) (Z)-3-cyclohexyl-2-(2,2-dimethycyclopropylhydroxyphosphinoyl)methylpropenoic acid [Example 14 (c)]

(6) (Z)-2-(hydroxisobutylphosphinoyl)methyl-2-ocetenoic acid [Example 16 (c)]

(7) (Z)-2-(hydroxyisobutylphosphinoyl)methyl-2-dodecenoic acid [Example 17 (c)]

(8) (Z)-2-(hydroxyisobutylphosphinoyl)methyl-4-methyl-2-pentenoic acid [Example 19 (c)]

(9) (Z)-2-(hydroxyisobutylphosphinoyl)methyl-5-methyl-2-hexenoic acid [Example 20 (c)]

(10) (Z)-3-cyclopropyl-2-(hydroxyisobutylphosphinoyl)methylpropenoic acid [Example 21 (c)]

(11) (Z)-2-hydroxyisobutylphosphinoyl)methyl-5-phenyl-2-pentenoic acid [Example 22 (c)]

(12) (Z)-6-chloro-2-(hydroxyisobutylphosphinoyl)-methyl-2-hexenoic acid [Example 23 (c)]
(13) (Z)-8-chloro-2-(hydroxyisobutylphosphinoyl)-methyl-2-octenoic acid [Example 24 (c)]
(14) (Z)-2-(hydroxyisobutylphosphinoyl)methyl-2-heptenedioic acid [Example 25 (c)]
(15) (Z)-3-cyclopropyl-2-(2,2-dimethycyclopropylhydroxyphosphinoyl)methylpropenoic acid [Example 26 (c)]
(16) (Z)-2-(cyclohexylmethylhydroxyphosphinoyl)-methyl-3-cyclopropylpropenoic acid [Example 27 (b)]
(17) (Z)-3-cyclohexyl-2-(cyclopentylmethylhydroxyphosphinoyl)methylpropenoic acid [Example 29 (b)]
(18) (Z)-2-(hydroxyisobutylphosphinoyl)methyl-6-phenylthio-2-hexenoic acid [Example 42 (b)]
(19) (Z)-2-(hydroxyisobutylphosphinoyl)methyl-6-(1,2,3-triazol-4-yl)thio-2-hexenoic acid [Example 43 (b)]
(20) (Z)-8-carboxymethylthio-2-(hydroxyisobutylphosphinoyl)methyl-2-octenoic acid [Example 44 (a)]
(21) (Z)-2-(hydroxyisobutylphosphinoyl)methyl-8-methoxycarbonylmethylthio-2-octenoic acid [Example 44 (b)]
(22) (Z)-6-(3-hydroxy-2-pyridiyl)thio-2-(hydroxyisobutylphosphinoyl)methyl-2-hexenoic acid [Example 45 (b)]
(23) (Z)-6-[(L)-2-amino-2-carboxyethyl]thio-2-(hydroxyisobutylphosphinoyl)methyl-2-hexenoic acid [Example 46 (b)]
(24) (Z)-2-(hydroxyisobutylphosphinoyl)methyl-6-(1-methylimidazol-2-yl)thio-2-hexenoic acid [Example 49 (b)]
(25) (Z)-8-(3-hydroxy-2-pyridyl)thio-2-(hydroxyisobutylphosphinoyl)methyl-2-octenoic acid [Example 50 (b)]
(26) 2-(butylhydroxyphosphinoyl)methyl-3-cyclohexylpropionic acid [Example 35]
(27) (5-methyl-2-oxo-1,3-dioxol-4-yl)methyl (Z)-3-cyclohexyl-2-(hydroxyisobutylphosphinoyl)methyl-propenoate [Example 57]
(28) (Z)-3-cyclohexyl-2-(cyclohexylmethylhydroxyphosphinoyl)methylpropenoic acid [Example 4 (b)]
(29) (Z)-2-(hydroxyisobutylphosphinoyl)methyl-3-phenylpropenoic acid [Example 1 (b)]
(30) (Z)-2-(hydroxyisobutylphosphinoyl)methyl-2-butenoic acid [Example 15 (b)]
(31) (Z)-6-(2-hydroxyethyl)thio-2-(hydroxyisobutylphosphinoyl)methyl-2-hexenoic acid [Example 38]

TESTING PROCEDURE (1) Inhibitory activity on porcine kidney dehydropeptidase I (i) Purification of porcine dehydropeptidase I Frozen porcine kidney cortex was homogenized. Butanol (¼ volume) pre-cooled in a dry ice-acetone bath was added to the homogenate, and the mixture was stirred at 4° C. for 43 hours. The mixture was then dialyzed for one day and centrifuged at 3,000 g for 30 minutes. To the resulting supernatant was added ammonium sulfate. A precipitate at the salt concentration range between 50 and 75% was collected to give a crude enzyme preparation which was re-dissolved in a 50 mM MOPS buffer containing 0.5 M NaCl. The solution was charged on a cilastatin affinity column. Elution with a 50 mM MOPS buffer containing 0.5 M NaCN gave a purified enzyme preparation.

(ii) Measurement of inhibitory activity

The resulting enzyme preparation (3 mU) and an inhibitor were pre-incubated at 37° C. for 3 hours in 2.7 ml of a 50 mM MOPS buffer (pH 7.4), and then 2.475 ml of the mixture was transferred into a cuvette. As a substrate, 25 microliters of a 5 mM glycyldehydrophenylalanine solution in a 50 mM MOPS buffer (pH 7.4) was added to start an enzymic reaction. The reaction was carried out at 37° C. in a spectrophotometer fitted with a constant-emperature device, and a decrease of the absorbance at 275 nm during a period of 5 minutes was measured. By comparison with the value of a control run which did not employ any inhibitor, a percent inhibition was determined at each of the inhibitor concentrations. An $IC_{50}$ value was calculated from the percent inhibition data. The results are shown in Table 1.

One unit (U) is defined as the amount of the enzyme which hydrolyzes 1 micromole of the substrate (glycyl-dehydrophenylalanine) per minute at a substrate concentration of 0.05 mM at 37° C. in a 50 mM MOPS buffer (pH 7.4).

TABLE 1

| Inhibitory activity on porcine DHP-I | |
|---|---|
| Test compound No. | Concentration producing 50% inhibition ($IC_{50}$, M) |
| 1 | $3.8 \times 10^{-8}$ |
| 2 | $1.3 \times 10^{-8}$ |
| 3 | $4.2 \times 10^{-8}$ |
| 4 | $6.8 \times 10^{-8}$ |
| 5 | $8.2 \times 10^{-9}$ |
| 6 | $4.6 \times 10^{-8}$ |
| 7 | $2.7 \times 10^{-8}$ |
| 8 | $1.6 \times 10^{-8}$ |
| 9 | $1.5 \times 10^{-8}$ |
| 10 | $1.4 \times 10^{-8}$ |
| 11 | $5.7 \times 10^{-8}$ |
| 12 | $5.1 \times 10^{-8}$ |
| 13 | $4.4 \times 10^{-8}$ |
| 14 | $1.1 \times 10^{-8}$ |
| 15 | $6.3 \times 10^{-9}$ |
| 16 | $4.1 \times 10^{-8}$ |
| 17 | $1.8 \times 10^{-8}$ |
| 18 | $2.1 \times 10^{-8}$ |
| 19 | $2.5 \times 10^{-8}$ |
| 20 | $2.2 \times 10^{-8}$ |
| 21 | $3.1 \times 10^{-8}$ |
| 22 | $2.3 \times 10^{-8}$ |
| 23 | $4.8 \times 10^{-8}$ |
| 24 | $4.8 \times 10^{-8}$ |
| 25 | $1.9 \times 10^{-8}$ |
| 26 | $2.8 \times 10^{-8}$ |
| 27 | $1.5 \times 10^{-4}$ |
| 28 | $5.0 \times 10^{-8}$ |
| 29 | $6.0 \times 10^{-8}$ |
| 30 | $7.5 \times 10^{-8}$ |
| 31 | $6.4 \times 10^{-8}$ |
| Cilastatin (control) | $1.0 \times 10^{-7}$ |

The above test results show that the compounds of this invention have strong DHP-I inhibitory activity. Accordingly, they are considered as useful in combination with carbapenem or penem antibiotics, for the purpose of preventing the in vivo inactivation of the antibiotics by DHP-I, especially in the kidney.

(2) Effect on urinary recovery of carbapenem

Male SD rats (8 week-old) were grouped, three per group. Imipenem alone was intravenously administered in a dose of 10 mg/kg to a first group. A combination of imipenem (10 mg/kg) and the compound No. 2 (10 mg/kg) was intravenously administered to a second group. To a third group, the compound No. 2 was administered orally in a dose of 10 mg/kg, and thirty minutes later, imipenem was intravenously administered in a dose of 10 mg/kg. For comparison, a combination of imipenem (10 mg/kg) and cilastatin (10 mg/kg) was intravenously administered to a fourth group.

Rat urine excreted during a period of up to 8 hours after the administration of imipenem was collected, and the concentration of imipenem in the urine collected was determined by the disc-late method using [Bacillus subtilis ATCC 12432. The urinary recovery of imipenem was calculated. The results are shown in Table 2.

TABLE 2

Effect on urinary recovery of imipenem

| Group | DPI-I inhibitor | Route | Urinary recovery of imipenem (%) Mean ± S.D. n = 3 |
|---|---|---|---|
| 1 | — | — | 29.6 ± 4.8 |
| 2 | Compound No. 2 (10 mg/kg) | iv | 95.3 ± 6.1 |
| 3 | Compound No. 2 (10 mg/kg) | po | 52.1 ± 4.9 |
| 4 (control) | Cilastatin (10 mg/kg) | iv | 85.9 ± 2.9 |

The above test results clearly show that the compound of this invention, in oral administration as well as in intravenous administration, markedly increased the urinary recovery of imipenem in rats. Accordingly, the compounds of this invention are considered as useful in combination with carbapenem or penem antibiotics.

(3) Protective action on nephrotoxicity induced by carbapenem antibiotics

Twelve male Japanese white rabbits (18 week-old; body weight 3.19–3.54 kg) were divided into three groups each consisting of 4 animals. Imipenem alone was administered in a dose of 150 mg/kg to a first group. To a second group, a combination of imipenem (150 mg/kg) and the compound No. 2 (150 mg/kg) was administered. To a third group as a control, sterilized physiological saline was administered. In all cases, the administration was effected through the auricular vein. Forty-eight hours later, a blood sample was taken from each of the animals, and the BUN and creatinine values were measured. The kidneys of the rabbits were taken and examined histopathologically. The results are shown in Table 3.

TABLE 3

Protective action on nephrotoxicity induced by imipenem

| Group | Imipenem (mg/kg) | Compound No. 2 (mg/kg) | BUN (mg/100 ml) | Creatinine (mg/ml) | Necrosis of the kidney tissue (#) |
|---|---|---|---|---|---|
| 1 | 150 | 0 | 70.8* | 7.13* | Marked (4/4) |
| 2 | 150 | 150 | 16.2 | 1.49 | None (0/4) |
| 3 (control) | 0 | 0 | 13.6 | 1.38 | None (0/4) |

: The parenthesized figures show the number of rabbits which necrotized at the kidney tissue versus the number of rabbits tested.
*P ≤ 0.05

The above test results clearly show that the compound of this invention markedly prevented nephrotoxicity induced by a high dose of imipenem in rabbits. Accordingly, the compound of this invention is considered as useful in combination with carbapenem antibiotics.

(4) Pharmacokinetic evaluations (4-a) Test in rats

Male SD rats (g week-old) were divided into groups each consisting of three animals. The compound Nos. 2, 5, 10, 14, 17, 23 and 28 were intravenously administered respectively to a first, a second, a third, a fourth, a fifth, a sixth and a 7th group each in a dose of 10 mg/kg. On the other hand, the compound Nos. 2, 5, 10, 17, 28 and 27 were orally administered respectively to an 8th, a 9 th, a 10th, a 11 th, a 12th and a 13th group in a dose of 10 mg/kg (in the case of the compound No. 27, 10 mg/kg equivalent to the compound No. 2 which is the free acid of the ester No. 27). Furthermore, cilastatin was intravenously administered to a 14th group as a control group.

Plasma samples were taken periodically from the carotid artery through a cannula inserted into it at the points of 1/12, ¼, ½, 1, 2, 4, 6, 8 and 24 hours after the administration. The plasma concentration of each compound was measured by an enzymic reaction assay using porcine DHP-I. The results are shown in Table 4-a.

The plasma concentration of the compound No. 27 was calculated as that of the free acid (the compound No. 2). The area under the curve (AUC) of the plasma concentration was determined according to the trapezoidal rule.

TABLE 4-a

| | | | Plasma concentration in rats (μg/ml) | | | | | | | | | |
|---|---|---|---|---|---|---|---|---|---|---|---|---|
| | | | Time (hours) after administration | | | | | | | | | AUC |
| Group | Test compound | Route | 1/12 | ¼ | ½ | 1 | 2 | 4 | 6 | 8 | 24 | (μg · hr · ml$^{-1}$) |
| 1 | Compound No. 2 | iv | 84.9 | 60.7 | 53.7 | 42.2 | 21.8 | 10.5 | 5.4 | 2.5 | N.D. | 162.2 |
| 2 | Compound No. 5 | iv | 51.9 | 49.4 | 36.2 | 24.4 | 11.9 | 4.7 | 1.7 | 0.9 | 0.1 | 88.2 |
| 3 | Compound No. 10 | iv | 40.8 | 26.5 | 21.7 | 12.8 | 5.2 | 1.1 | 0.2 | 0.2 | N.D. | 40.6 |
| 4 | Compound No. 14 | iv | 28.0 | 11.3 | 4.6 | 1.4 | 0.3 | 0.1 | N.D. | — | — | 9.3 |
| 5 | Compound No. 17 | iv | 86.7 | 74.7 | 55.0 | 38.0 | 25.2 | 14.8 | 10.8 | 6.4 | 0.5 | 226.1 |
| 6 | Compound No. 23 | iv | 28.7 | 21.0 | 13.9 | 4.2 | 0.9 | 0.1 | N.D. | — | — | 17.9 |
| 7 | Compound No. 28 | iv | 58.1 | 40.6 | 30.4 | 18.3 | 11.7 | 4.8 | 2.3 | 1.0 | 0.1 | 82.4 |
| 8 | Compound No. 2 | po | 3.3 | 6.6 | 6.8 | 5.4 | 3.8 | 2.1 | 1.2 | 0.4 | N.D. | 24.3 |
| 9 | Compound No. 5 | po | 2.5 | 4.7 | 6.4 | 5.3 | 3.4 | 2.4 | 1.1 | 0.3 | N.D. | 22.5 |
| 10 | Compound No. 10 | po | 0.5 | 1.1 | 1.4 | 1.2 | 0.8 | 0.3 | 0.2 | N.D. | — | 3.9 |
| 11 | Compound No. 17 | po | 0.5 | 4.1 | 5.0 | 5.0 | 3.2 | 2.1 | 1.0 | 0.1 | N.D. | 18.4 |
| 12 | Compound No. 28 | po | 1.3 | 3.1 | 3.4 | 2.5 | 3.0 | 1.9 | 1.1 | 0.5 | N.D. | 19.0 |
| 13 | Compound No. 27 | po | 1.5 | 10.1 | 13.3 | 11.5 | 9.3 | 4.6 | 2.6 | 1.4 | N.D. | 56.9 |
| 14 | Cilastatin (control) | iv | 46.9 | 18.8 | 5.8 | N.D. | — | — | — | — | — | 12.0 |

N.D.: below the detection limit

The test results clearly show that the compounds of this invention have a very long duration of blood level as compared with cilastatin, and that unlike cilastatin which is not orally absorbable, the compounds of this invention themselves have good oral absorbability. By converting the compound of this invention into a prodrug, it is likely to gain a further increase in oral absorbability. For example, the compound No. 27, which is a prodrug of the compound No. 2, shows better oral absorbability than the compound No. 2.

(4-b) Test in dogs

Male beagle dogs (14 month-old) were divided into groups each having three animals. The compound No. 2 was administered intravenously to a first group in a dose of 10 mg/kg. The compound No. 2 was orally administered to a second group in a dose of 10 mg/kg. Then at the points of 1/12, ¼, ½, 1, 2, 4, 6, 8, 24 and 48 hours after the administration, plasma samples were taken periodically from the cephalic vein, and the plasma concentrations of the compounds were measured by an enzyme assay using porcine DHP-I. The results are shown in Table 4-b. The area under the curve (AUC) of the plasma level was determined according to the trapezoidal rule.

TABLE 4-b

| Time after administration (hr) | Plasma concentration in dogs (μg/ml) | |
|---|---|---|
| | Route | |
| | iv | po |
| 1/12 | 87.3 | 0.5 |
| ¼ | 71.0 | 3.0 |
| ½ | 52.2 | 5.8 |
| 1 | 40.8 | 9.6 |
| 2 | 24.5 | 7.8 |
| 4 | 6.7 | 3.1 |
| 6 | 2.4 | 1.6 |
| 8 | 1.2 | 0.7 |
| 24 | 0.1 | 0.7 |
| 48 | N.D. | N.D. |
| AUC (μg · hr · ml$^{-1}$) | 143.6 | 51.5 |

N.D.: below the detection limit.

It is clear from the test results that the compound of this invention has long duration and good oral absorbability in dogs as in rats.

(5) Acute toxicity test in mice

Male ddY mice (4 week-old; body weight 24–26 g) were divided into groups each consisting of 5 animals. The compound No. 2 was intravenously administered to a first group in a dose of 2,000 mg/kg. The compound No. 2 was orally administered to a second group in a dose of 4,000 mg/kg. After the administration, the incidence of death was observed over 7 days after the administration, and the results are shown in Table 5.

TABLE 5

| | Acute toxicity in mice | |
|---|---|---|
| Route | Dose of compound No. 2 (mg/kg) | Mortality (#) |
| i.v. | 2,000 | 0/5 |
| p.o. | 4,000 | 0/5 |

: The figures show the number of dead mice versus the number of mice tested.

The above test results clearly show that the compound of the present invention has very low toxicity.

The compound of formula [I] provided by this invention, in combination with a carbapenem or penem antibiotic, is used as a therapeutic agent for bacterial infections in mammals including man. The compound [I] and the carbapenem or penem antibiotic are used separately or in combination, and in either case, can be formulated as required into an orally or parenterally administrable preparation.

Examples of orally administrable preparations are tablets, granules, capsules, syrups, suspensions and a mixture for internal use. In the formulation of these preparations, adjuvants suitable for the respective drug forms can be used. There can be used, for example, vehicles such as lactose, sucrose, glucose, starch and crystalline cellulose; binders such as methylcellulose, hydroxypropylcellulose, gum arabic and gelatin; disintegrants such as calcium carboxymethylcellulose and starch; lubricants such as magnesium stearate, talc and silicic anhydride; emulsifiers such as gum arabic, carboxymethylcellulose, glycerin fatty acid esters and sodium lauryl sulfate; suspending agents; dispersants; solubilizers; corrigents; pH adjusters; stabilizers; preservatives; and coloring agents.

Examples of the parenterally administrable preparations are injectable preparations such as intravenously or intramuscularly administrable preparations.

The injectable preparations can take the form of a suspension, solution or emulsion in an oily or aqueous vehicle.

Suitable adjuvants can be used in formulating these injectable preparations. Examples of such adjuvants include isotonizing agents such as sodium chloride, glycerin and glucose; buffers such as tartaric acid, sodium acetate, sodium hydrogen phosphate, sodium carbonate and sodium hydrogen carbonate; suspending agents such as gum arabic, sodium alginate, carboxymethylcellulose and methylcellulose; preservatives such as p-hydroxybenzoic acid esters (methyl, ethyl, or propyl ester), and benzyl alcohol; soothing agents; and solubilizers. The solvent that can be used to formulate the injectable preparations is, for example, physiological saline, distilled water for injection, sterilized purified water, propylene glycol, or a vegetable oil. The active component can be in the form of a powder for formulation of a liquid preparation such as an injectable preparation with water which is aseptic and contains no pyrogen.

In oral administration, the compound of the present invention is given in a dose of 1 to 500 mg/kg, preferably 1 to 100 mg/kg, per day once a day or in several portions a day. In parenteral administration, it is given in a dose of 1 to 200 mg/kg, preferably 1 to 100 mg/kg once a day or in several portions a day. These doses are tentative measures, and can be varied depending upon the properties of a carbapenem or penem antibiotic to be used in combination. Furthermore, the dose can be increased or decreased depending upon the severity, body weight, age, etc. of the patient.

The following Examples illustrate the present invention specifically. It should be understood however that the scope of the invention is not limited by these

EXAMPLE 1

Production of (Z)- and (E)-2-(hydroxyisobutylphosphinoyl)methyl-3-phenylpropenoic acid (a) Production of ethyl (Z)- and (E)-2-(ethoxyisobutylphosphinoyl)methyl-3-phenylpropenoate Under a nitrogen atmosphere, 7.3 ml (11 millimoles) of 1.5 M butyllithium-hexane was added dropwise to a solution of 1.5 ml (11 millimoles) of diisopropylamine in 20 ml of dry tetrahydrofuran. The mixture was cooled to −78° C. in a dry ice-methanol bath, and 1.50 g (10 millimoles) of ethyl isobutylphosphinate and then 2.46 g (10.4 millimoles) of ethyl 2-diethoxyphosphinoyl-propenoate were added. The mixture was stirred at 0° C. for 30 minutes. The mixture was cooled to −30° C., and 1.1 ml (11 millimoles) of benzaldehyde was added. The mixture was stirred at −30° C. for 3 hours, and overnight at room temperature. A saturated aqueous solution of ammonium chloride (50 ml) was added to the reaction mixture, and the mixture was extracted three times with 50 ml of ethyl acetate each time. The combined organic layers were washed with 20 ml of a saturated aqueous solution of sodium chloride and dried over anhydrous magnesium sulfate. The solvent was evaporated under reduced pressure, and the residue was purified by medium-pressure liquid chromatography [Lobar column (a product of E. Merck & Co.), size C, Lichroprep SI 60, ethyl acetate]. The first fraction was evaporated to give 1.00 g (yield 30%) of ethyl (Z)-2-(ethoxyisobutylphosphinoyl)methyl-3-phenylpropenoate as a colorless oil.

IR (neat, cm$^{-1}$) 2962, 1713, 1266, 1203, 1161, 1035, 957.

FAB-MS (m/e): 339 (M+H)$^+$.

$^1$H-NMR (CDCl$_3$, δ ppm): 1.01 (6H, dd, J=3.6 Hz, 6.4 Hz), 1.21 (3H, t, J=7.1 Hz), 1.36 (3H, t, J=7.0 Hz), 1.59–1.67 (2H, m), 2.02–2.10 (1H, m), 3.10–3.27 (2H, m), 3.84–4.14 (2H, m), 4.29 (2H, q, J=7.2 Hz), 7.33–7.43 (3H, m), 7.61 (2H, d, J=6.8 Hz), 7.83 (1H, d, J=4.9 Hz).

The second fraction was evaporated to give 0.74 g (yield 22%) of ethyl (E)-2-(ethoxyisobutylphosphinoyl)methyl-3-phenylpropenoate as a colorless oil.

IR (neat, cm$^{-1}$) 2962, 1719, 1230, 1161, 1035, 954.

FAB-MS (m/e): 339 (M+H)$^+$.

$^1$H-NMR (CDCl$_3$, δ ppm): 1.05–1.10 (9H, m), 1.30 (3H, t, J=7.1 Hz), 1.63–1.77 (2H, m), 2.04–2.21 (1H, m), 2.94–3.11 (2H, m), 3.98–4.18 (4H, m), 6.92 (1H, d, J=4.9 Hz), 7.26–7.44 (5H, m).

The structures of the (Z) and (E) isomers were determined by measuring the nuclear Overhauser effect (NOE) in $^1$H-NMR. Specifically, in the (E)-isomer [A], an NOE of +19.5% was observed between Hα (δ2.94–3.11 ppm, m) and Hβ (δ 6.92 ppm, d). On the other hand, in the (Z)-isomer [B], No NOE was observed between Hα, (δ3.10–3.27 ppm, m) and Hβ'' (δ 7.83 ppm, d).

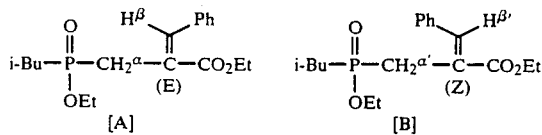

(b) Production of (Z)-2-(hydroxyisobutylphosphinoyl)-methyl-3-phenylpropenoic acid A 6 N aqueous solution of sodium hydroxide (3 ml) was added to a solution of 330 mg (1.0 millimole) of ethyl (Z)-2-(ethoxyisobutylphosphinoyl)methyl-3-phenylpropenoate in 6 ml of ethanol, and the mixture was heated under reflux for 8 hours. After the reaction mixture was allowed to cool, it was concentrated under reduced pressure. Water (10 ml) was added to the residue, and the mixture was made strongly acidic with hydrochloric acid. The mixture was extracted three times with 10 ml of ethyl acetate each time. The combined organic layers were washed with 10 ml of a saturated aqueous solution of sodium chloride, and dried over anhydrous magnesium sulfate. The solvent was evaporated under reduced pressure. The residue was recrystallized from ethyl acetate/hexane (2:1) to give 130 mg (yield of the captioned compound as colorless crystals.

m.p.: 114°–115° C.

IR (KBr, cm$^{-1}$): 2962, 1704, 1215, 1131, 966, 945.

FAB-MS (m/e): 283 (M+H)$^+$.

$^1$H-NMR (CD30D, δ ppm): 1.01 (6H, d, J=6.6 Hz), 1.74 (2H, dd, J=6.7 Hz, 13.2 Hz), 2.00–2.12 (1H, m) 3.15 (2H, d, J=17.3 Hz), 7.33–7.45 (3H, m), 7.63 (2H, d, J=7.4 Hz), 7.87 (1H, d, J=4.9 Hz).

Elemental analysis for $C_{14}H_{19}O_4P$:

Calculated: C 59.57%, H 6.79%.

Found: C 59.42%, H 6.82%.

(c) Production of (E)-2-(hydroxyisobutylphosphinoyl)-methyl-3-phenylpropenoic acid Ethyl (E)-2-(ethoxyisobutylphosphinoyl)methyl-phenylpropenoate (330 mg; 1.0 millimole) was hydrolyzed in a similar manner as in Example 1 (b), and recrystallized from ethyl acetate to give 130 mg (yield 47%) of the captioned compound.

m.p.: 130.5°–131.5° C.

IR (KBr, cm$^{31\ 1}$): 2956, 1698, 1245, 1122, 966, 948.

FAB-MS (m/e): 283 (M+H)$^+$ $^1$H-NMR (CD30D, δ ppm): 1.07 (6H, d, J=6.6 Hz), 1.74 (2H, dd, J=6.7 Hz, 13.5 Hz), 2.01–2.20 (1H, m), 2.97 (2H, d, J=17.1Hz), 6.89 (1H, d, J=5.2 Hz), 7.23–7.36 (5H, m).

Elemental analysis for $C_{14}H_{19}O_4P$:

Calculated: C 59.57%, H 6.79%.

Found: C 59.53%, H 6.84%.

EXAMPLE 2

Production of (Z)- and (E)-3-cyclohexyl-2-(ethylhydroxyphosphinoyl)methyl-propenoic acid (a) Production of ethyl (Z)- and (E)-3-cyclohexyl-2-(ethoxyethylphosphinoyl)methylpropenoate Under a nitrogen atmosphere, 0.23 g (10 millimoles) of metallic sodium was dissolved in 20 ml of dry ethanol. The solution was cooled to 0° C., and 1.22 g (10 millimoles) of ethyl ethylphosphinate and then 2.40 g (10 millimoles) of ethyl 2-diethoxyphosphinoylpropenoate were added. The mixture was stirred at 0° C. for 1 hour. Cyclohexanecarbaldehyde (1.20 ml; 9.9 millimoles) was added to the mixture, and the reaction was carried out at room temperature for 3 days. Fifty milliliters of a saturated aqueous solution of ammonium chloride was added to the reaction mixture, and the mixture was extracted three times with 50 ml of ethyl acetate each time. The organic layers were washed with 30 ml of a saturated aqueous solution of sodium chloride, and dried over anhydrous magnesium sulfate. The solvent was evaporated under reduced pressure, and the residue was purified by medium-pressure liquid chromatography Lobar column (a product of E. Merck & Co.), size C, Lichroprep SI 60, ethyl acetate. The first fraction was evaporated to give 0.33 g (yield 10%) of ethyl (Z)-3-cyclohexyl-2-(ethoxyethylphosphinoyl)methylpropenoate as a colorless oil.

IR (neat, cm$^{-1}$) 2932, 1713, 1278, 1227, 1170, 1044, 954.

FAB-MS (m/e): 317 (M+H)$^+$.

$^1$H-NMR (CDCl$_3$, δ ppm): 0.82–2.00 (21H, m), 2.10–2.60 (1H, m), 2.88 (2H, d, J=20 Hz), 3.76–4.35 (4H, m), 6.66 (1H, dd, J=6 Hz, 14 Hz).

The second fraction was evaporated to give 0.70 g (yield 22%) of ethyl (E)-3-cyclohexyl-2-(ethoxyethylphosphinoyl)methylpropenoate as a colorless oil.

IR (neat, cm$^{-1}$): 2932, 1719, 1248, 1218, 1179, 1044, 954.

FAB-MS (m/e): 317 (M+H)$^+$.

$^1$H-NMR (CDCl$_3$, δ ppm): 0.82–2.00 (21H, m), 2.55–3.20 (1H, m), 2.78 (2H, d, J=18 Hz), 3.77–4.37 (4H, m), 5.86 (1H, dd, J=6 Hz, 14 Hz).

(b) Production of dilithium salt of (Z)-3-cyclohexyl-2-(ethylhydroxyphosphinoyl)methylpropenoic acid A 1.5 N aqueous solution of lithium hydroxide (1.0 ml) was added to a solution of 205 mg (0.65 millimole) of ethyl (Z)-3-cyclohexyl-2-(ethoxyethylphosphinoyl)methylpropenoate in 7 ml of ethanol, and the mixture was heated under reflux for 4 hours. After cooling, the precipitated crystals were collected by filtration, and dried to give 78 mg (yield 44%) of the captioned compound as colorless crystals.

m.p.: >300° C.

IR (KBr, cm$^{-1}$): 2926, 1578, 1404, 1158, 1071, 1044.

FAB-MS (m/e): 273 (M+H)$^+$.

$^1$H-NMR (CD30D-D20, δ ppm): 0.80–1.82 (15H, m), 2.41–2.55 (1H, m), 2.71 (2H, d. J=18.3 Hz), 6.28 (1H, dd, J=4.7 Hz, 10.5 Hz).

Elemental analysis for C$_{12}$H$_{19}$Li$_2$O$_4$P:

Calculated: C 52.96%, H 7.04%.

Found: C 52.57%, H 6.99%.

(c) Production of dilithium salt of (E)-3-cyclohexyl-2-(ethylhydroxyphosphinoyl)methylpropenoic acid Ethyl (E)-3-cyclohexyl-2-(ethoxyethylphosphinoyl)methylpropenoate (161 mg; 0.51 millimoles) was treated in a similar manner as in Example 2 (b) to give 89 mg (yield 64%) of the captioned compound as colorless crystals.

m.p.: >300° C.

IR (KBr, cm$^{-1}$) 2932, 1557, 1452, 1143, 1128, 1047.

FAB-MS (m/e): 273 (M+H)$^+$.

$^1$H-NMR (CDOD3, δ ppm): 0.95–1.80 (15H, m), 2.45 (2H, d, J=15 Hz), 2.55–2.75 (1H, m), 5.18 (1H, dd, J=4.7 Hz, 9.5 Hz).

Elemental analysis for C$_{12}$H$_{19}$Li$_2$O$_4$P·0.5H$_2$O:

Calculated: C 51.27%, H 7.17%.

Found: C 51.22%, H 7.19%.

(d) Production of (Z)-3-cyclohexyl-2-(ethylhydroxyphosphinoyl)methylpropenoic acid A 1.5 N aqueous solution of lithium hydroxide (0.70 ml) was added to a solution of 100 mg (0.32 millimole) of ethyl (Z)-3-cyclohexyl-2-(ethoxyethylphosphinoyl)methylpropenoate in 3 ml of ethanol, and the mixture was heated under reflux for 6 hours. After cooling, 20 ml of water was added to dissolve the insoluble material, and the solution was extracted with 20 ml of ether. The aqueous layer was strongly acidified by adding 3N hydrochloric acid, and the solution was extracted three times with 20 ml of ether each time. The ether layers extracted under an acidic condition were combined, washed with 20 ml of a saturated aqueous solution of sodium chloride, and dried over anhydrous magnesium sulfate. The solvent was evaporated under reduced pressure. The residue was recrystallized from ethyl acetate/hexane (1:5) to give 55 mg (yield 66%) of the captioned compound as colorless crystals.

m.p.: 160°–162° C.

IR (KBr, cm$^1$): 2932, 1677, 1281, 1236, 1170, 960.

FAB-MS (m/e): 261 (M+H)$^+$.

$^1$H-NMR (CD$_3$OD, δ ppm): 1.10–1.82 (15H, m), 2.42–2.55 (1H, m), 2.92 (2H, d, J=17.1Hz), 6.76 (1H, dd, J=5.1Hz, 10.5 Hz).

Elemental analysis for C$_{12}$H$_{21}$O$_4$P:

Calculated: C 55.38%, H 8.13%.

Found: C 55.63%, H 8.21%.

(e) Production of (E)-3-cyclohexyl-2-(ethylhydroxyphosphinoyl)methylpropenoic acid Ethyl (E)-3-cyclohexyl-2-(ethoxyethylphosphinoyl)methylpropenoate (120 mg; 0.38 millimole) was treated in a similar manner as in Example 2 (d), and recrystallized from ethyl acetate/hexane (1:5) to give 59 mg (yield 61%) of the captioned compound as colorless crystals.

m.p.: 132°–133° C.

IR (KBr, cm$^{-1}$) 2926, 1683, 1278, 1170, 1101, 1008, 948.

FAB-MS (m/e): 261 (M+H)$^+$.

$^1$H-NMR (CD30D, δ ppm): 1.08–1.80 (15H, m), 2.81 (2H, d, J=17.1Hz), 2.95–3.15 (1H, m), 5.96 (1H, dd, J=4.8 Hz, 9.6 Hz).

Elemental analysis for C$_{12}$H$_{21}$O$_P$:

Calculated: C 55.38%, H 8.13%.

Found: C 55.59%, H 8.22%.

EXAMPLE 3

Production of (Z)- and (E)-2-(butylhydroxyphosphinoyl)methyl-3-cyclohexylpropenoic acid (a) Production of ethyl (Z)- and (E)-2-(butylethoxyphosphinoyl)methyl-3-cyclohexylpropenoate Under a nitrogen atmosphere, a solution of 0.75 g (5.0 millimoles) of ethyl butylphosphinate in 5 ml of dry tetrahydrofuran was added dropwise over 10 minutes at −70° C. to a solution of 3.30 ml (5.1 millimoles) of 1.55 N butyllithium-hexane in 5 ml of dry tetrahydrofuran. The mixture was stirred at this temperature for 10 minutes, and then heated to −50 ° C. A solution of 1.18 g (5.0 millimoles) of ethyl 2-diethoxyphosphinoylpropenoate in ml of dry tetrahydrofuran was added dropwise over 10 minutes. The mixture was then stirred at 0° C. for hour. The mixture was cooled to −25° C., and a solution of 0.56 g (5.0 millimoles) of cyclohexanecarbaldehyde in 5 ml of dry tetrahydrofuran was added, and the mixture was stirred at this temperature for 2 hours and then at room temperature for 1 hour. To the reaction mixture was added 100 ml of a saturated aqueous solution of ammonium chloride, and the mixture was extracted twice with 80 ml of ethyl acetate each time. The combined organic layers were dried over anhydrous magnesium sulfate, and the solvent was evaporated under reduced pressure. The residue was purified by medium-pressure liquid chromatography [Lobar column (a product of E. Merck & Co.), size C, Lichroprep SI 60, ethyl acetate)]. The first fraction was evaporated to give 0.38 g (yield 22%) of ethyl (Z)-2-(butylethoxyphosphinoyl)methyl-3-cyclohexylpropenoate as a colorless oil.

IR (neat, cm$^{-1}$): 2930, 1714, 1223, 1170, 1035, 953.

$^1$H-NMR (CDCl$_3$, δ ppm): 0.90 (3H, t, J=6 Hz), 1.09–2.00 (22H, m), 2.10–2.58 (1H, m), 2.94 (2H, d, J=17 Hz), 3.80–4.40 (4H, m), 6.72 (1H, dd, J=5 Hz, 10 Hz).

The second fraction was evaporated to give 0.14 g (yield 8%) of ethyl (E)-2-(butylethoxyphosphinoyl)methyl-3-cyclohexylpropenoate as a colorless oil.

IR (neat, cm$^{-1}$) 2937, 1724, 1220, 1177, 1038, 953.

$^1$H-NMR (CDCl$_3$, δ ppm): 0.90 (3H, t, J=6 Hz), 1.08-2.01 (22H, m), 2.83 (2H, d, J=16 Hz), 2.78-3.20 (1H, m), 3.79-4.41 (4H, m), 5.90 (1H, dd, J=4 Hz, 9 Hz).

(b) Production of (Z)-2-(butylhydroxyphosphinoyl)-methyl-3-cyclohexylpropenoic acid Ethyl (Z)-2-(butylethoxyphosphinoyl)methyl-3-cyclohexylpropenoate (360 mg; 1.05 millimoles) was treated in a similar manner as in Example 2 (d), and recrystallized from methanol/ethyl acetate/hexane to give 215 mg (yield 71%) of the captioned compound as colorless crystals.

m.p.: 146°-147° C.
IR (KBr, cm$^{-1}$): 2930, 1690, 1235, 1164, 963.
FAB-MS (m/e): 289 (M+H$^-$.
$^1$H-NMR (CD$_3$OD, δ ppm): 0.95 (3H, t, J=6 Hz), 1.07-2.00 (16H, m), 2.19-2.64 (1H, m), 2.90 (2H, d, J=17 Hz), 6.75 (1H, dd, J=5 Hz, 10 Hz).

Elemental analysis for C$_{14}$H$_{25}$O$_4$P:
Calculated: C 58.32%, H 8.74%.
Found: C 58.04%, H 8.83%.

(c) Production of (E)-2-(butylhydroxyphosphinoyl)-methyl-3-cyclohexylpropenoic acid A 1 N aqueous solution of lithium hydroxide (24 ml) was added to a solution of 470 mg (1.36 millimoles) of ethyl (E)-2-(butylethoxyphosphinoyl)methyl-3-cyclohexylpropenoate in 24 ml of acetone, and the mixture was heated under reflux for 24 hours. After cooling, acetone was evaporated under reduced pressure. The residue was made strongly acidic with 1 N sulfuric acid, and then the solution was extracted twice with 60 ml of ethyl acetate each time. The combined organic layers were dried over anhydrous magnesium sulfate, and the solvent was evaporated under reduced pressure. The residue was purified by preparative thin-layer chromatography [silica gel 60 F254 (a product of E. Merck & Co.), chloroform/methanol=3/1], and then recrystallized from methanol/ethyl acetate/hexane to give 52 mg (yield 13%) of the captioned compound as colorless crystals.

m.p.: 130°-132° C.
IR (KBr, cm$^{-1}$): 2930, 1687, 1225, 1150, 1030.
FAB-MS (m/e): 289 (M+H)$^+$.
$^1$H-NMR (CD$_3$OD, δ ppm): 0.92 (3H, t, J=6 Hz), 1.00-1.89 (16H, m), 2.48 (2H, d, J=15 Hz), 2.60-2.80 (1H, m), 5.60 (1H, dd, J=5 Hz, 10 Hz).

Elemental analysis for C$_{14}$H$_{25}$O$_4$P:
Calculated: C 58.32%, H 8.74%.
Found: C 57.74%, H 8.98%.

EXAMPLE 4

Production of (Z)-3-cyclohexyl-2-(cyclohexylmethylhydroxyphosphinoyl)methylpropenoic acid (a) Production of ethyl (Z)- and (E)-3-cyclohexyl-2-(cyclohexylmethylhydroxyphosphinoyl)methylpropenoate Under a nitrogen atmosphere, a solution of 200 mg (0.69 millimole) of ethyl 3-(cyclohexylmethylethoxyphosphinoyl)propionate, 70 mg (0.69 millimole) of cyclohexanecarbaldehyde and one drop of dry ethanol in 0.70 ml of dry benzene was added to a suspension of 30 mg (0.69 millimole) of sodium hydride (55% dispersion in mineral oil) in 1.0 ml of dry hexane, and the mixture was stirred at room temperature for 18 hours. Water (3 ml) and 0.70 ml of acetic acid were added to the reaction mixture, and the mixture was extracted three times with 10 ml of ether each time. The organic layers were combined and extracted four times with 10 ml of a 5% aqueous solution of sodium hydrogen carbonate each time. The aqueous layer was acidified with concentrated hydrochloric acid and extracted three times with 10 ml of chloroform each time. The combined organic layers were dried over anhydrous magnesium sulfate, and the solvent was evaporated under reduced pressure to give 130 mg of a colorless oil. From $^1$H-NMR, this oil was found to be a 1:3 mixture of ethyl (E)-3-cyclohexyl-2-(cyclohexylmethylhydroxyphosphinoyl)methylpropenoate and ethyl (Z)-3-cyclohexyl-2-(cyclohexylmethylhydroxyphosphinoyl)methylpropenoate. The total yield of the (E) and (Z) isomers was 53%.

(b) Production of (Z)-3-cyclohexyl-2-(cyclohexylmethylhydroxyphosphinoyl)methylpropenoic acid A 3:1 mixture of ethyl (Z)- and (E)-3-cyclohexyl-2-(cyclohexylmethylhydroxyphosphinoyl)methylpropenoate (90 mg; 0.25 millimole) was dissolved in 4.7 N hydrogen chloride-butyl acetate (1 ml), and the solution was heated at 100° C. in a sealed tube for 24 hours. After cooling, the solvent was evaporated under reduced pressure. The residue was dissolved in ethanol (0.32 ml), and 6 N sodium hydroxide (0.16 ml) was added. The mixture was heated under reflux for 3 hours. After cooling, 3 ml of water was added and hydrochloric acid was also added to acidify the mixture. The mixture was then extracted three times with 10 ml of ethyl acetate each time. The combined organic layers were washed with saturated aqueous solution of sodium chloride, and dried over anhydrous magnesium sulfate, and evaporated to dryness. The residue was recrystallized from ethyl acetate-hexane (1:4) to give 29 mg (yield 35%) of the captioned compound as colorless crystals.

m.p.: 170°-171.5° C.
IR (KBr, cm$^{-1}$): 2932, 2854, 1692, 1239, 1146, 954.
FAB-MS (m/e): 329 (M+H)$^+$.
$^1$H-NMR (CD$_3$OD, δ ppm): 1.01-1.39 (10H, m), 1.60-1.92 (13H, m), 2.46-2.50 (1H, m), 2.90 (2H, d, J=17.1 Hz), 6.74 (1H, dd, J=5.2 Hz, 10.5 Hz).

Elemental analysis for C$_{17}$H$_{29}$O$_4$P:
Calculated: C 62.18%, H 8.90%.
Found: C 61.43%, H 8.84%.

EXAMPLE 5

Production of (Z)- and (E)-3-cyclohexyl-2-(hydroxyisobutylphosphinoyl)methylpropenoic acid (a) Production of ethyl (Z)- and (E)-3-cyclohexyl-2-(ethoxyisobutylphosphinoyl)methylpropenoate By using cyclohexanecarbaldehyde instead of the benzaldehyde in Example 1 (a), the captioned compounds were obtained as a colorless oil.

Ethyl (Z)-3-cyclohexyl-2-(ethoxyisobutylphosphinoyl)methylpropenoate
IR (neat, cm$^{-1}$): 2992, 1710, 1260, 1167, 1029, 969.
$^1$H-NMR (CDCl$_3$, δ ppm): 1.04 (6H, dd, J=3.9 Hz, 6.6 Hz), 1.08-1.36 (11H, m) 1.60-1.76 (7H, m), 2.09-2.16 (1H, m), 2.39-2.42 (1H, m), 2.93 (2H, d, J=16.8 Hz), 3.96-4.13 (2H, m), 4.20 (2H, q, J=7.0 Hz), 6.71 (1H, dd, J=4.9 Hz, 10.5 Hz).

Ethyl (E)-3-cyclohexyl-2-(ethoxyisobutylphosphinoyl)methylpropenoate
IR (neat, cm$^{-1}$): 2986, 1716, 1251, 1179, 1038, 960.
$^1$H-NMR (CDCl$_3$, δ ppm): 1.03 (6H, d, J=7 Hz), 1.10-1.92 (18H, m), 1.90-2.25 (1H, m), 2.60-3.00 (1H, m), 2.78 (2H, d, J=16 Hz), 3.86–4.44 (4H, m), 5.88 (1H, dd, J=5 Hz, 9 Hz).

(b) Production of (Z)-3-cyclohexyl-2-(hydroxyisobutylphosphinoyl)methylpropenoic acid Ethyl (Z)-3-cyclohexyl-2-(ethoxyisobutylphosphinoyl)methylpropenoate was treated in a similar manner as in Example 2 (d), and recrystallized from ether-hexane to give the captioned compound as colorless crystals.

m.p.: 155°–156° C.

IR (KBr, cm$^{-1}$): 29.32, 1692, 1638, 1314, 1242, 1170, 1152, 957.

FAB-MS (m/e): 289 (M+H)$^+$.

$^1$H-NMR (CD$_3$OD, δ ppm): 1.05 (6h, d, J=6.6 Hz), 1.07–1.45 (5H, m), 1.64 (2H, dd, J=6.6 Hz, 12.9 Hz), 1.69–1.79 (5H, m), 2.01–2.19 (1H, m), 2.41–2.54 (1H, m), 2.90 (2H, d, J=17.1 Hz), 6.75 (1H, dd, J=5.1 Hz, 10.5 Hz).

Elemental analysis for C$_{14}$H$_{25}$O$_4$P:
Calculated: C 58.32%, H 8.74%, P 10.74%.
Found: C 58.32%, H 8.63%, P 10.9%.

When (Z)-3-cyclohexyl-2-(hydroxyisobutylphosphinoyl)methylpropenoic acid obtained as above was recrystallized from methanol-water, colorless crystals of a different crystal shape were obtained.

m.p.: 167°–169° C.

IR (KBr, cm$^{-1}$): 2932, 1716, 1644, 1263, 1248, 1125, 1053, 972.

($^1$H-NMR and FAB-MS data completely agreed with those of the crystals obtained above.)

(c) Production of (E)-3-cyclohexyl-2-(hydroxyisobutylphosphinoyl)methylpropenoic acid Ethyl (E)-3-cyclohexyl-2-(ethoxyisobutylphosphinoyl)methylpropenoate was treated in a similar manner as in Example 2 (d), and recrystallized from ether-hexane to give the captioned compound as colorless crystals.

m.p.: 162°–163° C.

IR (KBr, cm$^{-1}$): 2926, 1719, 1230, 1119, 954.

High-resolution FAB-MS
[m/e, for (C$_{14}$H$_{25}$O$_4$P+H)$^+$]:
Calculated: 289.1569.
Found: 289.1598.

$^1$H-NMR (CD$_3$OD, δ ppm): 1.04 (6H, d, J=6.6 Hz), 1.07–1.42 (6H, m), 1.62 (2H, dd, J=6.6 Hz), 13.2 Hz), 1.68–1.76 (4H, m), 1.97–2.16 (1H, m), 2.79 (2H, d, J=16.8 Hz), 2.94–3.10 (1H, m), 5.94 (1H, dd, J=4.8 Hz, 9.9 Hz).

EXAMPLE 6

Production of disodium salt of (Z)-3-cyclohexyl-2-(hydroxyisobutylphosphinoyl)methylpropenoic acid 6 N sodium hydroxide (24 ml; 144 millimoles) was added dropwise with ice cooling and stirring to a solution of 18.5 g (64.2 millimoles) of (Z)-3-cyclohexyl-2-(hydroxyisobutylphosphinoyl)methylpropenoic acid in 370 ml of methanol. The precipitated crystals were collected by filtration and dried to give 19.1 (yield 90%) of the captioned compound as colorless crystals.

m.p.: >300° C.

IR (KBr, cm$^{-1}$): 3292, 2926, 1551, 1401, 1140, 1038.

$^1$H-NMR (D$_2$O, δ ppm): 0.79 (6H, d, J=6.6 Hz), 0.85–1.17 (6H, m), 1.22 (2H, dd, J=6.7 Hz, 11.9 Hz), 1.44–1.52 (4H, m), 1.72–1.85 (1H, m), 2.18–2.25 (1H, m), 2.52 (2H, d, J=18.3 Hz), 6.00 (1H, dd, J=4.9 Hz, 10.1 Hz).

Elemental analysis for C$_{14}$H$_{23}$Na$_2$O$_4$P·0.85H$_2$O:
Calculated: C 48.38%, H 7.16%.
Found: C 48.54%, H 7.38%.

Water content measurement (by the Karl Fischer's method):
Calculated: 4.41%.
Found: 4.4%.

Na content measurement (flame spectrophotometry):
Calculated: 13.23%.
Found: 14.5%.

EXAMPLE 7

Production of calcium salt of (Z)-3-cyclohexyl-2-(hydroxyisobutylphosphinoyl)methylpropenoic acid A 3 M aqueous solution of calcium chloride (0.24 ml; 0.72 millimole) was added dropwise with ice cooling and stirring to a solution of 200 mg (0.58 millimole) of disodium salt of (Z)-3-cyclohexyl-2-(hydroxyisobutylphosphinoyl)methylpropenoic acid in 2.0 ml of water. The precipitated crystals were collected by filtration, and dried to give 200 mg (yield 99%) of the captioned compound as a white powder.

m.p.: >300° C.

IR (KBr, cm$^{-1}$): 3448, 2932, 1542, 1434, 1413, 1158, 1032.

Elemental analysis for C$_{14}$H$_{23}$CaO$_4$P·1.2H$_2$O:
Calculated: C 48.32%, H 7.36%.
Found: C 48.25%, H 7.19%.

Water content measurement (by the Karl Fischer'-method):
Calculated: 6.21%.
Found: 5.6%.

Ca content measurement (flame spectrophotometry):
Calculated: 11.52%.
Found: 12.0%.

EXAMPLE 8

Production of (Z)-3-cyclohexyl-2-(hydroxyisobutylphosphinoyl)methylpropenoic acid from ethyl (E)-3-cyclohexyl-2-(ethyoxyisobutylphosphinoyl)methylpropenoate A solution of 11.1 g (32.2 millimoles) of ethyl (E)-3-cyclohexyl-2-(ethoxyisobutylphosphinoyl)methylpropenoate in 100 ml of 4.3 N hydrogen chloride-butyl acetate was heated in a sealed tube for 48 hours. After cooling, the solvent was evaporated under reduced pressure to give a mixture of ethyl (Z)-3-cyclohexyl-2-(hydroxyisobutylphosphinoyl)methylpropenoate and ethyl (E)-3-cyclohexyl-2-(hydroxyisobutylphosphinoyl)methylpropenoate as a pale yellow oil. The (Z):(E) ratio determined by $^1$H-NMR was 90:10. The mixture was dissolved in a mixture of 32 ml of ethanol and 16 ml of 6 N sodium hydroxide, and heated under reflux for 3 hours. After cooling, the solvent was evaporated under reduced pressure. The residue was dissolved in 100 ml of water and made strongly acidic with hydrochloric acid, whereupon crystals precipitated. The crystals were collected by filtration and recrystallized from methanol-water (2:1) to give 4.6 g (yield 49%) of (Z)-3-cyclohexyl-2-(hydroxyisobutylphosphinoyl)methylpropenoic acid. Its melting point and IR and $^1$H-NMR were identical with those of the product obtained in Example 5 (b).

EXAMPLE 9

Production of (Z)-3-cyclohexyl-2-(hydroxyisobutylphosphinoyl)methylpropenoic acid from (E)-3-cyclohexyl-2-(hydroxyisobutylphosphinoyl)methylpropenoic acid A solution of 13 mg (0.045 millimole) of (E)-3-cyclohexyl-2-(hydroxyisobutylphosphinoyl)methylpropenoic acid in 0.13 ml of 4.3 N hydrogen chloride-butyl acetate was heated at 100° C. in a sealed tube for 24 hours. After cooling, the solvent was evaporated under reduced pressure. The residue was dissolved in 0.2 ml of ethanol, and 0.1 ml of 6 N sodium hydroxide was added. The mixture was heated under reflux for 1.5 hours. After cooling, 5 ml of water was added and hydrochloric acid was also added to acidify the mixture. The mixture was then extracted three times with 5 ml of ethyl acetate each time. The combined ethyl acetate layers were washed with 5 ml of a saturated aqueous solution of sodium chloride, and dried over anhydrous magnesium sulfate. The solvent was evaporated under reduced pressure. The residue was recrystallized from ethyl acetate/hexane to give 7 mg (yield 54%) of (Z)-3-cyclohexyl-2-(hydroxyisobutylphosphinoyl)methylpropenoic acid as colorless crystals. Its melting point and IR and $^1$H-NMR data were identical with those of the product obtained in Example 5 (b).

EXAMPLE 10

(a) Production of ethyl (Z)- and (E)-3-cyclohexyl-2-[ethoxy(4-methoxymethoxybutyl)phosphinoyl]methylpropenoate Ethyl 4-methoxymethoxybutylphosphinate (3.20 g; 15.2 millimoles) was treated in a similar manner as in Example 2 (a) to give a crude (E)/(Z) mixture. The crude product was purified by medium-pressure liquid chromatography [Lobar column (a product of E. Merck & Co.), size C, Lichroprep SI 60, ethyl acetate]. The first fraction was evaporated to give 1.60 g (yield 26%) of ethyl (Z)-3-cyclohexyl-2-[ethoxy(4-methoxymethoxybutyl)phosphinoyl]methylpropenoate as a colorless oil.

IR (neat, cm$^{-1}$): 2932, 1713, 1227, 1149, 1110, 1041, 957.

FAB-MS (m/e): 405 (M+H)$^+$.

$^1$H-NMR (CDCl$_3$, δ ppm): 1.14–1.36 (11H, m), 1.65–1.78 (11H, m), 2.40–2.43 (1H, m), 2.95 (2H, d, J=17.1 Hz), 3.34 (3H, s), 3.51–3.55 (2H, m), 4.00–4.12 (2H, m), 4.21 (2H, q, J=7.0 Hz), 4.61 (2H, s), 6.73 (1H, dd, J=4.9 Hz, 10.5 Hz).

The second fraction was evaporated to give 1.90 g (yield 31%) of ethyl (E)-3-cyclohexyl-2-[ethyoxy(4-methoxymethoxybutyl)phosphinoyl]methylpropenoate as a colorless oil.

IR (neat, cm$^{-1}$): 2932, 1719, 1218, 1164, 1110, 1038, 960.

FAB-MS (m/e): 405 (M+H)$^+$.

$^1$H-NMR (CDCl$_3$, δ ppm): 1.06–1.35 (11H, m), 1.65–1.74 (11H, m), 2.78–2.94 (3H, m), 3.35 (3H, s), 3.50–3.55 (2H, m), 3.98–4.13 (2H, m), 4.22 (2H, q, J=7.0 Hz), 4.60 (2H, s), 5.91 (1H, dd, J=4.8 Hz, 9.6 Hz).

(b) Production of (Z)-(3-cyclohexyl-2-[hydroxy(4-methoxymethoxybutyl)phosphinoyl]methylpropenoic acid A 6 N aqueous solution of sodium hydroxide (0.4 ml; 2.4 millimoles) was added to a solution of 200 mg (0.50 millimole) of ethyl (Z)-3-cyclohexyl-2-[ethoxy(4-methoxymethoxybutyl)phosphinoyl]methylpropenoate in 0.8 ml of ethanol, and the mixture was heated under reflux for 6 hours. After cooling, the reaction mixture was concentrated under reduced pressure. Water (10 ml) was added to the residue, and the mixture was acidified with hydrochloric acid and extracted three times with 15 ml of ethyl acetate each time. The combined organic layers were washed with 15 ml of a saturated aqueous solution of sodium chloride, and dried over anhydrous magnesium sulfate. The solvent was evaporated under reduced pressure, and the residue was recrystallized from ethyl acetate/hexane (1:1) to give 140 mg (yield 81%) of the captioned compound as colorless crystals.

m.p.: 112.5°–113.5° C.

IR (KBr, cm$^{-1}$): 2932, 1686, 1287, 1167, 1152, 1110, 1053, 960.

FAB-MS (m/e): 349 (M+H)$^+$.

$^1$H-NMR (CD$_3$OD, δ ppm): 1.14–1.40 (5H, m), 1.65–1.75 (11H, m), 2.46–2.50 (1H, m), 2.92 (2H, d, J=17.6 Hz), 3.33 (3H, s), 3.54 (2H, d, J=5.8 Hz), 4.59 (2H, s), 6.76 (1H, dd, J=5.0 Hz, 10.5 Hz).

Elemental analysis for C$_{16}$H$_{29}$O$_6$P:

Calculated: C 55.16%, H 8.31%.

Found: C 55.02%, H 8.31%.

(c) Production of (Z)-3-cyclohexyl-2-[hydroxy(4-hydroxybutyl)phosphinoyl]methylpropenoic acid Concentrated hydrochloric acid (0.2 ml) was added to a solution of 300 mg of (Z)-3-cyclohexyl-2-[hydroxy(4-methoxymethoxybutyl)phosphinoyl]methylpropenoic acid in 3 ml of methanol. The solution was stirred overnight at room temperature. The reaction mixture was concentrated under reduced pressure.

The residue was purified by medium-pressure liquid chromatography [Lobar column (a product of E. Merck & Co.), size B, Lichroprep RP-18, methanol-water (25:75)], and recrystallized from isopropyl ether-hexane (1:1) to give 87 mg (yield 33%) of the captioned compound as colorless crystals.

m.p.: 110°–111° C.

IR (KBr, cm$^{-1}$) 3454, 2932, 1689, 1278, 1245, 1149, 1029, 963.

FAB-MS (m/e): 305 (M+H)$^+$.

$^1$H-NMR (CD$_3$OD, δ ppm): 1.11–1.40 (5H, m), 1.59–1.77 (11H, m), 2.46–2.50 (1H, m), 2.92 (2H, d, J=17.3 Hz), 3.56 (2H, t, J=6.1 Hz), 6.76 (1H, dd, J=5.2 Hz, 10.5 Hz).

Elemental analysis for C$_{14}$H$_{25}$O$_5$P:

Calculated: C 55.25%, H 8.28%.

Found: C 55.10%, H 8.22%.

(d) Production of (Z)-2-[(4-chlorobutyl)hydroxyphosphinoyl)methyl-3-cyclohexylpropenoic acid Ethyl (Z)-3-cyclohexyl-2-[ethoxy(4-methoxymethoxybutyl)phosphinoyl)methylpropenoate (300 mg) was dissolved in a mixture of 3 ml of dioxane and 3 ml of concentrated hydrochloric acid. The solution was heated under reflux for 20 hours. After cooling, the reaction mixture was concentrated under reduced pressure and then water (10 ml) was added to the residue, and the mixture was extracted three times with 15 ml of ethyl acetate each time. The combined organic layers were dried over anhydrous magnesium sulfate, and the solvent was evaporated under reduced pressure. The residue was recrystallized from ethyl acetate-hexane (1:1) to give 72 mg (yield 30%) of the captioned compound as colorless crystals.

m.p.: 149.5°–151° C.

IR (KBr, cm⁻): 2932, 1716, 1275, 1230, 1119, 972.

FAB-MS (m/e): 323 (M+H)⁺.

¹H-NMR (CD₃OD, δ ppm): 1.14–1.40 (5H, m), 1.67–1.83 (11H, m), 2.45–2.50 (1H, m), 2.93 (2H, d, J=17.6 Hz), 3.58 (2H, t, J=6.2 Hz), 6.77 (1H, dd, J=5.2 Hz, 10.7 Hz).

Elemental analysis for $C_{14}H_{24}ClO_4P$:

Calculated: C 52.10%, H 7.49%.

Found: C 51.87%, H 7.44%.

EXAMPLES 11–30

The following compounds (Examples 11 to 30) were obtained in a similar manner as in Example 1.

EXAMPLE 11

(a) ethyl (Z)-3-cyclohexyl-2-(ethoxyisopropylphosphinoyl)methylpropenoate

Oil

IR (neat, cm⁻¹) 2932, 1713, 1278, 1227, 1167, 1044, 954.

FAB-MS (m/e): 331 (M+H)⁺.

¹H-NMR (CDCl₃, δ ppm): 1.06–1.40 (18H, m), 1.65–1.80 (4H, m), 1.84–2.03 (1H, m), 2.35–2.50 (1H, m), 2.90 (1H, dd, J=14.7 Hz, 14.7 Hz), 2.97 (1H, dd, J=14.7 Hz, 14.7 Hz), 3.94–4.11 (2H, m), 4.21 (2H, q, J=7.2 Hz), 6.74 (1H, dd, J=5.1 Hz, 10.5 Hz).

(b) ethyl (E)-3-cyclohexyl-2-(ethoxyisopropylphosphinoyl)methylpropenoate

Oil

IR (neat, cm⁻¹) 2932, 1722, 1218, 1032, 954.

FAB-MS (m/e): 331 (M+H)⁺.

¹H-NMR (CDCl₃, δ ppm): 1.01–1.40 (18H, m), 1.55–1.75 (4H, m), 1.83–1.95 (1H, m), 2.75–2.95 (1H, m), 2.83 (2H, d, J=14.4 Hz), 3.91–4.13 (2H, m), 4.23 (2H, q, J=7.2 Hz), 5.93 (1H, dd, J=4.5 Hz, 9.6 Hz).

(c) (Z)-3-cyclohexyl-2-(hydroxyisopropylphosphinoyl)methylpropenoic acid m.p.: 139.5°–141.5° C.

IR (KBr, cm⁻¹): 3412, 2926, 1713, 1149, 1119, 966.

FAB-MS (m/e): 275 (M+H)⁺.

¹H-NMR (CD₃OD, δ ppm); 1.10–1.43 (6H, m), 1.19 (6H, dd, J=7.2 Hz, 17.1 Hz), 1.65–1.80 (4H, m), 1.83–1.96 (1H,m), 2.42–2.55 (1H, m), 2.92 (2H, d, J=15.9 Hz), 6.76 (1H, dd, J=4.8 Hz, 10.5 Hz).

Elemental analysis for $C_{13}H_{23}O_4P$:

Calculated: C 56.92%, H 8.45%.

Found: C 56.89%, H 8.57%.

(d) (E)-3-cyclohexyl-2-(hydroxy-isopropylphosphinoyl)methylpropenoic acid m.p.: 144.5°–146.5° C.

IR (KBr, cm⁻¹): 3040, 2920, 1725, 1197, 1176, 1122, 954.

FAB-MS (m/e): 275 (M+H)⁺.

¹H-NMR (CD₃OD, δ ppm): 1.05–1.40 (6H, m), (4H, m), 1.83–1.97 (1H, m), 2.82 (2H, d, J=16.2 Hz), 2.96–3.10 (1H, m), 5.96 (1H, dd, J=4.2 Hz, 9.9 Hz).

Elemental analysis for $C_{13}H_{23}O_4P$:

Calculated: C 56.92%, H 8.45%.

Found: C 56.84%, H 8.98%.

EXAMPLE 12

(a) ethyl (Z)-3-cyclohexyl-2-(ethoxyhexylphosphinoyl)methylpropenoate

Oil

IR (neat, cm⁻¹): 2926, 1713, 1260, 1227, 1173, 1038, 954.

FAB-MS (m/e): 373 (M+H)⁺.

¹H-NMR (CDCl₃, δ ppm): 0.88 (3H, t, J=6.6 Hz), 1.05–1.78 (26H, m), 2.34–2.47 (1H, m), 2.95 (2H, d, J=17.1 Hz), 3.98–4.10 (2H, m), 4.21 (2H, q, J=7.2 Hz), 6.73 (1H, dd, J=4.8 Hz, 10.5 Hz).

(b) ethyl (E)-3-cyclohexyl-2-(ethoxyhexylphosphinoyl)methylpropenoate

Oil

IR (neat, cm⁻¹) 2926, 1719, 1248, 1215, 1179, 1038, 954.

FAB-MS (m/e): 373 (M+H)⁺.

¹H-NMR (CDCl₃, δ ppm): 0.88 (3H, t, J=6.6 Hz), 1.00–1.76 (20H, m), 1.28 (3H, t, J=6.9 Hz), 1.33 (3H, t, J=6.9 Hz), 2.71–2.95 (3H, m), 3.95–4.10 (2H, m), 4.22 (2H, q, J=6.9 Hz), 5.90 (1H, dd, J=4.5 Hz, 9.9 Hz).

(c) (Z)-3-cyclohexyl-2-(hexylhydroxyphosphinoyl)methylpropenoic acid m.p. 152.5°–155° C.

IR (KBr, cm⁻¹): 2926, 1689, 1287, 1167, 1149, 960.

FAB-MS (m/e): 317 (M+H)⁺.

¹H-NMR (CD₃OD, δ ppm): 0.91 (3H, t, J=6.9 Hz), 1.12–1.80 {20H, m), 2.40–2.56 (1H, m), 2.91 (2H, d, J=17.7 Hz}, 6.75 (1H, dd, J=5.4 Hz, 10.8 Hz).

Elemental analysis for $C_{16}H_{29}O_4P$:

Calculated: C 60.74%, H 9.24%.

Found: C 60.57%, H 9.63%.

(d) (E)-3-cyclohexyl-2-(hexylhydroxyphosphinoyl)methylpropenoic acid m.p.: 121°–123° C.

IR (KBr, cm⁻¹) 2926, 1716, 1230, 1182, 1146, 1116, 972.

FAB-MS (m/e): 317 (M+H)⁺.

¹H-NMR (CD₃OD, δ ppm): 0.91 (3H, t, J=6.9 Hz), 1.06–1.80 (20H, m), 2.80 (2H, d, J=17.4 Hz), 2.95–3.10 (1H, m), 5.95 (1H, dd, J=5.1 Hz, 9.9 Hz).

Elemental analysis for $C_{16}H_{29}O_4P$:

Calculated: C 60.74%, H 9.24%.

Found: C 60.68%, H 9.43%.

EXAMPLE 13

(a) ethyl (Z)-3-cyclohexyl-2-(decylethoxyphosphinoyl)methylpropenoate

Oil

IR (neat, cm⁻¹) 2930, 1716, 1305, 1230, 1176, 1043, 958.

FAB-MS (m/e): 429 (M+H)⁺.

¹H-NMR (CDCl₃, δ ppm): 0.86 (3H, t, J=7.2 Hz), 1.02–1.78 (34H, m), 2.32–2.46 (1H, m), 2.92 (2H, d, J=17.1 Hz), 3.93–4.08 (2H, m), 4.18 (2H, q, J=7.0 Hz), 6.70 (1H, dd, J=4.6 Hz, 9.4 Hz).

(b) ethyl (E)-3-cyclohexyl-2-(decylethoxyphosphinoyl)methylpropenoate

Oil

IR (neat, cm⁻¹) 2925, 1722, 1213, 1036, 955.

FAB-MS (m/e): 429 (M+H)⁺.

¹H-NMR (CDCl₃, δ ppm): 0.86 (3H, t, J=7.2 Hz), 0.99–1.78 (34H, m), 2.71–2.97 (3H, m), 3.91–4.11 (2H, m), 4.20 (2H, q, J=7.1 Hz), 5.88 (1H, dd, J=4.6 Hz, 9.6 Hz).

(c) (Z)-3-cyclohexyl-2-(decylhydroxyphosphinoyl)methylpropenoic acid m.p.: 132.5°–133.5° C.

IR (KBr, cm⁻¹) 2920, 1689, 1162, 1144, 960.

FAB-MS (m/e): 373 (M+H)⁺.

¹H-NMR (CD₃OD, δ ppm): 0.90 (3H, t, J=6.8 Hz), 1.05–1.87 (28H, m), 2.40–2.56 (1H, m), 2.91 (2H, d, J=17.6 Hz), 6.75 (1H, dd, J=4.8 Hz, 10.6 Hz).

Elemental analysis for $C_{20}H_{37}O_4P$:

Calculated: C 64.49%, H 10.01%.

Found: C 64.01%, H 10.23%.

(d) (E)-3-cyclohexyl-2-(decylhydroxyphosphinoyl)methylpropenoic acid
m.p.: 111.0°–112.0° C.
IR (KBr, cm$^{-1}$) 2930, 1690, 1235, 1100, 986.
FAB-MS (m/e): 373 (M+H)$^+$.
$^1$H-NMR (CD$_3$OD, δ ppm): 0.89 (3H, t, J=6.7 Hz), 1.02–1.81 (28H, m), 2.80 (2H, d, J=17.6 Hz), 2.96–3 11 1.03 (6H, d, J=6.5 Hz), 1.62 (2H, dd, J=6.5 Hz, 13.0
Elemental analysis for C$_{20}$H$_{37}$O$_4$P:
Calculated: C 64.49%, H 10.01%.
Found: C 64.31%, H 10.01%.

EXAMPLE 14

(a) ethyl (Z)-3-cyclohexyl-2-(2,2-dimethylcyclopropyl)ethoxyphosphinoylmethylpropenoate
Oil
IR (neat, cm$^{-1}$) 2932, 2854, 1713, 1647, 1227, 1164, 948.
FAB-MS (m/e): 357 (M+H)$^+$.
$^1$H-NMR (CDCl$_3$, δ ppm): 0.49–1.08 (3H, m), 1.10–1.80 (22H, m), 2.40–2.60 (1H, m), 2.94–3.12 (2H. m), 4.00–4.17 (4H, m), 6.69–6.80 (1H, m).

(b) ethyl (E)-3-cyclohexyl-2-(2,2-dimethylcyclopropyl)ethoxyphosphinoyl]methylpropenoate
Oil
IR (neat, cm$^{-1}$) 2926, 2854, 1719, 1215, 1167, 972.
FAB-MS (m/e): 357 (M+H)$^+$.
H-NMR (CDCl$_3$, δ ppm): 0.45–1.05 (3H, m), 1.10–1.80 (22H, m), 2.75–3.05 (3H, m), 4.00–4.30 (4H, m), 5.94 (1H, dd, J=4.8 Hz, 9.6 Hz).

(c) (Z)-3-cyclohexyl-2-(2,2-dimethylcyclopropyl)hydroxyphosphinoyl)methylpropenoic acid
m.p.: 169°–174° C.
IR (KBr, cm$^{-}$): 2932, 1692, 1245, 1161, 951.
FAB-MS (m/e): 301 (M+H)$^+$.
$^1$H-NMR (CD$_3$OD, δ ppm). 0.60–1.00 (3H, m) 1.10–1.48 (5H, m), 1.11 (3H, d, J=2.4 Hz), 1.30 (3H, s), 1.64–1.81 (5H, m), 2.45–2.60 (1H, m), 2.94 (2H, d, J=18.9 Hz), 6.72 (1H, dd, J=5.1 Hz, 10.5 Hz).
Elemental analysis for C$_{15}$H$_{25}$O$_4$P:
Calculated: C 59.99%, H 8.39%.
Found: C 59.62%, H 8.31%.

(d) disodium salt of (Z)-3-cyclohexyl-2-(2,2-dimethylcyclopropyl)hydroxyphosphinoyl)methylpropenoic acid
m.p.: >300° C.
IR (KBr, cm$^{-1}$) 3382, 2926, 1560, 1452, 1416, 1140, 1068.
FAB-MS (m/e): 345 (M+H)$^+$.
$^1$H-NMR (D$_2$O, δ ppm): 0.37–0.50 (3H, m), 1.10–1.40 (5H, m), 1.04 (3H, s), 1.21 (3H, s), 1.50–1.80 (5H, m), 2.35–2.50 (1H, m), 2.74 (2H, d, J=18.9 Hz), 6.16 (1H, dd, J=5.1 Hz, 9.6 Hz).
Elemental analysis for C$_{15}$H$_{23}$Na$_2$O$_4$P·½H$_2$O:
Calculated: C 51.43%, H 6.81%.
Found: C 51.47%, H 7.19%.

(e) disodium salt of (E)-3-cyclohexyl-2-(2,2-dimethylcyclopropyl)hydroxyphosphinoyl]methylpropenoic acid
m.p.: >300° C.
IR (KBr, cm$^{-1}$): 3418, 2926, 1551, 1428, 1335, 1146, 1035.
FAB-MS (m/e): 345 (M+H)$^+$.
$^1$H-NMR (D$_2$O, δ ppm): 0.55–0.75 (3H, m), 1.00–1.35 (5H, m), 1.07 (3H, d, J=2.1 Hz), 1.22 (3H, s), 1.50–1.70 (5H, m), 2.35–2.50 (1H, m), 2.50 (2H, d, J=16.5 Hz), 5.37 (1H, dd, J=4.4 Hz, 12.8 Hz).

Elemental analysis for C$_{15}$H$_{23}$Na$_2$O$_4$P·3/4H$_2$O:
Calculated: C 50.35%, H 6.90%.
Found: C 50.20%, H 7.14%.

EXAMPLE 15

(a) ethyl (Z)-2-(ethoxyisobutylphosphinoyl)methyl-2-butenoate
Oil
IR (neat, cm$^{-1}$) 2962, 1713, 1278, 1176, 1038, 954.
FAB-MS (m/e) 277 (M+H)$^+$.
$^1$H-NMR (CDCl$_3$, δ ppm): 1.04 (6H, dd, J=2.9 Hz, 6.6 Hz), 1.24–1.31 (6H, m), 1.62 (2H, dd, J=6.9 Hz, 12.4 Hz), 1.91 (3H, dd, J=4.6 Hz, 7.1 Hz), 2.04–2.20 (1H, m), 2.93 (2H, d, J=16.6 Hz), 3.95–4.15 (2H, m), 4.20 (2H, q, J=7.1 Hz), 7.06 (1H, dq, J=5.4 Hz, 7.1 Hz).

(b) (Z)-2-(hydroxyisobutylphosphinoyl)methyl-2-butenoic acid
m.p. 156°–159° C.
IR (KBr, cm$^{-1}$) 2962, 1701, 1251, 1167, 1119, 957.
FAB-MS (m/e): 221 (M+H)$^+$.
$^1$H-NMR (CD$_3$OD, δ ppm): 1.04 (6H, d, J=6.1 Hz), 1.63 (2H, dd, J=6.7 Hz, 12.8 Hz), 1.90 (3H, dd, J=4.5 Hz, 7.1 Hz), 2.09 (1H, m), 2.92 (2H, d, J=17.0 Hz), 7.09 (1H, dq, J=5.5 Hz, 7.1 Hz).
Elemental analysis for C$_9$H$_{17}$O$_4$P:
Calculated: C 49.04%, H 7.78%.
Found: C 48.73%, H 8.02%.

EXAMPLE 16

(a) ethyl (Z)-2-(ethoxyisobutylphosphinoyl)methyl-2-octenoate
Oil
IR (neat, cm$^{-1}$) 2960, 1718, 1265, 1170, 1039, 952.
FAB-MS (m/e): 333 (M+H)$^+$.
$^1$H-NMR (CDCl$_3$, δ ppm): 0.90 (3H, t, J=7.0 Hz), 1.05 (6H, dd, J=3.9 Hz, 6.5 Hz), 1.25–1.34 (10H, m), 1.48 (2H, m), 1.63 (2H, dd, J=6.9 Hz, 12.5 Hz), 2.12 (1H, m), 2.27 (2H, m), 2.93 (2H, d, J=16.6 Hz), 4.03 (2H, m), 4.22 (2H, q, J=7.0 Hz), 6.94 (1H, dt, J=5.2 Hz, 7.3 Hz).

(b) ethyl (E)-2-(ethoxyisobutylphosphinoyl)methyl-2-octenoate
Oil
IR (neat, cm$^{-1}$) 2955, 1722, 1242, 1161, 1038, 952.
$^1$H-NMR (CDCl$_3$, δ ppm): 0.89 (3H, t, J=7.0 Hz), 1.05 (6H, d, J=7.0 Hz), 1.25–1.36 (10H, m), 1.44 (2H, m), 1.62 (2H, m), 2.11 (1H, m), 2.49 (2H, m), 2.85 (2H, m), 4.04 (2H, m), 4.23 (2H, q, J=7.0 Hz), 6.12 (1H, dt, J=4.6 Hz, 7.6 Hz).

(c) (Z)-2-(hydroxyisobutylphosphinoyl)methyl-2-octenoic acid
m.p.: 104°–105° C.
IR (KBr, cm$^{-1}$) 2956, 1692, 1242, 1173, 1062, 987.
FAB-MS (m/e): 277 (M+H)$^+$.
$^1$H-NMR (CD$_3$OD, δ ppm): 0.92 (3H, t, J=6.8 Hz), 1.04 (6H, d, J=6.6 Hz), 1.35 (4H, m), 1.49 (2H, m), 1.63 (2H, dd, J=6.6 Hz, 13.0 Hz), 2.09 (1H, m), 2.30 (2H, m), 2.91 (2H, d, J=17.4 Hz), 6.97 (1H, dt, J=5.1 Hz, 7.6 Hz).
Elemental analysis for C$_{13}$H$_{25}$O$_4$P:
Calculated: C 56.51%, H 9.12%.
Found: C 55.29%, H 8.86%.

(d) (E)-2-(hydroxyisobutylphosphinoyl)methyl-2-octenoic acid
m.p.: 76.5°–77.5° C.
IR (KBr, cm$^{-1}$) 2962, 2932, 1692, 1275, 1161, 981.
FAB-MS (m/e): 277 (M+H)$^+$.

$^1$H-NMR (CD$_3$OD, δ ppm): 0.90 (3H, t, J=6.7 Hz), 1.04 (6H, d, J=6.6 Hz), 1.34 (4H, m), 1.46 (2H, m), 1.63 (2H, dd, J=6.9 Hz, 13.2 Hz), 2.09 (1H, m), 2.53 (2H, m), 2.81 (2H, d, J=16.9 Hz), 6.17 (1H, dt, J=4.8 Hz, 7.6 Hz). Elemental analysis for C$_{13}$H$_{25}$O$_4$P:
Calculated: C 56.51%, H 9.12%.
Found: C 56.36%, H 9.01%.

EXAMPLE 17

(a) ethyl (Z)-2-(ethoxyisobutylphosphinoyl)methyl-2-dodecenoate
Oil
FAB-MS (m/e): 389 (M+H)$^+$.
$^1$H-NMR (CDCl$_3$, δ ppm): 0.88 (3H, t, J=6.3 Hz), 1.00–1.50 (26H, m), 1.63 (2H, dd, J=6.6 Hz, 12.6 Hz), 2.05–2.20 (1H, m), 2.20–2.35 (2H, m), 2.93 (2H, d, J=16.5 Hz), 3.95–4.15 (2H, m), 4.22 (4H, q, J=6.9 Hz), 6.94 (1H, dt, J=5.1 Hz, 7.5 Hz).

(b) ethyl (E)-2-(ethoxyisobutylphosphinoyl)methyl-2-dodecenoate
Oil
FAB-MS (m/e): 389 (M+H)$^+$.
$^1$H-NMR (CDCl$_3$, δ ppm): 0.88 (3H, t, J=6.9 Hz), 1.04 (6H, d, J=6.6 Hz), 1.15–1.50 (20H, m), 1.59–1.66 (2H, m), 2.00–2.20 (1H, m), 2.45–2.55 (2H, m), 2.70–3.00 (2H, m), 3.95–4.15 (2H, m), 4.19–4.26 (2H, m), 6.12 (1H, dt, J=4.8 Hz, 7.2 Hz).

(c) (Z)-2-(hydroxyisobutylphosphinoyl)methyl-2-dodecenoic acid
m.p.: 103°–105° C.
IR (KBr, cm$^{-1}$) 2926, 1689, 1242, 1170, 984.
FAB-MS (m/e): 333 (M+H)$^+$.
$^1$H-NMR (CD$_3$OD, δ ppm): 0.90 (3H, t, J=6.6 Hz), 1.05 (6H, d, J=6.6 Hz), 1.20–1.55 (14H, m), 1.64 (2H, dd, J=6.6 Hz, 12.9 Hz), 2.00–2.20 (1H, m), 2.20–2.40 (2H, m), 2.91 (2H, d, J=17.4 Hz), 6.97 (1H, dt, J=5.1 Hz, 7.2 Hz).
Elemental analysis for C$_{17}$H$_{33}$O$_4$P:
Calculated: C 61.42%, H 10.01%.
Found: C 60.89%, H 9.92%.

(d) (E)-2-(hydroxyisobutylphosphinoyl)methyl-2-dodecenoic acid
m.p.: 50°–52.5° C.
IR (KBr, cm$^{-1}$) 2920, 2854, 1692, 1155, 954.
FAB-MS (m/e): 333 (M+H)$^+$.
$^1$H-NMR (CD$_3$OD, δ ppm): 0.89 (3H, t, J=6.6 Hz), 1.04 (6H, d, J=6.6 Hz), 1.20–1.50 (14H, m), 1.63 (2H, dd, J=6.9 Hz, 13.2 Hz), 2.00–2.20 (1H, m), 2.45–2.60 (2H, m), 2.82 (2H, d, J=16.8 Hz), 6.16 (1H, dt, J=4.8 Hz, 7.5 Hz).
Elemental analysis for C$_{17}$H$_{33}$O$_4$P:
Calculated: C 61.42%, H 10.01%.
Found: C 61.29%, H 9.85%.

EXAMPLE 18

(a) ethyl (Z)-2-(ethoxyisobutylphosphinoyl)methyl-4,4-dimethyl-2-pentenoate
Oil
IR (neat, cm$^{-1}$) 2962, 1713, 1260, 1200, 1155, 1038, 954.
FAB-MS (m/e) 319 (M+H)$^+$.
$^1$H-NMR (CDCl$_3$, δ ppm): 1.05 (6H, dd, J=3.5 Hz, 6.6 Hz), 1.24–1.33 (15H, m), 1.68 (2H, dd, J=6.9 Hz, 12.9 Hz), 2.04–2.19 (1H, m), 3.12 (2H, d, J=16.4 Hz), 3.96–4.11 (2H, m), 4.21 (2H, q, J=7.1 Hz), 6.86 (1H, d, J=4.6 Hz).

(b) ethyl (E)-2-(ethoxyisobutylphosphinoyl)methyl-4,4-dimethyl-2-pentenoate
Oil
IR (neat, cm$^{-1}$) 2962, 1731, 1239, 1197, 1052, 957.
FAB-MS (m/e): 319 (M+H)$^+$.
$^1$H-NMR (CDCl$_3$, -δ ppm): 1.05 (6H, dd, J=2.3 Hz, 6.6 Hz), 1.12 (9H, s), 1.27–1.36 (6H, m), 1.62–1.69 (2H, m), 2.00–2.14 (1H, m), 2.63–2.89 (2H, m), 3.94–4.27 (4H, m), 5.71 (1H, d, J=4.4 Hz).

(c) (Z)-2-(hydroxyisobutylphosphinoyl)methyl-4,4-dimethyl-2-pentenoic acid
m.p.: 141°–143° C.
IR (KBr, cm$^{-1}$) 2962, 1686, 1248, 1185, 1104, 972.
FAB-MS (m/e): 263 (M+H)$^+$.
$^1$H-NMR (CD$_3$OD, .δ ppm): 1.05 (6H, d, J=6.6 Hz), 1.24 (9H, s), 1.70 (2H, dd, J=6.5 Hz, 13.2 Hz), 2.07–2.15 (1H, m), 3.10 (2H, d, J=16.9 Hz), 6.93 (1H, d, J=4.9 Hz).
Elemental analysis for C$_{12}$H$_{23}$O$_4$P:
Calculated: C 54.95%, H 8.84%.
Found: C 54.71%, H 8.95%.

(d) (E)-2-(hydroxyisobutylphosphinoyl)methyl-4,4-dimethyl-2-pentenoic acid
m.p.: 157°–158.5° C.
IR (KBr, cm$^{-1}$) 2962, 1713, 1257, 1191, 1119, 972.
FAB-MS (m/e): 263 (M+H)$^+$.
$^1$H-NMR (CD$_3$OD, δ ppm): 1.05 (6H, d, J=6.6 Hz), 1.16 (9H, s), 1.69 (2H, dd, J=6.9 Hz, 13 4 Hz), 2.02–2.14 (1H, m), 2.72 (2H, d, J=17.1 Hz), 5.76 (1H, d, J=4.9 Hz).
Elemental analysis for C$_{12}$H$_{23}$O$_4$P:
Calculated: C 54.95%, H 8.84%.
Found: C 54.78%, H 8.90%.

EXAMPLE 19

(a) ethyl (Z)-2-(ethoxyisobutylphosphinoyl)methyl-4-methyl-2-pentenoate
Oil
IR (neat, cm$^{-1}$) 2962, 1713, 1269, 1170, 1038, 960.
FAB-MS (m/e): 305 (M+H)$^+$.
$^1$H-NMR (CDCl$_3$, δ ppm): 1.03 (6H, d, J=6.4 Hz), 1.05 (6H, d, J=6.3 Hz), 1.28 (3H, t, J=7.1 Hz), 1.32 (3H, t, J=7.0 Hz), 1.61 (2H, dd, J=6.5 Hz, 12.7 Hz), 2.13 (1H, m), 2.75 (1H, m), 2.95 (2H, d, J=6.6 Hz), 4.02 (2H, m), 4.22 (2H, q, J=7.1 Hz), 6.69 (1H, dd, J=4.9 Hz, 10.5 Hz).

(b) ethyl (E)-2-(ethoxyisobutylphosphinoyl)methyl-4-methyl-2-pentenoate
Oil
IR (neat, cm$^{-1}$): 2962, 1722, 1236, 1185, 1038, 963.
FAB-MS (m/e): 305 (M+H)$^+$
$^1$H-NMR (CDCl$_3$, δ ppm): 1.01 (6H, d, J=6.6 Hz), 1.04 (6H, d, J=6.6 Hz), 1.28 (3H, t, J=7.1 Hz), 1.32 (3H, t, J=7.1 Hz), 1.55–1.65 (2H, m), 2.13 (1H, m) 2.81 (2H, m), 3.15–3.30 (1H, m), 4.04 (2H, m), 4.22 (2H, m), 5.86 (1H, dd, J=4.7 Hz, 7.2 Hz).

(c) (Z)-2-(hydroxyisobutylphosphinoyl)methyl-4-methyl-2pentenoic acid
m.p.: 114.2°–114.7° C.
IR (KBr, cm$^{-1}$): 2962, 1692, 1284, 1179, 1065, 969.
FAB-MS (m/e): 249 (M+H)$^+$.
$^1$H-NMR (CD$_3$OD, δ ppm): 1.038 (6H, d, J=7.0 Hz), 1.043 (6H, d, J=6.6 Hz), 1.65 (2H, dd, J=6.5 Hz, 12.9 Hz), 2.10 (1H, m) 2.79 (1H, m), 2.88 (2H, d, J=17.1 Hz), 6.73 (1H, dd, J=5.2 Hz, 10.5 Hz).
Elemental analysis for C$_{11}$H$_{21}$O$_4$P:
Calculated: C 53.22%, H 8.53%.
Found: C 53.26%, H 8.91%.

EXAMPLE 20

(a) ethyl (Z)-2-(ethoxyisobutylphosphinoyl)methyl-5-methyl-2-hexenoate
Oil
IR (neat, cm$^{-1}$): 2962, 1713, 1290, 1260, 1173, 1038, 954.
FAB-MS (m/e): 319 (M+H)$^+$.
$^1$H-NMR (CDCl$_3$, δ ppm): 0.94 (6H, d, J=7.1 Hz), 1.04 (6H, dd, J=3.9 Hz, 6.8 Hz), 1.27 (3H, t, J=7.0 Hz), 1.31 (3H, t, J=7.0 Hz), 1.63 (2H, dd, J=6.7 Hz, 12.6 Hz), 1.78 (1H, m), 2.04–2.22 (3H, m), 2.93 (2H, d, J=16.6 Hz), 4.04 (2H, m), 4.21 (2H, q, J=7.0 Hz), 6.96 (1H, dt, J=4.9 Hz, 7.3 Hz).

(b) ethyl (E)-2-(ethoxyisobutylphosphinoyl)methyl-5-methyl-2-hexenoate
Oil
IR (neat, cm$^{-1}$): 2962, 1719, 1224, 1173, 1038, 954.
FAB-MS (m/e): 319 (M+H)$^+$.
$^1$H-NMR (CDCl$_3$, δ ppm): 0.95 (6H, d, J=6.5 Hz), 1.06 (6H, d, J=7.0 Hz), 1.29 (3H, t, J=6.5 Hz), 1.34 (3H, t, J=7.0 Hz), 1.63 (2H, m), 1.74 (1H, m), 2.13 (1H, m), 2.35–2.45 (1H, m), 2.79–2.96 (2H, m), 3.95–4.15 (2H, m), 4.2–4.3 (2H, m), 6.15 (1H, dt, J=4.6 Hz, 7.4 Hz).

(c) (Z)-2-(hydroxyisobutylphosphinoyl)methyl-5-methyl-2hexenoic acid
m.p.: 127.5°–129.0° C.
IR (KBr, cm$^{-1}$): 2962, 1683, 1302, 1272, 1074, 969.
FAB-MS (m/e): 263 (M+H)$^+$.
$^1$H-NMR (CD$_3$OD, δ ppm): 0.95 (6H, d, J=7.0 Hz), 1.03 (6H, d, J=6.5 Hz), 1.62 (2H, dd, J=6.5 Hz, 13.0 Hz), 1.76 (1H, m), 2.11 (1H, m), 2.15–2.25 (2H, m), 2.89 (2H, d, J=17.4 Hz), 7.00 (1H, dt, J=5.1 Hz, 7.3 Hz).
Elemental analysis for C$_{12}$H$_{23}$O$_4$P:
Calculated: C 54.95%, H 8.84%.
Found: C 54.93 %, H 8.90%.

EXAMPLE 21

(a) ethyl (Z)-3-cyclopropyl-2-(ethoxyisobutylphosphinoyl)methylpropenoate
Oil
IR (neat, cm$^{-1}$): 2962, 1701, 1272, 1182, 1038, 966.
FAB-MS (m/e): 303 (M+H)$^+$.
$^1$H-NMR (CDCl$_3$, δ ppm): 0.68 (2H, m), 1.01 (2H, m), 1.04 (6h, m), 1.23–1.32 (6H, m), 1.65 (2H, m), 1.76 (1H, m), 2.14 (1H, m), 3.01 and 3.07 (2H, AB-type dd, J=14.8 Hz, 16.5 Hz). 4.09 (2H, m), 4.19 (2H, q, J=7.0 Hz), 6.29 (1H, dd, J=4.9 Hz, (10.7 Hz).

(b) ethyl (E)-3-cyclopropyl-2-(ethoxyisobutylphosphinoyl)methylpropenoate
Oil
IR (neat, cm$^{-1}$): 2962, 1713, 1251, 1188, 1098, 966.
FAB-MS (m/e): 303 (M+H)$^+$.
$^1$H-NMR (CDCl$_3$, δ ppm): 0.53 (2H, m), 0.95 (2H, m), 1.03 (6H, d, J=6.5 Hz), 1.26 (3H, t, J=7.1 Hz), 1.32 (3H, t, J=7.1 Hz), 1.62 (2H, m), 2.10 (1H, m), 2.60 (1H, m), 2.76 and 2.84 (2H, AB-type dd, J=15.2 Hz, 15.5 Hz). 4.08 (2H, m), 4.26 2H, m), 5.40 (1H, dd, J50 4.4 Hz, 10.8 Hz).

(c) (Z)-3-cyclopropyl-2-(hydroxyisobutylphosphinoyl)-methylpropenoic acid
m.p.: 153°–154.5° C.
IR (KBr, cm$^{-1}$): 2962, 1695, 1248, 1173, 1119, 957.
FAB-MS (m/e): 247 (M+H)$^+$.
$^1$H-NMR (CD$_3$OD, δ ppm): 0.66 (2H, m), 1.01 (2H, m), 1.05 (6H, d, J=6.1 Hz), 1.66 (2H, dd, J=6.7 Hz, 12.9 Hz), 1.77 (1H, m), 2.13 (1H, m), 3.01 (2H, d, J=17.3 Hz), 6.35 (1H, dd J=5.0 Hz, 10.8 Hz).
Elemental analysis for C$_{11}$H$_{19}$O$_4$P:
Calculated: C 53.66%, H 7.78%.
Found: C 53.30%, H 7.74%.

EXAMPLE 22

(a) ethyl (Z)-2-(ethoxyisobutylphosphinoyl)methyl-5-phenyl-2-pentenoate
Oil
IR (neat, cm$^{-1}$):, 2962, 1713, 1272, 1248, 11979, 1038, 954.
FAB-MS (m/e): 367 (M+H)$^+$.
$^1$H-NMR (CDCl$_3$, δ ppm): 1.03 (6H, dd, J=2.6 Hz, 6.6 Hz), 1.25 (3H, t, J=6.8 Hz), 1.30 (3H, t, J=7.1 Hz), 1.62 (2H, dd, J=6.7 Hz, 12.5 Hz), 2.12 (2H, m), 2.65 (2H, m), 2.78 (2H, m), 2.85 (2H, d, J=16.5 Hz), 4.03 (2H, m), 4.22 (2H, q, J=7.1 Hz), 6.99 (1H, dt, J=5.1 Hz, 7.2 Hz), 7.16 (5H, ml).

(b) ethyl (E)-2-(ethoxyisobutylphosphinoyl)methyl-5-phenyl-2-pentenoate
Oil
IR (neat, cm$^{-1}$): 2962, 1716, 1236, 1188, 1035, 954.
FAB-MS (m/e): 367 (M+H)$^+$.
$^1$H-NMR (CDCl$_3$, δ ppm): 1.03 (6H, d, J=6.3 Hz), 1.26 (3H), t, J=7.1 Hz), 1.31 (3H, t, J=7.2 Hz), 1.59 (2H, m), 2.10 (2H, m), 2.73–2.90 (6H, m), 4.04 (2H, m), 4.23 (2H, m), 6.16 (1H, dt, J=4.6 Hz, 7.4 Hz), 7.27 (5H, m).

(c) (Z)-2-(hydroxyisobutylphosphinoyl)methyl-5-phenyl-2-pentenoic acid
m.p.: 127.0°–127.5° C.
IR (KBr, cm$^{-1}$): 2962, 1650, 1308, 1236, 1110, 1014, 939.
FAB-MS (m/e): 311 (M+H)$^+$.
$^1$H-NMR (CD$_3$OD, δ ppm): 1.04 (6H, dd, J=6.6 Hz), 1.62 (2H, dd, J=6.3 Hz, 12.9 Hz), 2.10 (1H, m), 2.62 (2H, m), 2.76–2.86 (4H, m), 7.02 (1H, dt, J=5.0 Hz, 7.3 Hz), 7.24 (5H, m).
Elemental analysis for C$_{16}$H$_{23}$O$_4$P:
Calculated: C 61.93%, H 7.47%.
Found: C 62.05%, H 7.77%.

EXAMPLE 23

(a) ethyl (Z)-6-chloro-2-(ethoxyisobutylphosphinoyl)-methyl-2-hexenoate
Oil
FAB-MS (m/e): 339 (M+H)$^+$.
$^1$H-NMR (CDCl$_3$, δ ppm): 1.05 (6H, dd, J=2.7 Hz, 6.6 Hz), 1.28 (3H, t, J=7.2 Hz), 1.31 (3H, t, J=7.2 Hz), 1.64 (2H, dd, J=6.6 Hz, 12.9 Hz), 1.93–2.02 (2H, m), 2.05–2.20 (1H, m), 2.50 (2H, ddt, J=3.9 Hz, 7.5 Hz, 7.5 Hz), 2.95 (2H, d, J=16.5 Hz), 3.57 (2H, t, J=6.3 Hz), 3.95–4.15 (2H, m), 4.22 (2H, q, J=7.2 Hz), 6.90 (1, dt, J=5.4 Hz, 7.5 Hz).

(b) ethyl (E)-6-chloro-2-(ethoxyisobutylphosphinoyl)-methyl-2-hexenoate
Oil
FAB-MS (m/e): 339 (M+H)$^+$.
$^1$H-NMR (CDCl$_3$, δ ppm): 1.05 (6H, d, J=6.9 Hz), 1.28 (3H, t, J=7.2 Hz), 1.33 (3H, t, J=7.2 Hz), 1.60 (2H, dd, J=6.6 Hz, 12.6 Hz), 1.85–2.00 (2H, m), 2.00–2.20 (1H, m), 2.60–2.70 (2H, m), 2.80–2.90 (2H, m), 3.56 (2H, t, J=6.6 Hz), 3.95–4.20 (2H, m), 4.24 (2H, q, J=7.2 Hz), 6.12 (1H, dt, J=5.1 Hz, 7.5 Hz).

(c) (Z)-6-chloro-2-(hydroxyisobutylphosphinoyl)methyl-2-hexenoic acid
m.p.: 129.5°–130.5° C.
IR (KBr, cm$^{-1}$), 2962, 1692, 1278, 1245, 1167, 969.
FAB-MS (m/e): 283 (M+H)$^+$.

¹H-NMR (CD₃OD, δ ppm): 1.05 (6H, d, J=6.6 Hz), 1.65 (2H, dd, J=6.6 Hz, 12.9 Hz), 1.90–2.00 (2H, m), 2.00–2.20 (1H, m), 2.48 (2H, ddt, J=3.9 Hz, 7.2 Hz, 7.2 Hz), 2.95 (2H, d, J=17.1 Hz), 3.60 (2H, t, J=6.6 Hz), 6.95 (1H, dt, J=5.1 Hz, 7.5 Hz).

Elemental analysis for $C_{11}H_{20}ClO_4P$:
Calculated: C 46.74%, H 7.13%.
Found: C 46.72%, H 7.61%.

EXAMPLE 24

(a) ethyl (Z)-8-chloro-2-(ethoxyisobutylphosphinoyl)methyloctenoate
Oil
IR (neat, cm⁻¹): 2962, 1713, 1275, 1173, 1104, 1038, 954.
FAB-MS (m/e): 367 (M+H)⁺.
¹H-NMR (CDCl₃, δ ppm): 1.04 (6H, dd, J=2.6 Hz, 7.0 Hz), 1.28 (3H, t, J=7.1 Hz), 1.31 (3H, t, J=7.1 Hz), 1.48–1.53 (4H, m), 1.60–1.67 (2H, m), 1.77–1.82 (2H, m), 2.08–2.16 (1H, m), 2.31–2.35 (2H, m), 2.93 (2H, d, J=16.4 Hz), 3.54 (2H, t, J=6.5 Hz), 3.96–4.13 (2H, m), 4.22 (2H, q, J=7.1 Hz), 6.93 (1H, dt, J=5.1 Hz, 7.3 Hz).

(b) ethyl (E)-8-chloro-2-(ethoxyisobutylphosphinoyl)methyloctenoate
Oil
IR (neat, cm⁻¹): 2962, 1716, 1233, 1176, 1104, 1038, 954.
FAB-MS (m/e): 367 (M+H)⁺.
¹H-NMR (CDCl₃, δ ppm): 1.04 (6H, d, J=7.0 Hz), 1.28 (3H, t, J=7.0 Hz), 1.32 (3H, t, J=7.0 Hz), 1.45–1.51 (4H, m), 1.56–1.65 (2H, m), 1.75–1.81 (2H, m), 2.04–2.14 (1H, m), 2.50–2.54 (2H, m), 2.84 (2H, m), 3.53 (2H, t, J=6.8 Hz), 4.01–4.12 (2H, m), 4.13–4.27 (2H, m), 6.11 (1H, dt, J=4.6 Hz, 7.6 Hz).

(c) (Z)-8-chloro-2-(hydroxyisobutylphosphinoyl)methyl-2-octenoic acid
m.p.: 97.2°–98.5° C.
IR (KBr, cm⁻¹): 2956, 1692, 1284, 1170, 1059, 966.
FAB-MS (m/e): 311 (M+H)⁺.
¹H-NMR (CD₃OD, δ ppm): 1.05 (6H, d, J=6.5 Hz), 1.49–1.54 (4H, m), 1.64 (2H, dd, J=6.9 Hz, 12.9 Hz), 1.76–1.82 (2H, m), 2.06–2.12 (1H, m) 2.30–2.35 (2H, m), 2.90 (2H, d, J=17.0 Hz), 3.57 (2H, t, J=6.8 Hz), 6.97 (1H, dt, J=5.5 Hz, 7.3 Hz).

Elemental analysis for $C_{13}H_{24}ClO_4P$:
Calculated: C 50.25%, H 7.78%.
Found: C 49.24%, H 7.68%.

EXAMPLE 25

(a) ethyl (Z)-2-(ethoxyisobutylphosphinoyl)methyl-6-methoxycarbonyl-2-hexenoate
Oil
FAB-MS (m/e): 363 (M+H)⁺.
¹H-NMR (CDCl₃, δ ppm): 1.05 (6H, dd, J=2.7 Hz, 6.6 Hz), 1.27 (3H, t, J=7.2 Hz), 1.31 (3H, t, J=7.2 Hz), 1.63 (2H, dd, J=6.9 Hz, 12.6 Hz), 1.75–1.90 (2H, m), 2.00–2.20 (1H, m), 2.30–2.45 (2H, m), 2.37 (2H, t, J=7.5 Hz), 2.92 (2H, d, J=16.8 Hz), 3.67 (3H, s), 3.95–4.15 (2H, m), 4.22 (2H, q, J=7.2 Hz), 6.91 (1H, dt, J=5.1 Hz, 7.2 Hz).

(b) ethyl (E)-2-(ethoxyisobutylphosphinoyl)methyl-6-methoxycarbonyl-2-hexenoate
Oil
FAB-MS (m/e): 363 (M+H)⁺.
¹H-NMR (CDCl₃, δ ppm): 1.04 (6H, d, J=6.0 Hz), 1.28 (3H, t, J=6.9 Hz), 1.32 (3H, t, J=6.9 Hz), 1.62 (2H, dd, J=6.3 Hz, 12.6 Hz), 1.70–1.90 (2H, m), 2.00–2.20 (1H, m) 2.35 (2H, t, J=7.8 Hz), 2.50–2.60 (2H, m), 2.70–3.00 (2H, m), 3.67 (3H, s), 3.90–4.15 (2H, m), 4.23 (2H, m), 6.09 (1H, dt, J=4.5 Hz, 7.5 Hz).

(c) (Z)-2-(hydroxyisobutylphosphinoyl)methyl-2-heptenedioic acid
m.p.: 144°–146° C.
IR (KBr, cm⁻¹) 2962, 1707, 1248, 966.
FAB-MS (m/e): 293 (M+H)⁺.
¹H-NMR (CD₃OD, δ ppm 1.05 (6H, d, J=6.6 Hz), 1.64 (2H, dd, J=6.9 Hz, 12.9 Hz), 1.78 (2H, tt, J=7.2 Hz, 7.2 Hz), 2.00–2.10 (1H, m), 2.30–2.40 (2H, m), 2.35 (2H, t, J=7.2 Hz), 2.93 (2H, d, J=17.1 Hz), 6.96 (1H, dt, J=5.4 Hz, 7.5 Hz).

Elemental analysis for $C_{12}H_{21}O_6P$:
Calculated: C 49.31%, H 7.24%
Found: C 49.53%, H 7.68%

EXAMPLE 26

(a) ethyl (Z)-3-cyclopropyl-2-[(2,2-dimethycyclopropyl)ethoxyphosphinoyl)methylpropenoate
Oil
IR (neat, cm⁻¹): 2986, 1707, 1332, 1272, 1179, 1050, 966.
FAB-MS (m/e): 315 (M+H)⁺.
¹H-NMR (CDCl₃, δ ppm): 0.54 (1H, m), 0.65 (2H, m), 0.78 (1H, m), 1.01 (2H, m), 1.07 (6H, d, J=2.4 Hz), 1.08 (1H, m), 1.30 (6H, m), 1.84 (1H, m), 3.00–3.21 (2H, m), 4.05 (2H, m), 4.19 (2H, q, J=7.0 Hz), 6.32 (1H, dd, J=11.1 Hz, 5.1 Hz).

(b) ethyl (E)-3-cyclopropyl-2-(2,2-dimethylcyclopropyl)ethoxyphosphinoyl)methylpropenoate
Oil
IR (neat, cm⁻¹) 2986, 1710, 1248, 1188, 1038, 966.
FAB-MS (m/e): 315 (M+H)⁺.
¹H-NMR (CDCl₃, δ ppm): 0.55 (3H, m), 0.81 (1H, m), 0.96 (2H, m), 1.12 (6H, s), 1.10 (1H, m), 1.30 (6H, m), 2.66 (1H, m), 2.88 (2H, m), 4.17 (2H, m), 4.23 (2H, m), 5.42 (1H, dd, J=4.6 Hz, 10.0 Hz).

(c) (Z)-3-cyclopropyl-2-[(2,2-dimethylcyclopropyl)hydroxyphosphinoyl)methylpropenoic acid
m.p.: 158.0°–159.0° C.
IR (KBr, cm⁻¹) 2956, 2878, 1683, 1239, 1179, 1155, 975.
FAB-MS (m/e): 259 (M+H)⁺.
¹H-NMR (CD₃OD, δ ppm): 0.64 (2H, m), 0.68–0.78 (2H, m), 0.93 (1H, ddd, J=16.8 Hz, 6.3 Hz, 3.9 Hz), 1.02 (2H, m), 1.11 (3H, d, J=2.2 Hz), 1.30 (3H, s), 1.82 (1H, m), 3.06 (2H, m), 6.35 (1H, dd, J=5.1 Hz, 11.1 Hz).

Elemental analysis for $C_{12}H_{19}O_4P$:
Calculated: C 55.81%, H 7.42%.
Found: C 55.41%, H 7.39%.

EXAMPLE 27

(a) ethyl (Z)-2-(cyclohexylmethylethoxyphosphinoyl)methyl-3-cyclopropylpropenoate
Oil
IR (neat, cm⁻¹) 2926, 1710, 1272, 1158, 1035, 966.
FAB-MS (m/e): 343 (M+H)⁺.
¹H-NMR (CDCl₃, δ ppm): 0.65–0.70 (2H, m), 0.98–1.29 (13H, m), 1.59–1.91 (9H, m), 2.95–3.13 (2H, m), 3.98–4.15 (2H, m), 4.19 (2H, q, J=7.1 Hz), 6.29 (1H, dd, J=4.9 Hz, 10.7 Hz).

(b) (Z)-2-(cyclohexylmethylhydroxyphosphinoyl)methyl-3-cyclopropylpropenoic acid
m.p.: 173.5°–175.0° C.
IR (KBr, cm⁻¹) 2926, 1686, 1284, 1167, 969.
FAB-MS (m/e): 287 (M+H)⁺.

$^1$H-NMR (CD$_3$OD, δ ppm): 0.63–0.68 (2H, m), 0.97–1.37 (7H, m), 1.62–1.93 (9H, m), 3.01 (2H, d, J=17.3 Hz), 6.35 (1H, dd, J=5.0 Hz, 10.9 Hz).
Elemental analysis for C$_{14}$H$_{23}$O$_4$P:
Calculated: C 58.73%, H 8.10%.
Found: C 58.23%, H 8.13%.

EXAMPLE 28

(a) ethyl (Z)-2-(benzylethoxyphosphinoyl)methyl-3-cyclohexylpropenoate
Oil
IR (neat, cm$^{-1}$): 2926, 1713, 1278, 1227, 1173, 1038, 957.
FAB-MS (m/e): 379 (M+H)$^+$.
$^1$H-NMR (CDCl$_3$, δ ppm): 1.13 (3H, t, J=7.1 Hz) 1.10–1.40 (5H, m), 1.30 (3H, t, J=7.1 Hz), 1.67 (5H, m), 2.34 (1H, m), 2.93 (2H, d, J=16.7 Hz), 3.12 and 3.19 (2H, AB-type dd, J=15.0 Hz, 15.0 Hz), 3.90 (2H, m), 4.21 (2H, q, J=7.0 Hz), 6.80 (1H, dd, J=5.0 Hz, 10.4 Hz), 7.30 (5H, m).

(b) ethyl (E)-2-(benzylethoxyphosphinoyl)methyl-3-cyclohexylpropenoate
Oil
IR (neat, cm$^{-1}$) 2926, 1719, 1251, 1218, 1179, 1038, 957.
FAB-MS (m/e): 379 (M+H)$^+$.
$^1$H-NMR (CDCl$_3$ ppm): 1.18 (3H, t, J=7.0 Hz), 1.00–1.50 (5H, m), 1.31 (3H, t, J=7.3 Hz), 1.70 (5H, m), 2.78 (2H, m), 3.13 (2H, d, J=16.1 Hz), 3.93 (2H, m), 4.21 (2H, q, J=7.0 Hz), 5.88 (1H, dd, J=4.4 Hz, 9.6 Hz), 7.29 (5H, m).

(c) (Z)-2-(benzylhydroxyphosphinoyl)methyl-3-cyclohexylpropenoic acid
m.p.: 196.0°–197.0° C.
IR (KBr, cm$^{-1}$) 2926, 1686, 1170, 1149, 978.
FAB-MS (m/e): 323 (M+H)$^+$.
$^1$H-NMR (CD$_3$OD, δ ppm): 1.05–1.40 (5H, m), 1.70 (5H, m), 2.34 (1H, m), 2.89 (2H, d, J=16.6 Hz), 3.17 (2H, d, J=16.6 Hz), 6.75 (1H, dd, J=5.0 Hz, 10.3 Hz), 7.32 (5H, m).
Elemental analysis for C$_{17}$H$_{23}$O$_4$P:
Calculaed: C 68.35%, H 7.19%.
Found: C 63.34%, H 7.18%.

EXAMPLE 29

(a) ethyl (Z)-3-cyclohexyl-2-(cyclopentylmethylethoxyphosphinoyl)methylpropenoate
Oil
FAB-MS (m/e): 371 (M+H)$^+$.
$^1$H-NMR (CDCl$_3$, δ ppm): 1.10–2.00 (26H, m), 2.05–2.25 (1H, m), 2.40 (1H, m), 2.94 (2H, d, J=16.5 Hz), 4.05 (2H, m), 4.21 (2H, q, J=7.2 Hz), 6.72 (1H, dd, J=5.1 Hz, 10.8 Hz).

(b) (Z)-3-cyclohexyl-2-(cyclopentylmethylhydroxyphosphinoyl)methylpropenoic acid
m.p.: 178°–180° C.
IR (KBr, cm$^{-1}$) 2932, 2854, 1692, 1638, 1317, 1290, 1152, 960.
FAB-MS (m/e): 315 (M+H)$^+$.
$^1$H-NMR (CD$_3$OD, δ ppm): 1.10–2.00 (20H, m), 2.18 (1H, m), 2.48 (1H, m), 2.91 (2H, d, J=17.1 Hz), 6.75 (1H, dd, J=5.1 Hz, 10.5 Hz).
Elemental analysis for C$_{16}$H$_{27}$O$_4$P:
Calculated: C 61.13%, H 8.66%.
Found: C 60.90%, H 8.57%.

EXAMPLE 30

(a) ethyl (Z)-3-cyclohexyl-2-(cyclohexylmethylethoxyphosphinoyl)methylpropenoate
Oil
IR (neat cm$^{-1}$) 2932, 1713, 1278, 1227, 1173, 1038, 954.
FAB-MS (m/e): 385 (M+H)$^+$.
$^1$H-NMR (CDCl$_3$, δ ppm): 0.97–1.39 (16H, m), 1.59–1.90 (13H, m), 2.39–2.43 (1H, m), 2.93 (2H, d, J=16.9 Hz), 3.95–4.12 (2H, m), 4.20 (2H, q, J=7.0 Hz), 6.71 (1H, dd, J=4.9 Hz, 10.6 Hz).

(b) ethyl (E)-3-cyclohexyl-2-(cyclohexylmethylethoxyphosphinoyl)methylpropenoate
Oil
IR (neat, cm$^{-1}$) 2926, 1719, 1218, 1035, 954.
FAB-MS (m/e): 385 (M+H)$^+$.
$^1$H-NMR (CDCl$_3$, δ ppm): 0.99–1.35 (16H, m), 1.56–1.87 (13H, m), 2.77–2.93 (3H, m), 3.93–4.12 (2H, m), 4.22 (2H, q, J=7.2 Hz), 5.89 (1H, dd, J=4.7 Hz, 9.8 Hz).

(c) (Z)-3-cyclohexyl-2-(cyclohexylmethylhydroxyphosphinoyl)methylpropenoic acid
m.p.: 170.0°–171.5° C.
IR (KBr, cm$^{-1}$): 2932, 2854, 1692, 1239, 1146, 954.
FAB-MS (m/e): 329 (M+H)$^+$.
$^1$H-NMR (CD$_3$OD, δ ppm): 1.01–1.39 (10H, m), 1.60–1.92 (13H, m), 2.46–2.50 (1H, m), 2.90 (2H, d, J=17.1 Hz), 6.74 (1H, dd, J=5.2 Hz, 10.5 Hz).
Elemental analysis for C$_{17}$H$_{29}$O$_4$P:
Calculated: C 62.18%, H 8.90%.
Found: C 61.69%, H 8.86%.

EXAMPLE 31

Production of ethyl (Z)-3-cyclohexyl-2-(ethoxyhexylphosphinoyl)methylpropenoate from ethyl (E)-3-cyclohexyl-2-(ethoxyhexylphosphinoyl)methylpropenoate Ten milligrams of 10% palladium-carbon was added to a solution of 100 mg (0.27 millimole) of ethyl (E)-3-cyclohexyl-2-(ethoxyhexylphosphinoyl)methylpropenoate in 10 ml of ethanol, and the mixture was stirred at room temperature for 3 hours in an atmosphere of hydrogen. The palladium-carbon was removed by filtration, and the solvent was evaporated under reduced pressure to give a pale yellow oil. This product was a mixture of ethyl (Z)-3-cyclohexyl-2-(ethoxyhexylphosphinoyl)methylpropenoate, ethyl (E)-3-cyclohexyl-2-(ethoxyhexylphosphinoyl)methylpropenoate, and ethyl 3-cyclohexyl-2-(ethoxyhexylphosphinoyl)methylpropionate. The ratio among the components in the mixture was determined to be 74:12:14 by measurement of an integral ratio among $^1$H-NMR signals respectively assigned to each component.

EXAMPLE 32

Production of 3-cyclohexyl-2-(hexylhydroxyphosphinoyl)methylpropionic acid (a) Production of ethyl 3-cyclohexyl-2-(ethoxyhexylphosphinoyl)methylpropionate
Fifty milligrams of 10% palladium-carbon was added to a solution of 0.87 g (1.0 millimole) of ethyl (E)-3-cyclohexyl-2-(ethoxyhexylphosphinoyl)methylpropenoate in 30 ml of ethanol, and the mixture was hydrogenated at 3 kg/cm² of hydrogen in a Parr shaker apparatus for 8 hours. The palladium-carbon was removed by filtration, and the solvent was evaporated under reduced pressure to give 0.37 g (yield 99%) of the captioned compound as a pale yellow oil.

IR (neat, cm⁻¹) 2926, 1737, 1218, 1194, 1038, 954.
FAB-MS (m/e): 375 (M+H)⁺.
¹H-NMR (CDCl₃, δ ppm): 0.75-0.95 (5H, m), 1.06-1.85 (25H, m), 2.17 (1H, m), 2.83 (1H, m), 3.95-4.25 (4H, m).

(b) Production of 3-cyclohexyl-2-(hexylhydroxyphosphinoyl)methylpropionic acid

Ethyl 3-cyclohexyl-2-(ethoxyhexylphosphinoyl)methylpropionate was treated in a similar manner as in Example 2 (d), and recrystallized from methanol/ethyl acetate/hexane (1:4:40) to give the captioned compound as colorless crystals.

m.p.: 121.5°-123.0° C.
IR (KBr, cm⁻¹) 2926, 1722, 1218, 1116, 960
FAB-MS (m/e): 319 (M+H)⁺.
¹H-NMR (CD₃OD, δ ppm): 0.83-1.90 (27H, m), 2.15 (1H, m), 2.81 (1H, m).
Elemental analysis for $C_{16}H_{31}O_4P$:
Calculated: C 60.36%, H 9.81%.
Found: C 60.10%, H 9.99%.

EXAMPLES 33-38

The following compounds (Examples 33 to 38) were prepared in a similar manner as in Example 32.

EXAMPLE 33

(a) ethyl 3-cyclohexyl-2-(ethoxyethylphosphinoyl)methylpropionate
Oil

IR (neat, cm⁻¹) 2926, 1737, 1212, 1044, 954.
FAB-MS (m/e): 319 (M+H)⁺.
¹H-NMR (CDCl₃, δ ppm): 0.83-2.10 (26H, m), 2.80 (1H, m), 3.78-4.30 (4H, m).

(b) 3-cyclohexyl-2-(ethylhydroxyphosphinoyl)methylpropionic acid
m.p.: 116°-118.5° C.
IR (KBr, cm⁻¹): 2926, 1728, 1227, 1176, 1154, 1119, 951.
FAB-MS (m/e): 263 (M+H)⁺.
¹H-NMR (CD₃OD, δ ppm): 0.85-1.90 (19H, m), 2.15 (1H, m), 2.82 (1H, m).
Elemental analysis for $C_{12}H_{23}O_4P$:
Calculated: C 54.95%, H 8.84%.
Found: C 55.75%, H 9.02%.

EXAMPLE 34

(a) ethyl 3-cyclohexyl-2-(ethoxyisopropylphosphinoyl)methylpropionate
Oil

IR (neat, cm 2926, 1737, 1212, 1032, 954.
FAB-MS (m/e): 333 (M+H)⁺.
¹H-NMR (CDCl₃, δ ppm): 0.80-2.25 (31H, m), 2.90 (1H, m), 4.00-4.25 (4H, m).

(b) 3-cyclohexyl-2-(hydroxyisopropylphosphinoyl)methylpropionic acid
m.p.: 129.5°-130.5° C.
IR (KBr, cm⁻¹) 2926, 1722, 1230, 1176, 1131, 951.
FAB-MS (m/e): 277 (M+H)⁺.
¹H-NMR (CD₃OD, δ ppm): 0.85-1.90 (21H, m), 2.16 (1H, m), 2.83 (1H, m).
Elemental analysis for $C_{13}H_{25}O_4P$:
Calculated: C 56.51%, H 9.12%.
Found: C 56.59%, H 9.70%.

EXAMPLE 35

2-(butylhydroxyphosphinoyl)methyl-3-cyclohexylpropionic acid
m.p.: 118°-121° C.
IR (KBr, cm⁻¹) 3440, 2940, 1686, 1138, 1030.
FAB-MS (m/e): 291 (M+H)⁺.
¹H-NMR (CD₃OD, δ ppm): 0.93 (3H, t, J=6 Hz), 1.16-1.97 (21H, m), 2.71-2.87 (1H, m).
Elemental analysis for $C_{14}H_{27}O_4P$:
Calculated: C 57.92%, H 9.37%.
Found: C 57.48%, H 9.02%.

EXAMPLE 36

(a) ethyl 3-cyclohexyl-2-(ethoxyisobutylphosphinoyl)methylpropionate
Oil

IR (neat, cm⁻¹) 2932, 1740, 1260, 1227, 1170, 1035, 966.
¹H-NMR (CDCl₃, δ ppm): 0.80-2.30 (30H, m), 2.60-3.10 (1H, m), 3.90-4.40 (4H, m).

(b) 3-cyclohexyl-2-(hydroxyisobutylphosphinoyl)methylpropionic acid
m.p.: 154°-155° C.
IR (KBr, cm⁻¹) 2926, 1719, 1227, 1173, 1122, 969.
High-resolution FAB-MS
[m/e, for $(C_{14}H_{27}O_4P+H)^+$].
Calculated: 291.1725.
Found: 291.1717.
¹H-NMR (CD OD, δ ppm): 0.85-0.96 (2H, m), 1.05 (6H, d, J=6.6 Hz), 1.18-1.89 (14H, m), 2.02-2.18 (2H, m), 2.79-2.83 (1H, m).

EXAMPLE 37

(a) ethyl 3-cyclohexyl-2-(decylethoxyphosphinoyl)methylpropionate
Oil

IR (neat, cm⁻¹) 2930, 1740, 1455, 1381, 1197, 1041, 956.
FAB-MS (m/e): 431 (M+H)⁺.
¹H-NMR (CDCl₃, δ ppm): 0.88 (3H, t, J=7 Hz), 1.05-1.89 (38H, m), 2.09-2.27 (1H, m), 2.74-2.94 (1H, m), 3.92-4.28 (4H, m).

(b) 3-cyclohexyl-2-(decylhydroxyphosphinoyl)methylpropionic acid
m.p.: 124°-125.5° C.
IR (KBr, cm⁻¹) 2920, 1720, 1450, 1230, 1175, 958.
FAB-MS (m/e): 375 (M+H)⁺.
¹H-NMR (CD₃OD, δ ppm): 0.90 (3H, t, J=7.2 Hz), 1.11-1.93 (32H, m), 2.07-2.21 (1H, m), 2.72-2.88 (1H, m)
Elemental analysis for $C_{20}H_{39}O_4P$:
Calculated: C 64.14%, H 10.50%.
Found: C 64.15%, H 10.48%.

EXAMPLE 38

(a) ethyl 3-cyclohexyl-2-(2,2-dimethylcyclopropyl)ethoxyphosphinoyl]methylpropionate (diastereomeric mixture)
Oil IR (neat, cm⁻¹) 2926, 1737, 1452, 1194, 1170, 1035, 948.
FAB-MS (m/e): 359 (M+H)⁺.
¹H-NMR (CDCl₃, δ ppm): 0.42-2.40 (30H, m), 2.90 (1H, m), 3.96-4.26 (4H, m).

(b) 3-cyclohexyl-2-[(2,2-dimethylcyclopropyl)hydroxyphosphinoyl]methylpropionic acid (one of the diastereomers)

m.p.: 160.5°–161° C.

IR (KBr, cm$^{-1}$) 3424, 2926, 1707, 1452, 1236, 1182, 978.

FAB-MS (m/e): 303 (M+H)$^+$.

$^1$H-NMR (CD$_3$OD, δ ppm): 0.62–1.90 (18H, m), 1.14 (3H, d, J=1.5 Hz), 1.23 (3H, s), 2.15 (1H, ddd, J=9.2 Hz, 11.2 Hz, 15.3 Hz), 2.75–2.95 (1H, m).

Elemental analysis for C$_{15}$H$_{27}$O$_4$P:
Calculated: C 59.59%, H 9.00%.
Found: C 59.48%, H 8.91%.

(c) 3-cyclohexyl-2-(2,2-dimethylcyclopropyl)hydroxyphosphinoyl)methylpropionic acid (the other diastereomer)

m.p.: 128°–130° C.

IR (KBr, cm$^{-1}$): 3424, 1725, 1452, 1173, 1137, 1122, 966.

FAB-MS (m/e): 303 (M+H)$^+$.

$^1$H-NMR (CD$_3$OD, δ ppm): 0.67–1.90 (18H, m), 1.16 (3H, d, J=2.1 Hz), 1.31 (3H, s), 2.17 (1H, ddd, J=9.1 Hz, 15.3 Hz, 15.3 Hz), 2.75–2.90 (1H, m).

Elemental analysis for C$_{15}$H$_{27}$O$_4$P:
Calculated: C 59.59%, H 9.00%.
Found: C 59.33%, H 8.98%.

EXAMPLE 39

Production of (Z)-6-dimethylamino-2-(hydroxyisobutylphosphinoyl)-methyl-2-hexenoic acid:

(a) Production of ethyl (Z)-6-dimethylamino-2-(ethoxyisobutylphosphinoyl)methyl-2-hexenoate Ethyl (Z)-6-chloro-2-(ethoxyisobutylphosphinoyl)methyl-2-hexenoate (300 mg; 0.89 millimole) was dissolved in 12 ml of 12.9% dimethylamine-tetrahydrofuran solution, and made to react at room temperature for 4 days. The solvent was evaporated under reduced pressure. The residue was dissolved in 30 ml of ethyl acetate, and the desired product was extracted with 30 ml of 3 N hydrochloric acid. Sodium hydrogen carbonate was added to the aqueous layer to adjust its pH to 8, and it was extracted three times with 20 ml of ethyl acetate each time. The organic layers were dried over anhydrous magnesium sulfate, and the solvent was evaporated under reduced pressure to give 160 mg (yield 52%) of the captioned compound as a pale yellow oil.

FAB-MS (m/e): 348 (M+H)$^+$.

$^1$H-NMR (CD$_3$OD, δ ppm): 1.06 (6H, d, J=6.6 Hz), 1.28 (3H, t, J=7.2 Hz), 1.30 (3H, t, J=7.2 Hz), 1.68–1.75 (4H, m), 2.02–2.17 (1H, m), 2.26 (6H, s), 2.31–2.40 (4H, m), 2.98–3.06 (2H, m), 3.95–4.11 (2H, m), 4.21 (2H, q, J=7.2 Hz), 6.95 (1H, dt, J5.1 Hz, 7.2 Hz).

(b) Production of (Z)-6-dimethylamino-2-(hydroxyisobutylphosphinoyl)methyl-2-hexenoic acid Ethyl (Z)-6-dimethylamino-2-(ethoxyisobutylphosphinoyl)methyl-2-hexenoate (125 mg; 0.36 millimole) was dissolved in 10 ml of 3 N hydrochloric acid, and heated under reflux for 11 hours. After cooling, the solvent was evaporated under reduced pressure. The residue was dissolved in water, and the solution was charged on a column (2.5×16 cm) of DOWEX 50W-X4 (50–100 mesh, H+) ion-exchange resin. The column was eluted with water until the eluate was no longer acidic (200 ml). The column was eluted with 2 N aqueous ammonia. Fractions containing the desired compound were combined, and evaporated under reduced pressure to give a pale yellow hygroscopic foam. This substance was dissolved in water, and the aqueous solution was charged onto a DOWEX 1X-8 (200–400 mesh, AcO$^-$) ion-exchange column (2.5×14 cm). The column was eluted with 150 ml of water, and then with 0.6 M acetic acid. Fractions containing the desired product were combined and evaporated under reduced pressure to give a pale yellow oil, which was triturated with ether to give 44 mg (yield 42%) of the captioned compound as a pale yellow amorphous powder.

IR (KBr, cm$^{-1}$): 2956, 1698, 1116, 1026.

High resolution FAB-MS
[m/e, for (C$_{13}$H$_{26}$NO$_4$P+H)$^+$].
Calculated: 292.1678.
Found: 292.1706.

$^1$H-NMR (CD$_3$OD, δ ppm): 1.07 (6H, d, J=6.6 Hz), 1.58 (2H, dd, J=6.6 Hz, 6.6 Hz), 1.99–2.14 (3H, m), 2.48–2.56 (2H, m), 2.79 (6H, s), 2.8–2.9 (2H, m), 3.09 (2H, t, J=6.6 Hz), 6.76 (2H, dt, J=5.1 Hz, 7.2 Hz).

EXAMPLE 40

Production of (Z)-6-carboxymethylmethylamino2-(hydroxyisobutylphosphinoyl)methyl-2-hexenoic acid (a) Production of ethyl (Z)-6-benzyloxycarbonylmethylmethylamino-2-(ethoxyisobutylphosphinoyl)-methyl-2-hexenoate A mixture of 360 mg (1.06 millimoles) of ethyl (Z)-6-chloro-2-(ethoxyisobutylphosphinoyl)methyl-2-hexenoate, 530 mg (2.97 millimoles) of sarcosine benzyl ester and 180 mg (1.20 millimoles) of sodium iodide in 5 ml of dimethylformamide was stirred at room temperature for 29 hours and at 60° C. for 3 hours. Water (25 ml) was added to the reaction mixture and the mixture was extracted twice with 35 ml of ethyl acetate each time. The combined organic layers were dried over anhydrous magnesium sulfate, and the solvent was evaporated under reduced pressure. The residue was purified by medium-pressure liquid chromatography [Lobar column (a product of E. Merck & Co.), size B, Lichroprep SI 60, dichloromethane-methanol (40:1)] to give 90 mg (yield 18%) of the captioned compound as a pale yellow oil.

FAB-MS (m/e): 482 (M+H)$^+$.

$^1$H-NMR (CDCl$_3$, δ ppm): 1.05 (6H, dd, J=3.0 Hz, 6.9 Hz), 1.27 (3H, t, J=6.9 Hz), 1.32 (3H, t, J=6.9 Hz), 1.60–1.71 (4H, m), 2.09–2.16 (1H, m), 2.29–2.36 (2H, m), 2.38 (3H, s), 2.54 (2H, t, J=7.5 Hz), 2.94 (2H, d, J=16.5 Hz), 3.31 (2H, s), 3.96–4.13 (2H, m), 4.22 (2H, q, J=6.9 Hz), 5.16 (2H, s), 6.93 (1H, dt, J=5.4 Hz, 7.5 Hz), 7.32–7.37 (5H, m).

(b) Production of (Z)-6-carboxymethylmethylamino-2-(hydroxyisobutylphosphinoyl)methyl-2-hexenoic acid Ethyl (Z)-6-benzyloxycarbonylmethylmethylamino-2-(ethoxyisobutylphosphinoyl)methyl-2-hexenoate (89 mg; 0.19 millimole) was dissolved in 1.3 ml of concentrated hydrochloric acid, and the solution was heated under reflux for 12 hours. After cooling, the reaction mixture was concentrated under reduced pressure. The residue was dissolved in water and charged onto a column (2.5×9 cm) of DOWEX 50W-X4 (50–100 mesh, H+ion-exchange resin). The column was eluted with water until the eluate became no longer acidic (100 ml), and then with 2 N aqeuous ammonia. Fractions containing the desired product were combined and evaporated under reduced pressure to give 60 mg (yield 94%) of the captioned compound as a pale yellow amorphous powder.

IR (KBr, cm$^{-1}$): 3418, 3190, 2962, 1635, 1404, 1128, 1029.

High-resolution FAB-MS

[m/e, for $(C_{14}H_{26}NO_6P+H)^+$].

Calculated: 336.1576.

Found: 336.1567.

$^1$H-HMR (CD$_3$OD, δ ppm): 1.04 (6H, d, J=6.9 Hz), 1.50 (2H, dd, J=6.9 Hz, 13.2 Hz), 1.93 (2H, tt, J=7.5 Hz, 7.5 Hz), 2.03–2.15 (1H, m), 2.39 (2H, ddt, J=3.3 Hz, 7.5 Hz, 7.5 Hz), 2.69 (2H, d, J=15.9 Hz), 2.89 (3H, s), 3.20 (2H, t, J=7.5 Hz), 3.62 (2H, s), 6.64 (1H, dt, J=5.1 Hz), 7.5 Hz).

EXAMPLE 41

Production of (Z)-8-dibutylamino-2-(hydroxyisobutylphosphinoyl)-methyl-2-octenoic acid hydrochloride (a) Production of ethyl (Z)-8-dibutylamino-2-(ethoxyisobutylphosphinoyl)methyl-2-octenoate A mixture of 367 mg (1.0 millimole) of ethyl (Z)-8-chloro-2-(ethoxyisobutylphosphinoyl)methyl)-2-octenoate and 150 mg (1.0 millimole) of sodium iodide in 1.7 ml (10 millimoles) of dibutylamine was stirred at 60° C. for 28 hours. The reaction mixture was diluted with 10 ml of water, and acidified to a pH of 1 with 6 N hydrochloric acid, and extracted with 20 ml of ethyl acetate. Sodium hydrogen carbonate was added to the aqueous layer to adjust its pH to 9. The mixture was extracted five times with 20 ml of ethyl acetate each time. The combined organic layers were washed twice with 10 ml of water each time, and dried over anhydrous magnesium sulfate. The solvent was evaporated under reduced pressure to give 316 mg (yield 69%) of the captioned compound as a pale yellow oil.

IR (neat, cm$^{-1}$): 2956, 1713, 1251, 1176, 1095, 954.

FAB-MS (m/e): 460 (M+H)$^+$.

$^1$H-NMR (CDCl$_3$, δ ppm): 0.90 (6H, t, J=7.0 Hz), 1.04 (6H, dd, J=3.5 Hz, 6.5 Hz), 1.27 (3H, t, J=6.9 Hz), 1.30 (3H, t, J=7.0 Hz), 1.23–1.53 (14H, m), 1.62 (2H, dd, J=6.7 Hz, 12.5 Hz), 2.05–2.18 (1H, m), 2.25–2.42 (8H, m), 2.92 (2H, d, J=16.6 Hz), 3.95–4.15 (2H, m), 4.21 (2H, q, J=7.0 Hz), 6.92 (1H, dt, J=5.2 Hz, 7.7 Hz).

(b) Production of (Z)-8-dibutylamino-2-(hydroxyisobutylphosphinoyl)methyl-2-octenoic acid hydrochloride Ethyl (Z)-8-dibutylamino-2-(ethoxyisobutylphosphinoyl)methyl-2-octenoate (200 mg; 0.43 millimole) was dissolved in 5 ml of concentrated hydrochloric acid, and the solution was stirred at 90° C. for 5.5 hours. After cooling, the reaction mixture was concentrated under reduced pressure. The residue was purified by medium-pressure liquid chromatography [Lobar column (a product of E. Merck & Co.), size B, Lichroprep RP-18, methanol/water (7:3)] to give 178 mg (yield 94%) of the captioned compound as a pale yellow oil.

IR (neat, cm$^{-1}$): 3412, 2962, 1704, 1236, 1161, 945.

High-resolution FAB-MS

[m/e, for $(C_{21}H_{42}NO_4P+H)^+$].

Calculated: 404.2930.

Found: 404.2953.

$^1$H-NMR (CD$_3$OD, δ ppm): 1.01 (6H, t, J=7.0 Hz), 1.04 (6H, d, J=6.6 Hz), 1.38–1.80 (16H, m), 2.04–2.18 (1H, m), 2.32–2.41 (2H, m), 2.93 (2H, d, J=17.1 Hz), 3.10–3.16 (6H, m), 6.98 (1H, dt, J=4.8 Hz, 7.2 Hz).

EXAMPLE 42

Production of (Z)-2-(hydroxyisobutylphosphinoyl)methyl-6-phenylthio-2-hexenoic acid (a) Production of ethyl (Z)-2-(ethoxyisobutylphosphinoyl)methyl-6-phenylthio-2-hexenoate Under an argon atmosphere, 62 μl (0.60 millimole) of thiophenol and 83 mg (0.60 millimole) of potassium carbonate were added to a solution of 169 mg (0.50 millimole) of ethyl (Z)-6-chloro-2-(ethoxyisobutylphosphinoyl)methyl-2-hexenoate in 1.0 ml of dimethylformamide, and the mixture was stirred at room temperature for 2 hours. Water (20 ml) was added to the reaction mixture, and it was extracted three times with 15 ml of ethyl acetate each time. The combined organic layers were washed with 10 ml of a saturated aqueous solution of sodium hydrogen carbonate and 10 ml of a saturated aqueous solution of sodium chloride, and dried over anhydrous magnesium sulfate. The solvent was evaporated under reduced pressure, and the residue was purified by "dry-column" flash chromatography [15 g of silica gel 60 made by E. Merck & Co.; hexane-ethyl acetate (0→100%) gradient elution] to give 202 mg (yield 98%) of the captioned compound as a pale yellow oil.

FAB-MS (m/e): 413 (M+H)$^+$.

$^1$H-NMR (CDCl$_3$, δ ppm): 1.04 (6H, dd, J=2.7 Hz, 6.3 Hz), 1.27 (3H, t, J=7.2 Hz), 1.30 (3H, t, J=7.2 Hz), 1.63 (2H, dd, J=6.9 Hz, 12.6 Hz), 1.83 (2H, tt, J=7.5 Hz, 7.5 Hz), 2.10 (1H, m), 2.47 (2H, ddt, J=4.2 Hz, 7.5 Hz, 7.5 Hz), 2.93 (2H, d, J=16.2 Hz), 2.95 (2H, t, J=7.5 Hz), 4.02 (2H, m), 4.21 (2H, q, J=7.2 Hz), 6.90 (1H, dt, J=5.1 Hz, 7.5 Hz), 7.14–7.38 (5H, m).

(b) Production of (Z)-2-(hydroxyisobutylphosphinoyl)methyl-6-phenylthio-2-hexenoic acid Concentrated hydrochloric acid (5 ml) was added to a solution of 155 mg (0.376 millimole) of ethyl (Z)-2-(ethoxyisobutylphosphinoyl)methyl-6-phenylthio-2-hexenoate in 5 ml of dioxane, and the solution was stirred for 3 hours under reflux. After cooling, the solvent was evaporated under reduced pressure. The residue was purified by preparative thin-layer chormatography [silica gel 60 F254 made by E. Merck & Co.; chloroform-methanol-acetic acid (9:1:1], and then recrystallized from ethyl acetate-hexane (1.3) to give 74 mg (yield 55%) of the captioned compound as colorless crystals.

m.p.: 115.5°–117° C.

IR (KBr, cm$^{-1}$): 2962, 1689, 1245, 1170, 966.

FAB-MS (m/e): 357 (M+H)$^+$.

$^1$H-NMR (CD$_3$OD, δ ppm): 1.05 (6H, d, J=6.3 Hz), 1.64 (2H, dd, J=6.6 Hz, 12.9 Hz), 1.79 (2H, tt, J=7.5 Hz, 7.5 Hz), 2.10 (1H, m), 2.46 (2H, ddt, J=3.9 Hz), 7.5 Hz, 7.5 Hz), 2.92 (2H, d, J=17.4 Hz), 2.98 (2H, t, J=7.5 Hz), 6.93 (1H, dt, J=5.1 Hz, 7.5 Hz), 7.13–7.35 (5H, m).

Elemental analysis for $C_{17}H_{25}O_4PS$:

Calculated: C 57.29%, H 7.07%.

Found: C 57.18%, H 7.37%.

EXAMPLE 43

Production of (Z)-2-(hydroxyisobutylphosphinoyl)methyl-6-(1,2,3-triazol-4-yl)thio-2-hexenoic acid (a) Production of ethyl (Z)-2-(ethoxyisobutylphosphinoyl)methyl-6-(1,2,3-triazol-4-yl)thio-2-hexanoate To a solution of 339 mg (1.0 millimole) of ethyl (Z)-6-chloro-2-(ethoxyisobutylphosphinoyl)methyl-2-hexenoae in 2 ml of dimethylformamide was added 265 mg (1.2 millimoles) of 4-mercapto-1,2,3-triazole disodium salt hexahydrate, and the mixture was stirred at room temperature for 2.5 hours. Water (20 ml) was added to the reaction mixture. The pH of the mixture was adjusted to pH 7 with 6 N hydrochloric acid, and extracted three times with 10 ml of ethyl acetate each time. The organic layers were combined and washed with 5 ml of a saturated aqueous solution of sodium chloride, and dried over anhydrous magnesium sulfate. The solvent was evaporated under reduced pressure, and the residue was purified by "dry-column" flash chromatography [15 g of silica gel 60 made by E. Merck & Co.; hexane-ethyl acetate (50→100%) gradient elution] to give 341 mg (yield 85%) of the captioned compound as a colorless oil.

FAB-MS (m/e): 404 $(M+H)^+$.

$^1$H-NMR (DMSO-d$_6$, δ ppm): 0.97 (6H, dd, J=2.1 Hz, 6.6 Hz), 1.16 (3H, t, J=7.2 Hz), 1.22 (3H, t, J=7.2 Hz), 1.57 (2H, dd, J=6.6 Hz, 13.2 Hz), 1.69 (2H, tt, J=7.5 Hz, 7.5 Hz), 1.85–2.05 (1H, m), 2.36 (2H, ddt, J=3.6 Hz, (7.5 Hz, (7.5 Hz), 2.80–2.97 (4H, m), 3.90 (2H, m), 4.13 (2H, q, J=7.2 Hz), 6.76 (1H, dt, J=4.8 Hz, 7.5 Hz), 7.95 (1H, bs).

(b) Production of (Z)-2-(hydroxyisobutylphosphinoyl)-methyl-6-(1,2,3-triazol-4-yl)thio-2-hexenoic acid Ten milliliters of a 1.5 N aqueous solution of lithium hydroxide was added to a solution of 243 mg (0.60 millimole) of ethyl (Z)-2-(ethoxyisobutylphosphinoyl)-methyl-6-(1,2,3-triazol-4-yl)thio-2-hexenoate in 5 ml of methanol, and the mixture was heated under reflux for 8 hours. After cooling, the methanol was evaporated under reduced pressure. A 10% aqueous solution of citric acid was added to the residue to adjust its pH to 2, and sodium chloride was added to be saturated. The solution was extracted three times with 30 ml of ethyl acetate each time. The combined organic layers were washed with 10 ml of a saturated aqueous solution of sodium chloride, and dried over anhydrous magnesium sulfate. The solvent was evaporated under reduced pressure. The residue was purified by medium-pressure liquid chromatography [Lobar column (a product of E. Merck & Co.), size B, Lichroprep RP-18, 0.1 M acetic acid-methanol (50:50] to give 140 mg (yield 67%) of the captioned compound as a colorless vitreous substance.

IR (KBr, cm$^{-1}$): 3142, 2962, 1698, 1239, 1146, 1059, 969.

High-resolution FAB-MS
[m/e, for $(C_{13}H_{22}N_3O_4PS+H)^+$].
Calculated: 348.1147.
Found: 348.1191.

$^1$H-NMR (CD$_3$OD, δ ppm): 1.05 (6H, d, J=6.6 Hz), 1.65 (2H, dd, J=6.6 Hz, 12.9 Hz), 1.78 (2H, tt, J=7.5 Hz, 7.5 Hz), 2.10 (1H, m), 2.46 (2H, ddt, J=4.2 Hz, 7.5 Hz, 7.5 Hz), 2.94(2H, d, J=17.1 Hz), 2.95 (2H, t, J=7.5 Hz), 6.94 (1H, dt, J=5.1 Hz, 7.5 Hz). 7.86 (1H, s).

EXAMPLE 44

(a) Production of (Z)-8-carboxymethylthio-2-(hydroxyisobutylphosphinoyl)methyl-2-octenoic acid (Z)-8-chloro-2-(hydroxyisobutylphosphinoyl)methyl-2-octenoic acid was dissolved in 1.5 ml of a 1 N aqueous solution of sodium hydroxide, and 42 μl (0.38 millimole) of ethyl thioglycollate was added. The mixture was stirred at room temperature for 3 days. Water (10 ml) was added to the reaction mixture, and 3.5 N hydrochloric acid was added to make the mixture strongly acidic. The mixture was extracted three times with 20 ml of ethyl acetate each time. The combined organic layers were washed with a saturated aqueous solution of sodium chloride, and dried over anhydrous magnesium sulfate. The solvent was evaporated under reduced pressure to give 115 mg (yield 98%) of the captioned compound as a colorless oil.

IR (neat, cm$^{-1}$), 2932, 1713, 1281, 1242, 1218, 1143, 948.

High-resolution FAB-MS
[m/e, for $(C_{15}H_{27}O_6PS+H)^+$].
Calculated: 367.1344.
Found: 367.1371.

$^1$H-NMR (CD$_3$OD, δ ppm): 1.05 (6H, d, J=6.6 Hz), 1.45–1.53 (4H, m), 1.64 (2H, dd, J=6.6 Hz, 12.9 Hz), 2.06–2.14 (1H, m), 2.29–2.36 (2H, m), 2.65 (2H, t, J=7.5 Hz), 2.91 (2H, d, J=17.1 Hz), 3.21 (2H, s), 6.96 (1H, dt, J=5.4 Hz, 7.2 Hz).

(b) Production of (Z)-2-(hydroxyisobutylphosphinoyl)-methyl-8-methoxycarbonylmethylthio-2-octenoic acid (Z)-8-carboxymethylthio-2-(hydroxyisobutylphosphinoyl)methyl-2-octenoic acid (366 mg; 1 millimole) was dissolved in 10 ml of dry methanol, and the solution was concentrated at 40° C. under reduced pressure. This procedure was further repeated twice. The resulting pale yellow oily residue was purified by medium-pressure liquid chromatography [Lobar column (a product of E. Merck & Co.), size B, Lichroprep RP-18, 0.1 M acetic acid/methanol (70:30)]to give 80 mg (yield 21%) of the captioned compound as a colorless oil.

IR (neat, cm$^{-1}$): 2932, 1740, 1700, 1281, 1143, 951.
High-resolution FAB-MS
[m/e, for $(C_{16}H_{29}O_6PS+H)^+$].
Calculated: 381.1501.
Found: 381.1537.

$^1$H-NMR (CD OD, δ ppm): 1.05 (6H, d, J=6.6 Hz), 1.43–1.58 (4H, m), 1.63 (2H, dd, J=6.6 Hz, 13.2 Hz), 2.04–2.14 (1H, m), 2.28–2.37 (2H, m), 2.63 (2H, t, J=7.2 Hz), 2.91 (2H, d, J=17.1 Hz), 3.25 (2H, s), 3.70 (3H, s), 6.97 (1H, dt, J=5.4 Hz, 7.5 Hz).

EXAMPLES 45–50

The following compounds (Examples 45 to 50) were prepared in a similar manner as in Example 42.

EXAMPLE 45

(a) ethyl (Z)-2-(ethoxyisobutylphosphinoyl)methyl-6-(3-hydroxy-2-pyridyl)thio-2-hexenoate
Oil
FAB-MS (m/e): 430 $(M+H)^+$.

$^1$H-NMR (CDCl$_3$, δ ppm): 1.04 (6H, dd, J=1.0 Hz, 6.3 Hz), 1.26 (3H, t, J=7.2 Hz), 1.30 (3H, t, J=7.2 Hz), 1.66 (2H, dd, J=6.9 Hz, 12.9 Hz), 1.84 (2H, tt, J=7.2 Hz, 7.2 Hz), 2.00–2.20 (1H, m), 2.47 (2H, ddt, J=3.9 Hz, 7.2 Hz, 7.2 Hz), 2.93 (2H, d, J=16.5 Hz), 3.17 (2H, t, J=7.2 Hz), 3.90–4.15 (2H, m), 4.21 (2H, q, J=7.2 Hz), 6.93 (1H, dt, J=5.1 Hz, 7.2 Hz), 6.96 (1H, dd, J=4.5 Hz, 8.1 Hz), 7.12 (1H, dd, J=1.2 Hz, 8.1 Hz), 8.05 (1H, dd, J=1.2 Hz, 4.5 Hz).

(b) (Z)-2-(hydroxyisobutylphosphinoyl)methyl-6-(3-hydroxy-2-pyridyl)thio-2-hexenoic acid
m.p.: 164°–166.5° C.
IR (KBr, cm$^{-1}$) 3412, 2956, 1701, 1455, 1305, 1269, 1257, 1011.
FAB-MS (m/e): 374 $(M+H)^+$.

¹H-NMR (CD₃OD, δ ppm): 1.03 (6H, d, J=6.6 Hz), 1.62 (2H, dd, J=6.6 Hz, 12.9 Hz), 1.84 (2H, tt, J=7.2 Hz, 7.2 Hz), 2.00–2.20 (1H, m), 2.46 (2H, ddt, J=3.9 Hz, 7.2 Hz, 7.2 Hz), 2.90 (2H, d, J=17.1 Hz), 3.16 (2H, t, J=7.2 Hz), 6.97 (1H, dt, J=5.4 Hz, 7.2 Hz), 6.93 (1H, dd, J=4.5 Hz, 7.8 Hz), 6.99 (1H, dd, J=1.8 Hz, 7.8 Hz), 7.92 (1H, dd, J=1.8 Hz, 4.5 Hz).

Elemental analysis for C₁₄H₂₄NO₅PS:
Calculated: C 51.47%, H 6.48%, N 3.75%.
Found: C 51.79%, H 6.65% N 3.93%.

EXAMPLE 46

(a) ethyl (Z)-6-[(L)-2-amino-2-methoxycarbonylethyl]thio-2-(ethoxyisobutylphosphinoyl)methyl-2-hexenoate
Oil
FAB-MS (m/e): 438 (M+H)⁺.
¹H-NMR (CDCl₃, δ ppm): 1.05 (6H, dd, J=3.0 Hz, 6.6 Hz), 1.28 (3H, t, J=7.2 Hz), 1.31 (3H, t, J=7.2 Hz), 1.63 (2H, dd, J=6.6 Hz, 12.6 Hz), 1.78 (2H, tt, J=7.2 Hz, 7.2 Hz), 2.00–2.20 (1H, m), 2.43 (2H, ddt, J=3.9 Hz, 7.2 Hz, 7.2 Hz), 2.58 (2H, t, J=7.2 Hz), 2.77 (1H, dd, J=7.2 Hz, 13.5 Hz), 2.92 (1H, dd, J=4.8 Hz, 13.5 Hz), 2.93 (2H, d, J=16.2 Hz), 3.65 (1H, dd, J=4.8 Hz, 7.2 Hz), 3.75 (3H, s), 3.90–4.15 (2H, m), 4.22 (2H, q, J=7.2 Hz), 6.90 (1H, dt, J=5.1 Hz, 7.2 Hz).

(b) (Z)-6-(L)-2-amino-2-carboxyethyl]thio-2-(hydroxyisobutylphosphinoyl)methyl-2-hexenoic acid
Amorphous white powder
IR (KBr, cm⁻¹) 3456, 2962, 1698, 1641, 1251, 1143, 1059, 966.
High-resolution FAB-MS
[m/e, for (C₁₄H₂₆NO₆PS+H)⁺].
Calculated: 368.1297.
Found: 368.1341.
[α]$_D^{20}$: −9.01 (C 1.08, CH₃OH).
¹H-NMR (CD₃OD, δ ppm): 1.05 (6H, d, J=6.6 Hz), tt, J=7.5 Hz, 7.5 Hz), 2.00–2.20 (1H, m), 2.43 (2H, ddt, J=3.6 Hz, 7.5 Hz, 7.5 Hz), 2.66 (2H, t, J=7.5 Hz), 2.89 (2H, d, J=16.8 Hz), 2.97 (1H, dd, J=8.1 Hz, 14.7 Hz), 3.17 (1H, dd, J=3.9 Hz, 14.7 Hz), 3.94 (1H, dd, J=3.9 Hz, 8.1 Hz), 6.91 (1H, dt, J=5.1 Hz, 7.5 Hz).

EXAMPLE 47

(a) ethyl (Z)-6-(2-aminoethyl)thio-2-(ethoxyisobutylphosphinoyl)methyl-2-hexenoate
Oil
FAB-MS (m/e): 380 (M+H)⁺.
¹H-NMR (CDCl₃, δ ppm): 1.00–1.10 (6H, m), 1.25–1.35 (6H, m), 1.58–1.90 (4H, m), 2.00–2.20 (1H, m), 2.40–2.70 (6H, m), 2.70–3.00 (4H, m), 3.90–4.30 (4H, m), 6.91 (1H, m).

(b) (Z)-6-(2-aminoethyl)thio-2-(hydroxyisobutylphosphinoyl)methyl-2-hexenoate
White foam
IR (KBr, cm⁻¹) 3412, 2956, 1695, 1641, 1122, 1020, 954.
High-resolution FAB-MS
[m/e, for (C₁₃H₂₆NO₆PS+H)⁺].
Calculated: 324.1398.
Found: 324.1379.
¹H-NMR (CD OD, δ ppm): 1.04 (6H, d, J=6.6 Hz), 1.52 (2H, dd, J=6.9 Hz, 12.9 Hz), 1.81 (2H, tt, J=7.5 Hz, 7.5 Hz), 2.00–2.20 (1H, m), 2.40 (2H, ddt, J=3.6 Hz, 7.5 Hz, 7.5 Hz), 2.63 (2H, t, J=7.5 Hz), 2.70 (2H, d, J=16.2 Hz), 2.80 (2H, t, J=6.9 Hz), 3.10 (2H, t, J=6.9 Hz), 6.72 (1H, dt, J=4.8 Hz, 7.5 Hz).

EXAMPLE 48

(a) ethyl (Z)-2-(ethoxyisobutylphosphinoyl)methyl-6-(2-hydroxyethyl)thio-2-hexenoate
Oil
IR (neat, cm⁻¹) 3388, 2962, 1713, 1290, 1257, 1176, 1038, 954.
FAB-MS (m/e): 381 (M+H)⁺.
¹H-NMR (CDCl₃, δ ppm): 1.04 (6H, dd, J=2.4 Hz, 6.6 Hz), 1.28 (3H, t, J=7.2 Hz), 1.31 (3H, t, J=7.2 Hz), 1.65 (2H, dd, J=6.6 Hz, 12.9 Hz), 1.81 (2H, tt, J=7.2 Hz, 7.2 Hz), 2.04–2.15 (1H, m), 2.40–2.49 (2H, m), 2.60 (2H, tt, J=7.2 Hz, 7.2 Hz), 2.73 (2H, t, J=6.3 Hz), 2.94 (2H, d, J=15.6 Hz), 3.73 (2H, t, J=6.3 Hz), 3.97–4.12 (2H, m), 4.22 (2H, q, J=7.2 Hz), 6.94 (1H, dt, J=5.1 Hz, 7.8 Hz).

(b) (Z)-6-(2-hydroxyethyl)thio-2-(hydroxyisobutylphosphinoyl)methyl-2-hexenoate
Oil
IR (neat, cm⁻¹) 3200, 2926, 1704, 1257, 1143, 1059, 948.
High-resolution FAB-MS
[m/e, for (C₁₃H₂₅O₅PS+H)⁺].
Calculated: 325.1239.
Found 325.1284.
¹H-NMR (CD OD, δ ppm): 1.05 (6H, d, J=6.3 Hz), 1.63 (2H, dd, J=6.6 Hz, 12.9 Hz), 1.77 (2H, tt, J=7.8 Hz, 7.8 Hz), 2.07–2.15 (1H, m), 2.38–2.47 (2H, m), 2.60 (2H, t, J=7.5 Hz), 2.65 (2H, t, J=6.9 Hz), 2.91 (2H, d, J=16.8 Hz), 3.67 (2H, t, J=6.9 Hz), 6.92 (1H, dt, J=5.4 Hz, 7.8 Hz).

EXAMPLE 49

(a) ethyl (Z)-2-(ethoxyisobutylphosphinoyl)methyl-6-(1-methylimidazol-2-yl)thio-2-hexenoate
Oil
IR (neat, cm⁻¹) 2962, 1713, 1281, 1257, 1176, 1038, 957.
FAB-MS (m/e): 417 (M+H)⁺.
¹H-NMR (CDCl₃, δ ppm): 1.04 (6H, dd, J=3.0 Hz, 6.3 Hz), 1.27 (3H, t, J=7.2 Hz), 1.30 (3H, t, J=7.2 Hz), 1.63 (2H, dd, J=6.9 Hz, 12.6 Hz), 1.87 (2H, tt, J=7.5 Hz, 7.5 Hz), 2.05–2.15 (1H, m), 2.41–2.50 (2H, m), 2.92 (2H, d, J=16.5 Hz), 3.08 (2H, t, J=7.2 Hz), 3.62 (3H, s), 3.95–4.12 (2H, m), 4.21 (2H, q, J=7.2 Hz), 6.90 (1H, dt, J=5.1 Hz, 7.5 Hz), 6.92 (1H, d, J=1.2 Hz), 7.05 (1H, d, J=1.2 Hz).

(b) (Z)-2-(hydroxyisobutylphosphinoyl)methyl-6-(1-methylimidazol-2-yl)thio-2-hexenoic acid
Oil
IR (neat, cm⁻¹) 2962, 1695, 1278, 1131.
High-resolution FAB-MS
[m/e, for (C₁₅H₂₅N₂O₄PS+H)⁺].
Calculated: 361.1351.
Found: 361.1390.
¹H-NMR (CD₃OD, δ ppm): 1.05 (6H, d, J=7.5 Hz), 1.58 (2H, dd, J=6.6 Hz, 13.2 Hz), 1.81 (2H, tt, J=7.2 Hz, 7.2 Hz), 2.08–2.16 (1H, m), 2.46–2.52 (2H, m), 2.81 (2H, d, J=16.5 Hz), 3.11 (2H, t, J=7.2 Hz), 3.83 (3H, s), 6.77 (1H, dt, J=4.8 Hz, 7.5 Hz), 7.34 (1H, d, J=1.8 Hz), 7.45 (1H, d, J=1.8 Hz).

EXAMPLE 50

(a) ethyl (Z)-2-(ethoxyisobutylphosphinoyl)methyl-8-(3-hydroxy-2-pyridyl)thio-2-octenoate
Oil
IR (neat, cm ): 2932, 1713, 1452, 1275, 1185, 1038, 960.

FAB-MS (m/e): 458 (M+H)+.

¹H-NMR (CDCl₃, δ ppm): 1.04 (6H, dd, J=2.5 Hz, 7.0 Hz), 1.28 (3H, t, J=7.0 Hz), 1.31 (3H t, J=7.0 Hz), 1.48 (4H, m), 1.50–1.65 (4H, m), 2.10 (1H, m), 2.29 (2H, m), 2.93 (2H, d, J=16.7 Hz), 3.12 (2H, t, J=7.3 Hz), 4.09 (2H, m), 4.20 (2H, m), 6.91 (1H, dt, J=4.9 Hz, 7.5 Hz), 7.00 (1H, dd, J=4.6 Hz, 8.1 Hz), 7.15 (1H, dd, J=1.9 Hz, 8.1 Hz), 8.09 (1H, dd, J=1.9 Hz, 4.6 Hz).

(Z)-2-(hydroxyisobutylphosphinoyl)methyl-8-(3-hydroxy-2-pyridyl)thio-2-octenoic acid Oil IR (neat, cm⁻¹): 2932, 1695, 1458, 1308, 1143, 954.

High-resolution FAB-MS

[m/e, for (C₁₈H₂₈O₅NPS+H)+].

Calculated: 402.1504.

Found: 402.1519.

¹H-NMR (CD OD, δ ppm): 1.05 (6H, d, J=6.6 Hz), 1.54 (4H, m), 1.65 (2H, dd, J=6.5 Hz, 12.9 Hz), 1.74 (2H, m), 2.12 (1H, m), 2.33 (2H, m), 2.92 (2H, d, J=17.1 Hz), 3.23 (2H, t, J=6.5 Hz), 6.97 (1H, dt, J=5.5 Hz, 7.3 Hz), 7.34 (1H, dd, J=4.7 Hz, 8.3 Hz), 7.42 (1H, d, J=8.3 Hz), 8.05 (1H, d, J=4.7 Hz).

EXAMPLE 51

Production of ethyl (Z)-3-cyclohexyl-2-(hydroxyisobutylphosphinoyl)methylpropenoate A solution of 107 mg (0.31 millimole) of ethyl (Z)-3-cyclohexyl-2-(ethoxyisobutylphosphinoyl)methylpropenoate in 1.0 ml of 4N HCl-butyl acetate was heated in a sealed tube at 100° C for 2 hours. After cooling, the solvent was evaporated under reduced pressure, and the residue was purified by "dry-column" flash chromatography 15 g of silica gel 60 made by E. Merck & Co.; chloroform-methanol-acetic acid (50:1:1)] to give 91 mg (yield 94%) of the captioned compound as a colorless oil.

IR (neat, cm⁻¹) 2932, 1710, 1227, 1155, 1059, 972.

High-resolution FAB-MS

[m/e, for (C₁₆H₂₉O₄P+H)+].

Calculated: 317.1882.

Found: 317.1919.

¹H-NMR (CD OD, δ ppm): 1.05 (6H, d, J=6.9 Hz), 1.09–1.79 (10H, m), 1.29 (3H, t, J=7.5 Hz), 1.63 (2H, dd, J=6.9 Hz, 12.9 Hz), 2.04–2.14 (1H, m), 2.43–2.52 (1H, m), 2.91 (2H, d, J=16.8 Hz), 4.19 (2H, q, J=6.9 Hz), 6.71 (1H, dd, J=5.1 Hz, 10.8 Hz).

EXAMPLE 52

Production of ethyl (Z)-3-cyclohexyl-2-(hydroxyisobutylphosphinoyl)methylpropenoate (Z)-3-cyclohexyl-2-(hydroxyisobutylphosphinoyl)-methylpropenoic acid (150 mg; 0.52 millimole) was dissolved in 10 ml of 8 N HCl-ethanol, and the solution was heated under reflux for 2 hours. After cooling, the mixture was evaporated under reduced pressure. The residue was purified by "dry-column" flash chromatography [15 g of silica gel 60 made by E. Merck & Co.; chloroform-methanol-acetic acid (50:1:1)) to give 130 mg (yield 79% of the captioned compound as a colorless oil. The IR and 1H-NMR data of this compound were identical with those of the product obtained in Example 51.

EXAMPLE 53

Production of methyl (Z)-3-cyclohexyl-2-(hydroxyisobutylphosphinoyl)methylpropenoate (Z)-3-cyclohexyl-2-(hydroxyisobutylphosphinoyl)-methylpropenoic acid was treated in a similar manner as in Example 52 except that HCl-methanol was used instead of HCl-ethanol used in Example 52. The captioned compound was obtained as a colorless oil.

IR (neat, cm⁻¹) 2932, 1716, 1281, 1227, 1155, 1062, 975.

High-resolution FAB-MS

[m/e, for (C₁₅H₂₇O₄P+H)+].

Calculated: 303.1725.

Found: 303.1714.

¹H-NMR (CD₃OD, δ ppm): 1.05 (6H, d, J=6.9 Hz), 1.10–1.45 (6H, m), 1.63 (2H, dd, J=6.5 Hz, 12.8 Hz), 1.70–1.80 (4H, m), 2.10 (1H, m), 2.48 (1H, m), 2.92 (2H, d, J=16.5 Hz), 3.73 (3H, s), 6.72 (1H, dd, J=5.3 Hz, 10.7 Hz).

EXAMPLE 54

Production of (Z)-3-cyclohexyl-2-(ethoxyisobutylphosphinoyl)methylpropenoic acid To a solution of 176 mg (0.51 millimole) of ethyl (Z)-3-cyclohexyl-2-(ethoxyisobutylphosphinoyl)methylpropenoate in 2 ml of ethanol was added 1 N sodium hydroxide (0.51 ml) and the solution was stirred at room temperature for 3 hours, and then refluxed for 30 minutes. After cooling, the reaction mixture was diluted with 30 ml of water, and extracted with 20 ml of ether. The aqueous layer was acidified with 4 N hydrochloric acid, and extracted three times with 20 ml of ether each time. The combined organic layers were washed with 10 ml of a saturated aqueous solution of sodium chloride, and dried over anhydrous magnesium sulfate. The solvent was evaporated under reduced pressure to give 143 mg (yield of the captioned compound as a colorless oil.

IR (neat, cm): 2932, 2854, 1701, 1236, 1149, 1035, 966.

FAB-MS (m/e): 317 (M+H)+.

¹H-NMR (CD OD, δ ppm): 1.05 (6H, d, J=6.6 Hz), 1.10–1.45 (6H, m), 1.29 (3H, t, J=6.9 Hz), 1.65–1.71 (6H, m), 2.10 (1H, m), 2.35–2.51 (1H, m), 2.98 (2H, d, J=16.8 Hz), 3.95–4.15 (2H, m), 6.74 (1H, dd, J=5.1 Hz, 10.5 Hz).

EXAMPLE 55

Production of pivaloyloxymethyl (Z)-3-cyclohexyl-2-(hydroxyisobutylphosphinoyl)methylpropenoate To a solution of 100 mg (0.347 millimole) of (Z)-3-cyclohexyl-2-(hydroxyisobutylphosphinoyl)methylpropenoic acid in 1.0 ml of dimethylformamide were added 130 μl (0.87 millimole) of 1,8-diazabicyclo[5,4,0]-7-undecene and 75 μl (0.52 millimole) of chloromethyl pivalate, and the mixture was stirred at room temperature for 21 hours. Fifty milliliters of a saturated aqueous solution of ammonium chloride was added to the reaction mixture, and the mixture was extracted three times with 30 ml of ethyl acetate each time. The combined organic layers were washed with 10 ml of a saturated aqueous solution of sodium chloride, and dried over anhydrous magnesium sulfate. The solvent was evaporated under reduced pressure, and the residue was purified by preparative thin-layer chromatography silica gel 60 F254 made by E. Merck & Co.; dichloromethane/methanol/acetic acid [30:1:1)] to give 90 mg (yield 64%) of the captioned compound as a colorless oil.

IR (neat, cm$^{-1}$): 2932, 1755, 1731, 1158, 1119, 1029, 978,

High-resolution FAB-MS
[m/e, for $(C_{20}H_{35}O_6P+H)^+$].
Calculated: 403.2249.
Found: 403.2201.

$^1$H-NMR (CD$_3$OD, δ ppm): 1.10–1.46 (6H, m), 1.19 (9H, s), 1.60–1.80 (6H, m), 2.10 (1H, m), 2.53 (1H, m), 2.92 (2H, d, J=16.5 Hz), 5.18 (2H, s), 6.80 (1H, dd, J=4.7 Hz, 10.7 Hz).

EXAMPLE 56

Production of phthalidyl (Z)-3-cyclohexyl-2-(hydroxyisobutylphosphinoyl)methylpropenoate.

(a) Production of phthalidyl (Z)-3-cyclohexyl-2-(ethoxyisobutylphosphinoyl)methylpropenoate To a solution of 80 mg (0.25 millimole) of (Z)-3-cyclohexyl-2-(ethoxyisobutylphosphinoyl)methylpropenoic acid in 0.80 ml of dimethylformamide were added 112 μl (0.75 millimole) of 1,8-diazabicyclo5,4,0]-7undecene and 107 mg (0.50 millimole) of 3-bromophthalide, and the mixture was stirred at room temperature for 28 hours. Water (15 ml) was added to the reaction mixture, and the mixture was extracted three times with 15 ml of ethyl acetate each time. The organic layers were combined and washed with 10 ml of a saturated aqueous solution of sodium chloride and dried over anhydrous magnesium sulfate. The solvent was evaporated under reduced pressure, and the residue was purified by preparative thin-layer chromatography [silica gel 60 F254 made by E. Merck & Co.; dichloromethane/methanol (30:1)] to give 50 mg (yield 45%) of the captioned compound as a colorless oil.

(b) Production of phthalidyl (Z)-3-cyclohexyl-2-(hydroxyisobutylphosphinoyl)methylpropenoate Under an atmosphere of argon, 29 μl (0.22 millimole) of bromotrimethylsilane was added to a solution of 48 mg (0.11 millimole) of phthalidyl (Z)-3-cyclohexyl-2-(ethoxyisobutylphosphinoyl)methylpropenoate in 0.50 ml of dry dichloromethane, and the mixture was stirred at room temperature for 18 hours. To the reaction mixture were added 2.0 ml of ethyl acetate and 3.0 ml of a saturated aqueous solution of ammonium chloride, and the mixture was stirred at room temperature for 30 minutes. A saturated aqueous solution of ammonium chloride (3 ml) was added to the reaction mixture, and the mixture was extracted three times with 8 ml of ethyl acetate each time. The combined organic layers were dried over anhydrous magnesium sulfate, and the solvent was evaporated under reduced pressure. The residue was purified by preparative thin-layer chromatography [silica gel 60 F254 made by E. Merck & Co.; dichloromethane/methanol/acetic acid (30:1:1)]to give 16 mg (yield 35%) of the captioned compound as a colorless oil. On standing, this compound solidified.

m.p.: 64.5°–67.5° C.

IR (neat, cm$^{-1}$) 2932, 1794, 1734, 1218, 1146, 1053, 975.

High-resolution FAB-MS
[m/e, for $(C_{22}H_{29}O_6P+H)^+$].
Calculated: 421.1780.
Found: 421.1816.

$^1$H-NMR (CD$_3$OD,δ ppm): 1.04 (6H, dd, J=1.2 Hz, 6.6 Hz), 1.06–1.77 (10H, m), 1.63 (2H, dd, J=6.9 Hz, 12.9 Hz), 2.00–2.20 (1H, m), 2.45–2.60 (1H, m), 2.94 (2H, d, J=15.9 Hz), 6.79 (1H, dd, J=4.8 Hz, 10.2 Hz), 7.53 (1H, s), 7.70–7.94 (4H, m).

EXAMPLE 57

Production of (5-methyl-2-oxo-1,3-dioxol-4-yl)methyl (Z)-3-cyclohexyl-2-(hydroxyisobutylphosphinoyl)methylpropenoate (Z)-3-cyclohexyl-2-(hydroxyisobutylphosphinoyl)methylpropenoic acid was treated in a similar manner as in Example 55 except that 4-chloromethyl-5-methyl-1,3- dioxol-2-one was used instead of chloromethyl pivalate in Example 55. The captioned compound was obtained as colorless crystals.

m.p.: 129.5°14 131.5° C.

IR (KBr, cm$^{-1}$): 2932, 1824, 1722, 1221, 1146, 1047, 1014, 981.

High-resolution FAB-MS
[m/e, for $(C_{19}H_{29}O_7P+H)^+$].
Calculated: 401.1729.
Found: 401.1737.

$^1$H-NMR (CD OD, δ ppm): 1.05 (6H, d, J=6.6 Hz), 1.14–1.78 (10H, m), 1.62 (2H, dd, J=6.6 Hz, 13.2 Hz), 2.02–2.16 (1H, m), 2.19 (3H, s), 2.43–2.57 (1H, m), 2.92 (2H, d, J=16.2 Hz), 4.99 (2H, s), 6.76 (1H, dd, J=5.1 Hz, 10.8 Hz).

EXAMPLE 58

Production of 2-ethoxy-2-oxoethyl (Z)-3-cyclohexyl-2-(hydroxyisobutylphosphinoyl)methylpropenoate (Z)-3-cyclohexyl-2-(hydroxyisobutylphosphinoyl)methylpropenoic acid was treated in a similar manner as in Example 55 except that ethyl bromoacetate was used instead of chloromethyl pivalate in Example 55. The captioned compound was obtained as colorless crystals.

m.p.: 77.5°–78° C.

IR (KBr, cm$^{-1}$): 2938, 1764, 1731, 1212, 1149, 1086, 951.

High-resolution FAB-MS
[m/e, for $(C_{18}H_{31}O_6P+H)^+$].
Calculated: 375.1937.
Found: 375.1963.

$^1$H-NMR (CD$_3$OD, δ ppm): 1.05 (6H, d, J=6.6 Hz), 1.27 (3H, t, J=7.2 Hz), 1.15–1.76 (12H, m), 2.06–2.16 (1H, m), 2.45–2.60 (1H, m), 2.94 (2H, d, J=17.1 Hz), 4.21 (2H, q, J=7.2 Hz), 4.70 (2H, s), 6.86 (1H, dd, J=4.8 Hz, 10.5 Hz).

EXAMPLE 59

Preparation of tablets

| 250 mg/320 mg tablets | |
|---|---|
| Compound No. 2 | 250 parts |
| Lactose | 34 parts |
| Corn starch | 15 parts |
| Calcium carboxymethylcellulose | 13 parts |
| Methylcellulose | 6 parts |
| Magnesium stearate | 2 parts |
| | 320 parts |

Compound No. 2 (250 parts), 34 parts of lactose, 15 parts of corn starch and 13 parts of calcium carboxymethylcellulose were uniformly mixed, and a paste prepared from 6 parts of methylcellulose and purified water was added and kneaded with the mixture. The resulting mixture was mixed with 2 parts of magnesium stearate and tableted by a conventional method to give tablets each containing 250 mg of compound No. 2.

EXAMPLE 60

Preparation of granules:

| 350 mg/1 g | |
|---|---|
| Compound No. 27 | 350 parts |
| Lactose | 490 parts |
| Corn starch | 150 parts |
| Hydroxypropylcellulose | 10 parts |
| | 1000 parts |

Compound No. 27 (350 parts), 490 parts of lactose and 150 parts of corn starch were uniformly mixed. A paste prepared from 10 parts of hydroxypropylcellulose and purified water was kneaded with the mixture. The kneaded mixture was granulated by a conventional method, and adjusted in size to give granules containing 350 mg of compound No. 27 per gram.

EXAMPLE 61

Preparation of injections (for intravenous drip infusion)

| 250 mg/100 ml | |
|---|---|
| Compound No. 2 | 250 mg |
| Sodium hydrogen carbonate | 150 mg |
| Saline | to make 100 ml |

Compound No. 2 (250 mg) was dissolved in a solution of 150 mg of sodium hydrogen carbonate in 20 ml of saline. Then, saline was added to adjust the total amount of the solution to 100 ml. After sterilization and filtration, the solution was filled in a vial to form an injection.

EXAMPLE 62

Preparation of injections (for intravenous drip infusion)

| 250 mg/100 ml | |
|---|---|
| Compound No. 2 (disodium salt) | 288 mg |
| Saline | to make 100 ml |

Disodium salt of compound No. 2 (288 mg) was dissolved in saline to form 100 ml of a solution. After sterilization and filtration, the solution was filled in a vial to form an injection.

EXAMPLE 63

Preparation of injections

| 250 mg/2 ml | |
|---|---|
| Compound No. 2 (disodium salt) | 288 mg |
| Distilled water for injection | to make 2 ml |

The disodium salt of compound No. 2 (288 mg) was dissolved in distilled water for injection to form 2 ml of a solution. After filtration, the solution was filled in an ampoule, and then heat-sterilized at 120° C. for 20 minutes to form an injection.

ADVANTAGE OF THE INVENTION

Since the compounds of this invention are long-lasting in vivo and show the effect even in oral administration, these compounds are expected to improve the therapeutic effect of carbapenem or penem antibiotics on bacterial infections of mammals including man when used in combination with the antibiotics.

We claim:

1. A phosphinic acid derivative of formula (I) or a pharmaceutically acceptable salt thereof, $$R^1-\underset{\underset{OR^2}{|}}{\overset{\overset{O}{\|}}{P}}-CH_2-A-CO_2R^5 \quad (I)$$

in which $R^1$ represents a linear or branched alkyl group having 1 to 10 carbon atoms which may be substituted by a hydroxyl group, a lower alkoxy-lower alkyloxy group or a halogen atom; a cycloalkyl-lower alkyl group having 4 to 10 carbon atoms; a cycloalkyl group having 3 to 6 carbon atoms in the ring which may be substituted by 1 to 4 identical or different lower alkyl groups; or an aralkyl group having 7 to 11 carbon atoms;

$R^2$ represents a hydrogen atom;

$R^5$ represents a hydrogen atom, a 1-(lower alkylcarbonyloxy)lower alkyl group, a phthalidyl group, a lower alkoxycarbonylmethyl group or a 1-(5-lower alkyl or phenyl-2-oxo-1,3-dioxol-4-yl)lower alkyl group; and A represents a group of the formula $$-\underset{\underset{CH-R^{3a}}{\|}}{\overset{}{C}}-$$

wherein $R^{3a}$ represents a phenyl group; an aralkyl group having 7 to 11 carbon atoms; a cycloalkyl-lower alkyl group having 4 to 10 carbon atoms; or a linear or branched alkyl group having 1 to 10 carbon atoms or a cycloalkyl group having 3 to 6 carbon atoms in the ring, which may be substituted by a halogen atom, a carboxyl group, a di-lower alkyl-substituted amino group, an N-methyl-N-carboxymethylamino group, a phenylthio group, a triazolythio group, a carboxy-lower alkylthio group, a lower alkoxycarbonyl-lower alkylthio group, a pyridylthio group, hydroxy substituted pyridylthio group, an imidazolylthio group, a lower alkyl substituted imidazolylthio group, a hydroxy-lower-alkylthio group, an amino-lower alkylthio group or a 2-amino-2-carboxyethylthio group; and the double bond at A has a Z-configuration, or a group of the formula $$-\underset{\underset{CH_2R^{4a}}{|}}{CH}-$$

wherein $R^{4a}$ represents a cycloalkyl group having 3 to 6 carbon atoms.

2. A phosphinic acid derivative of formula according to claim 1, or a pharmaceutically acceptable salt thereof, in which $R^1$ represents a linear or branched alkyl group having 3 to 10 carbon atoms; a cycloalkyl group having 3 to 6 carbon atoms in the ring which may be substituted by 1 to 4 identical or different lower alkyl groups; or a cycloalkyl-lower alkyl group having 4 to 10 carbon atoms;

$R^2$ represents a hydrogen atom;

$R^5$ represents a hydrogen atom, a 1-(lower alkylcarbonyloxy)lower alkyl group, a phthalidyl group, a lower alkoxycarbonylmethyl group or a 1-(5-lower alkyl or phenyl-2-oxo-1,3-dioxol-4-yl)lower alkyl group; and A represents a group of the formula

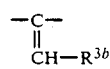

wherein $R^{3b}$ represents a phenyl group; an aralkyl group having 7 to 11 carbon atoms; a cycloalkylmethyl group having 4 to 7 carbon atoms; or a linear or branched alkyl group having 1 to 10 carbon atoms or a cycloalkyl group having 3 to 6 carbon atoms in the ring, which may be substituted by a halogen atom, a carboxyl group, a phenylthio group, a 1,2,3-triazol-4-yl-thio group, a carboxy-lower alkylthio group, a lower alkoxycarbonyl-lower alkylthio group, a 3-hydroxy-2-pyridylthio group, a 1-methyl-2-imidazolythio group, a hydroxy-lower alkylthio group or a 2-amino-2-carboxyethylthio group; and the double bond at A has a Z-configuration, or a group of the formula

wherein $R^{4a}$ represents a cycloalkyl group having 3 to 6 carbon atoms.

3. A phosphinic said derivative according to claim 1, or a pharmaceutically acceptable salt thereof, in which $R^1$ represents a linear or branched alkyl group having 3 to 10 carbon atoms; a cycloalkyl group having 3 to 6 carbon atoms in the ring which may be substituted by 1 to 2 lower alkyl groups; or a cycloalkyl-methyl group having 4 to 7 carbon atoms;

$R^2$ represents a hydrogen atom;

$R^5$ represents a hydrogen atom, a lower alkylcarbonyloxymethyl group, a phthalidyl group or a (5-methyl-2-oxo-1,3-dioxol-4-yl)methyl group; and A represents a group of the formula

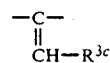

wherein $R^{3c}$ represents a linear or branched alkyl group having 3 to 10 carbon atoms, or a cycloalkyl group having 3 to 6 carbon atoms; and the double bond at A has a Z-configuration.

4. A compound according to claim 1 which is (Z)-2-(butylhydroxyphosphinoyl)methyl-3-cyclohexylpropenoic acid, (Z)-3-cyclohexyl-2-(hydroxyisobutylphosphinoyl)methylpropenoic acid, (Z)-3-cyclohexyl-2-(hydroxyisopropylphosphinoyl)methylpropenoic acid, (Z)-3-cyclohexyl-2-(decylhydroxyphosphinoyl)methylpropenoic acid, (Z)-3-cyclohexyl-2-(2,2-dimethylcyclopropylhydroxyphosphinoyl)methylpropenoic acid, (Z)-2-(hydroxyisobutylphosphinoyl)methyl-2-octenoic acid, (Z)-2-(hydroxyisobutylphosphinoyl)methyl-2-dodecenoic acid, (Z)-2-(hydroxyisobutylphosphinoyl)methyl-4-methyl-2-pentenoic acid, (Z)-2-(hydroxyisobutylphosphinoyl)methyl-5-methyl-2-hexenoic acid, (Z)-3-cyclopropyl-2-(hydroxyisobutylphosphinoyl)methylpropenoic acid, (Z)-3-cyclopentyl-2-(hydroxyisobutylphosphinoyl)methylpropenoic acid, (Z)-2-(hydroxyisobutylphosphinoyl)methyl-5-phenyl-2-pentenoic acid, (Z)-6-chloro-2-(hydroxyisobutylphosphinoyl)-methyl-2-hexenoic acid, (Z)-8-chloro-2-(hydroxyisobutylphosphinoyl)-methyl-2-octenoic acid, (Z)-2-(hydroxyisobutylphosphinoyl)methyl-2-heptenedioic acid, (Z)-3-cyclopropyl-2-(2,2-dimethylcyclopropylhydroxyphosphinoyl)methylpropenoic acid, (Z)-2-(cyclohexylmethylhydroxyphosphinoyl)-2-methyl-3-cyclopropylpropenoic acid, (Z)-3-cyclohexyl-2-(cyclopentylmethylhydroxyphosphinoyl)methylpropenoic acid, (Z)-2-(hydroxyisobutylphosphinoyl)methyl-6-phenylthio-2-hexenoic acid, (Z)-2-(hydroxyisobutylphosphinoyl)methyl-6-(1,2,3-triazol-4-yl)thio-2-hexenoic acid, (Z)-8-carboxymethylthio-2-(hydroxyisobutylphosphinoyl)methyl-2-octenoic acid, (Z)-2-(hydroxyisobutylphosphinoyl)methyl-8-methoxycarbonylmethylthio-2-octenoic acid, (Z)-6-(3-hydroxy-2-pyridyl)thio-2-(hydroxyisobutylphosphinoyl)methyl-2-hexenoic acid, (Z)-6-[(L)-2-amino-2-carboxyethyl]thio-2-(hydroxyisobutylphosphinoyl)methyl-2-hexenoic acid, (Z)-2-(hydroxyisobutylphosphinoyl)methyl-6-(1-methylimidazol-2-yl)thio-2-hexenoic acid, (Z)-8-(3-hydroxy-2-pyridyl)thio-2-(hydroxyisobutylphosphinoyl)methyl-2-octenoic acid, 2-(butylhydroxyphosphinoyl)methyl-3-cyclohexylpropionic acid, (5-methyl-2-oxo-1,3-dioxol-4-yl)methyl (Z)-3-cyclohexyl-2-(hydroxyisobutylphosphinoyl)methylpropenoate, phthalidyl (Z)-3-cyclohexyl-2-(hydroxyisobutylphosphinoyl)methylpropenoate, pivaloyloxymethyl (Z)-3-cyclohexyl-2-(hydroxyisobutylphosphinoyl)methylpropenoate, 1-acetoxyethyl (Z)-3-cyclohexyl-2-(hydroxyisobutylphosphinoyl)methylpropenoate, or a pharmaceutically acceptable salt thereof.

5. A compound represented by the following formula

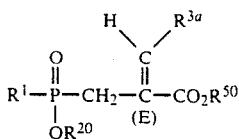

wherein $R^1$ and $R^{3a}$ are as defined in claim 1, and $R^{20}$ and $R^{50}$ may be identical or different, and each represents a hydrogen atom or a lower alkyl group, or a salt thereof.

6. A compound represented by the following formula

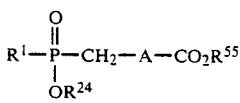

wherein $R^1$ and A are as defined in claim 1, and $R^{24}$ and $R^{55}$ may be identical or different, and each represents a hydrogen atom or a lower alkyl group; provided that $R^{24}$ and $R^{55}$ are not hydrogen atoms at the same time, or a salt thereof.

7. A pharmaceutical composition comprising an effective amount of a phosphinic acid derivative of general formula [I] or its pharmaceutically acceptable salt according to claim 1 and an adjuvant.

8. A method of reducing renal toxicity induced by the administration of a carbapenem or penem antibiotic substance to a patient, which comprise administering an effective amount of a phosphinic acid derivative of general formula [I] or its pharmaceutically acceptable salt according to claim 1 to the patient.

9. A method for inhibiting in vivo dipeptidase enzyme inactivation of carbopenem or penem antibiotic which comprises administering to a patient in need thereof an effective amount of a carbopenem or penem antibiotic and a phosphonic acid derivative of formula (I) according to claim 1 or a pharmaceutically acceptable salt thereof.

10. The method of claim 9 wherein the antibiotic and the phosphonic acid derivative of formula (I) are administered separately to the patient in need thereof.

11. The method of claim 9 wherein a mixture of the antibiotic and phosphonic acid derivative of formula (I) are administered to the patient in need thereof.

12. The method of claim 9 wherein the phosphonic acid derivative of formula (I) is administered orally to the patient in need thereof.

13. The method of claim 9 wherein the phosphonic acid derivative of formula (I) is administered parenterally to the patient in need thereof.

* * * * *